United States Patent
Riley et al.

(10) Patent No.: US 11,452,782 B2
(45) Date of Patent: Sep. 27, 2022

(54) LIVER-SPECIFIC CONSTRUCTS FACTOR VIII EXPRESSION CASSETTES AND METHODS OF USE THEREOF

(71) Applicant: Sangamo Therapeutics, Inc., Richmond, CA (US)

(72) Inventors: Brigit E. Riley, Richmond, CA (US); Gary K. Lee, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 769 days.

(21) Appl. No.: 16/172,461

(22) Filed: Oct. 26, 2018

(65) Prior Publication Data

US 2019/0151472 A1     May 23, 2019

Related U.S. Application Data

(62) Division of application No. 15/209,363, filed on Jul. 13, 2016, now Pat. No. 10,143,760.

(60) Provisional application No. 62/247,469, filed on Oct. 28, 2015, provisional application No. 62/307,897, filed on Mar. 14, 2016, provisional application No. 62/326,229, filed on Apr. 22, 2016, provisional application No. 62/315,438, filed on Mar. 30, 2016, provisional application No. 62/355,106, filed on Jun. 27, 2016.

(51) Int. Cl.
| | |
|---|---|
| *A61K 48/00* | (2006.01) |
| *C12N 15/63* | (2006.01) |
| *A61P 7/02* | (2006.01) |
| *C12N 15/90* | (2006.01) |
| *A61K 38/37* | (2006.01) |
| *A61K 45/06* | (2006.01) |
| *C07K 14/755* | (2006.01) |
| *C12N 7/00* | (2006.01) |
| *C12N 15/86* | (2006.01) |
| *A01K 67/00* | (2006.01) |
| *A61K 38/00* | (2006.01) |

(52) U.S. Cl.
CPC .......... *A61K 48/0058* (2013.01); *A61K 38/37* (2013.01); *A61K 45/06* (2013.01); *A61K 48/00* (2013.01); *A61P 7/02* (2018.01); *C07K 14/755* (2013.01); *C12N 7/00* (2013.01); *C12N 15/86* (2013.01); *C12N 15/907* (2013.01); *A61K 38/00* (2013.01); *C12N 2750/14143* (2013.01); *C12N 2750/14145* (2013.01); *C12N 2750/14171* (2013.01); *C12N 2830/008* (2013.01); *C12N 2830/42* (2013.01); *C12N 2830/60* (2013.01)

(58) Field of Classification Search
CPC ................ A61K 48/0058; A61K 48/00; C12N 15/907; C12N 15/86; C12N 2830/42; C12N 2830/60; C12N 2750/14143; C12N 2750/14145; C12N 2750/14171; C12N 2830/008; C07K 14/755
See application file for complete search history.

(56) References Cited

U.S. PATENT DOCUMENTS

| | | | |
|---|---|---|---|
| 6,200,560 | B1 | 3/2001 | Couto |
| 6,221,349 | B1 | 4/2001 | Couto |
| 6,503,717 | B2 | 1/2003 | Case |
| 6,534,261 | B1 | 3/2003 | Cox, III |
| 6,599,692 | B1 | 7/2003 | Case |
| 6,689,558 | B2 | 2/2004 | Case |
| 6,936,243 | B2 | 8/2005 | Snyder |
| 7,067,317 | B2 | 6/2006 | Rebar |
| 7,238,346 | B2 | 7/2007 | Vandendrissche |
| 7,262,054 | B2 | 8/2007 | Jamieson |
| 7,888,121 | B2 | 2/2011 | Urnov |
| 7,914,796 | B2 | 3/2011 | Miller |
| 7,951,925 | B2 | 5/2011 | Ando |
| 7,972,854 | B2 | 7/2011 | Miller |
| 8,034,598 | B2 | 10/2011 | Miller |
| 8,110,379 | B2 | 2/2012 | Dekelver |
| 8,409,861 | B2 | 4/2013 | Guschin |
| 8,586,526 | B2 | 11/2013 | Gregory |
| 8,623,618 | B2 | 1/2014 | Doyon |
| 8,703,489 | B2 | 4/2014 | Wang |
| 8,945,868 | B2 | 2/2015 | Collingwood |
| 8,956,828 | B2 | 2/2015 | Bonini |
| 9,005,973 | B2 | 4/2015 | Cost |
| 9,045,763 | B2 | 6/2015 | Dekelver |
| 9,150,847 | B2 | 10/2015 | Rebar |
| 9,175,280 | B2 | 11/2015 | Gregory |
| 9,200,266 | B2 | 12/2015 | Wang |
| 9,255,250 | B2 | 2/2016 | Gregory |
| 9,504,762 | B2 | 11/2016 | Colosi |
| 10,143,760 | B2 | 12/2018 | Riley et al. |
| 2003/0232410 | A1 | 12/2003 | Liljedahl |

(Continued)

FOREIGN PATENT DOCUMENTS

| | | |
|---|---|---|
| EP | 2451474 B1 | 12/2013 |
| WO | 2005/040384 | 5/2005 |

(Continued)

OTHER PUBLICATIONS

Niu et al. Applications of TALENs and CRISPR/Cas9 in human cells and their potentials for gene therapy. Mol. Biotechnol. 56:681-688, (Year: 2014).*

Gaj et al. ZFN, TALEN, and CRISPR/Cas-based methods for genome engineering. Trends in Biotechnology 31:397-405, (Year: 2013).*

Li, et al. "Human enhancers are fragile and prone to deactivating mutations." Molecular biology and evolution 32, No. 8 (2015): 2161-2180.

(Continued)

*Primary Examiner* — Quang Nguyen

(74) *Attorney, Agent, or Firm* — Steptoe & Johnson LLP; Z. Ying Li; Debashree Chatterjee

(57) ABSTRACT

Described herein are constructs used for liver-specific expression of a transgene.

26 Claims, 43 Drawing Sheets

Specification includes a Sequence Listing.

(56) References Cited

U.S. PATENT DOCUMENTS

| | | |
|---|---|---|
| 2005/0026157 A1 | 2/2005 | Baltimore |
| 2005/0064474 A1 | 3/2005 | Urnov |
| 2005/0208489 A1 | 9/2005 | Carroll |
| 2005/0276787 A1 | 12/2005 | Couto et al. |
| 2006/0063231 A1 | 3/2006 | Li |
| 2007/0154456 A1* | 7/2007 | Bloom ............... C12N 15/86 424/93.2 |
| 2008/0159996 A1 | 7/2008 | Ando |
| 2010/0218264 A1 | 8/2010 | Cui |
| 2011/0201055 A1 | 8/2011 | Doyon |
| 2011/0265198 A1 | 10/2011 | Gregory |
| 2012/0017290 A1 | 1/2012 | Cui |
| 2012/0128635 A1 | 5/2012 | Gregory |
| 2013/0122591 A1 | 5/2013 | Cost |
| 2013/0137104 A1 | 5/2013 | Cost |
| 2013/0177960 A1 | 7/2013 | Rebar |
| 2013/0177983 A1 | 7/2013 | Rebar |
| 2013/0196373 A1 | 8/2013 | Gregory |
| 2014/0017212 A1 | 1/2014 | Rebar |
| 2014/0093913 A1 | 4/2014 | Cost |
| 2014/0235693 A1 | 8/2014 | Sehgal |
| 2015/0056705 A1 | 2/2015 | Conway |
| 2015/0071883 A1 | 3/2015 | Colosi |
| 2015/0159172 A1 | 6/2015 | Miller |
| 2015/0166618 A1 | 6/2015 | Miller |
| 2015/0283267 A1 | 10/2015 | Vandendriessche |
| 2017/0016027 A1 | 1/2017 | Lee |
| 2017/0233455 A1 | 8/2017 | Falkner et al. |

FOREIGN PATENT DOCUMENTS

| | | |
|---|---|---|
| WO | 2007/021353 | 2/2007 |
| WO | 09/130208 B1 | 10/2009 |
| WO | 13/106787 B1 | 7/2013 |
| WO | 2014/043131 | 3/2014 |
| WO | 14/064277 B1 | 5/2014 |
| WO | 2014/162318 | 10/2014 |
| WO | 15/089046 B1 | 6/2015 |
| WO | 15/089077 B6 | 9/2015 |
| WO | 2017-011519 A1 | 1/2017 |
| WO | 2017/053677 A1 | 3/2017 |
| WO | 2017-074526 A1 | 5/2017 |

OTHER PUBLICATIONS

Kim, et al., "A 20 nucleotide upstream element is essential for the nopaline synthase (nos) promoter activity," Plant Mol Biol (1994) 24:105-17.

Donald, et al., "Mutation of either G box or I box sequences profoundly affects expression from the *Arabidopsis* rbcS-1A promoter," EMBO J. (1990) 9(6):1717-26.

Ha, et al., "Cis-acting regulatory elements controlling temporal and organ-specific activity of nopaline synthase promoter," Nucleic Acids Res. (1989) 17(1):215-23.

Costa, et al., "Site-directed mutagenesis of hepatocyte nuclear factor (HNF) binding sites in the mouse transthyretin (TTR) promoter reveal synergistic interactions with its enhancer region," Nucleic Acids Res. (1991) 19(15):4139-45.

Wang, et al., "Hepatocyte nuclear factor-4α interacts with other hepatocyte nuclear factors in regulating transthyretin gene expression," FEBS J. (2010) 277(19):4066-75.

Bril, "Tolerance to Factor VIII in a Transgenic Mouse Expressing Human Factor VIII CDNA Carrying an ARG(593) to CYS Substitution," Thromb. Haemost. 95(2):341-347 (2006).

Chavez, et al., "Long-Term Expression of Human Coagulation Factor VIII in a Tolerant Mouse Model Using the φC31 Integrase System," Human Gene Therapy 23(4):390-398 (2012).

Chuah, et al., "Liver-Specific Transcriptional Modules Identified By Genome-Wide in Silico Analysis Enable Efficient Gene Therapy in Mice and Non-Human Primates," Molecular Therapy 22:1605-1613 (2014).

Fagerlund, "The CPF1 CRISPR-CAS Protein Expands Genome-Editing Tools," Genom. Bio. 16:251 (2015).

Graham, et al., "Performance of AAV8 Vectors Expressing Human Factor IX From a Hepatic-Selective Promorter Following Intravenous Injection Into Rats," Genetic Vaccines Therapy 3:6-9 (2008).

Guillinger, "Fusion of Catalytically Inactive CAS9 to Foki Nuclease Improves the Specificity of Genome Modification," Nature Biotech. 32(6):577-582 (2014).

Haut, et al., "Inclusion of the NS2-SPECIFIC Exon in Minute Virus of Mice MRNA is Facilitated by an Intronic Splicing Enhancer That Affects Definition of the Downstream Small Intron," Virology 258:84-94 (1999).

Haut, et al., "Intron Definition is Required for Excision of the Minute Virus of Mice Small Intron and Definition of the Upstream Exon," Journal of Virology 1834-1843 (1998).

Johansen, et al., "Development of a Tail Vein Transection Bleeding Model in Fully Anaesthetized Haemophilia a Mice Characterization of Two Novel FVIII Molecules," Haemophilia 22(4):625-631 (2016) doi: 10.1111/hae.12907.

Kulkarni, "Sites of Initial Bleeding Episodes, Mode of Delivery and Age of Diagnosis in Babies With Haemophilia Diagnosed Before the Ae of 2 Years: a Report From the Centers for Disease Control and Prevention's (CDC) Universal Data Collection (UDC) Project," Haemophilia 15:1281-90 (2009).

Lee, "A New Potent HFIX Plasmid for Hemophilia B Gene Therapy," Pharm. Res. 7:1229-1232 (2004).

Levinson, "A Transcribe Gene in an Intron of the Human Factor VIII Gene" Genomics 7(1):1-11 (1990).

Ljung, "Prophylactic Infusion Regimens in the Management of Hemophilia," Thrombosis and Haemostasis 82(2):525-530 (1999).

McIntosh, "Therapeutic Levels of FVIII Following a Single Peripheral Vein Administration of RAAV Vector Encoding a Novel Human Factor VIII Variant," Blood 121(17):3335-3344 (2013).

Manno, et al., "AAV-Mediated Factor IX Gene Transfer to Skeletal Muscle in Patients With Severe Hemophilia B," Blood 101(8):2963-2972 (2003).

Manno, et al., "Successful Transduction of Liver in Hemophilia by AAV-Factor IX and Limitations Imposed by the Host Immune Response," Nature Medicine 12(3):342-347 (2006).

McCaffery, et al. "CRISPR-CAS9 D10A Nickase Target-Specific Fluorescent Labeling of Double Strand DNA for Whole Genome Mapping and Structural Variation Analysis," Nucleic Acids Res. 44(2):e11 doi: 10.1093/nar/gkv878. Epub Oct. 19, 2015 (2016).

Nair, et al., "Computationally Designed Liver-Specific Transcriptional Modules and Hyperactive Factor IX Improve Hepatic Gene Therapy," Blood 123:3195-3199 (2014).

Nathwani, et al., "Long-Term Safety and Efficacy Following Systemic Administration of a Self-Complementary AAV Vector Encoding Human Fix Pseudotyped With Serotype 5 and 8 CAPSID Proteins," Molecular Therapy 19(5):876-885 (2011).

Nathwani, et al., "Adenovirus-Associated Virus Vector-Mediated Gene Transfer in Hemophilia B," N. Engl. J. Med. 365(25):2357-2365 (2011).

Osorio, "Role of Dendritic Cells in the Induction of Lymphocyte Tolerance," Frontiers in Immunology 6(Article 535):1-11 (2015).

Raker, "Tolerogenic Dendritic Cells for Regulatory T Cell Induction in Man," Frontier in Immunology 6(Article 569):1-11 (2015).

Scott & Lozier, "Gene Therapy for Haemophilia: Prospects and Challenges to Prevent or Reverse Inhibitor Formation" Br. J. Haematol. 156(3):295-302 (2012).

Shi, et al., "Lentivirus-Mediated Platelet-Derived Factor VIII Gene Therapy in Murine Haemophilia A," J. Thromb Haemost. 5(2):352-361 (2007).

"Extended European Search Report," dated Jul. 31, 2019, 7 pages.

Brown, et al., "Bioengineered Coagulation Cactor VIII Enables Long-term Correction of Murine Hemophilia A Following Liver-directed Adeno-associated Viral Vector Delivery," Molecular Therapy; Methods & Clinical Development (2014) 1:14036.

Nu, et al., "Optimization of Self-complementary AAV Vectors for Liver-directed Expression Results in Sustained Correction of Hemophilia B at Low Vector Dose," Mol Ther, (2008) 16(2):280-89.

* cited by examiner

CRMSBS1 = Changes at 1, 2, 3, 4
CRMSBS2 = Changes at 1, 3, 4, 5

| Number | Name | Figure with Map |
|---|---|---|
| 1 | Formulation | - |
| 2 | Parent | Fig 4 |
| 3 | CRMSBS1 | Fig 6 |
| 4 | CRMSBS1 No intron | Fig 6 |
| 5 | CRMSBS1 T-chimeric intron | Fig 6 |
| 6 | CRMSBS2 | Fig 4 |
| 7 | CRMSBS2 No intron | Fig 7 |
| 8 | CRMSBS2 T-chimeric intron | Fig 7 |

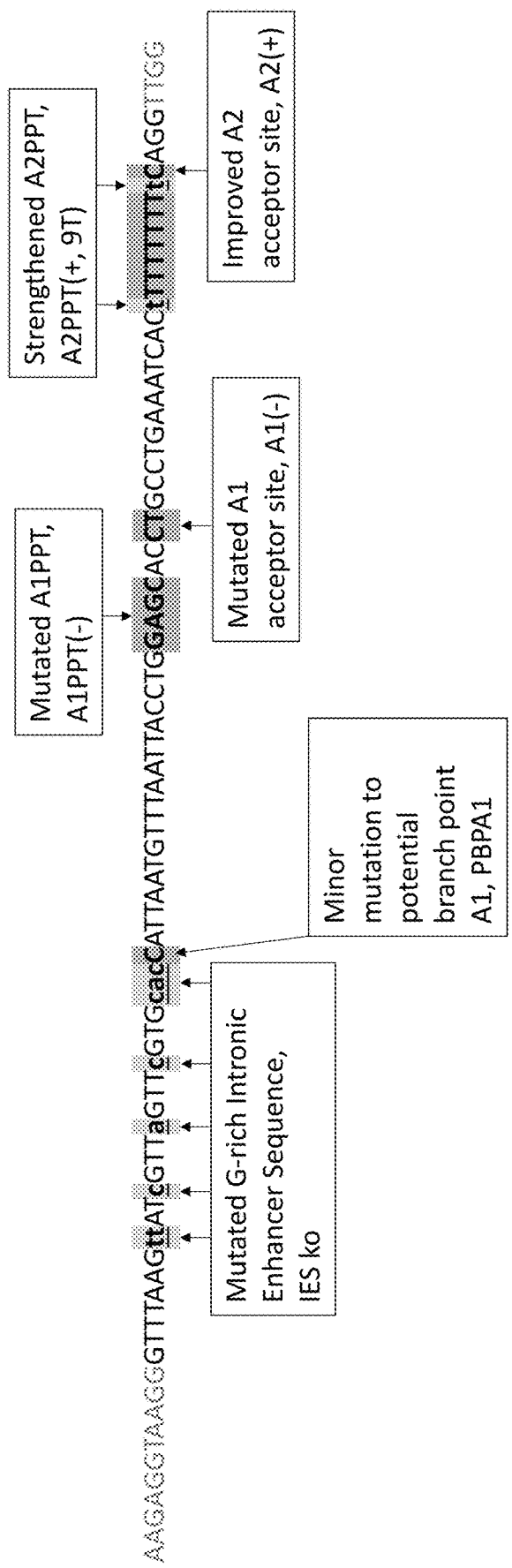

Peak Levels (28 Day Study)

Day 7

| Number | Name | Figure with Map |
|---|---|---|
| 1 | Formulation | - |
| 2 | Parent | Fig 4 |
| 3 | CRMSBS2 | Fig 7 |
| 4 | CRMSBS2 SBR Intron 1 | Fig 8 |
| 5 | CRMSBS2 SBR Intron 2 | Fig 8 |
| 6 | CRMSBS2 SBR Intron 3 | Fig 8 |

CRMSBS2
SBR Intron 3

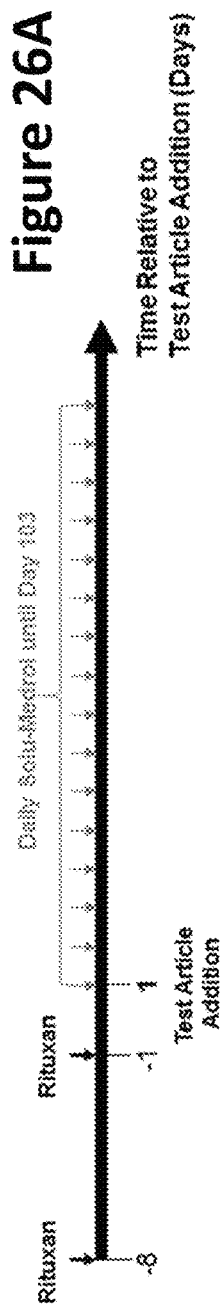

Figure 26A

| Group | No. of Animals Male | Test Article Identification | AAV Transgene Description | Serotype | Total rAAV Dose (vg/kg) |
|---|---|---|---|---|---|
| | Immunosuppression Regimen- Pre-Test Article Injection ||||||
| 1 | 1 | SGMO.01 | Formulation Buffer | NA | 0 |
| 2 | 3 | SGMO.02 | hF8 cDNA 1 | AAV2/6 | 2E+11 |
| 3 | 3 | SGMO.03 | hF8 cDNA 1 | AAV2/6 | 6E+11 |
| 4 | 3 | SGMO.04 | hF8 cDNA 1 | AAV2/6 | 2E+12 |
| 5 | 3 | SGMO.05 | hF8 cDNA 1 | AAV2/6 | 6E+12 |
| | Immunosuppression Regimen- Post-Test Article Injection ||||||
| 6 | 1 | SGMO.06 | hF8 cDNA 1 | NA | 0 |
| 7 | 3 | SGMO.07 | hF8 cDNA 1 | AAV2/6 | 2E+12 |
| 8 | 3 | SGMO.08 | hF8 cDNA 1 | AAV2/6 | 6E+12 |

Figure 26B

| Group | No. of Animals Male | Test Article Identification | AAV Transgene Description | Serotype | Total rAAV Dose (vg/kg) |
|---|---|---|---|---|---|
| | Redose at Day 56 of Group 2 ||||||
| 2 | 3 | SGMO.A | hF8 cDNA 1 | AAV2/6 | 9E+11 |

Vg - vector genome

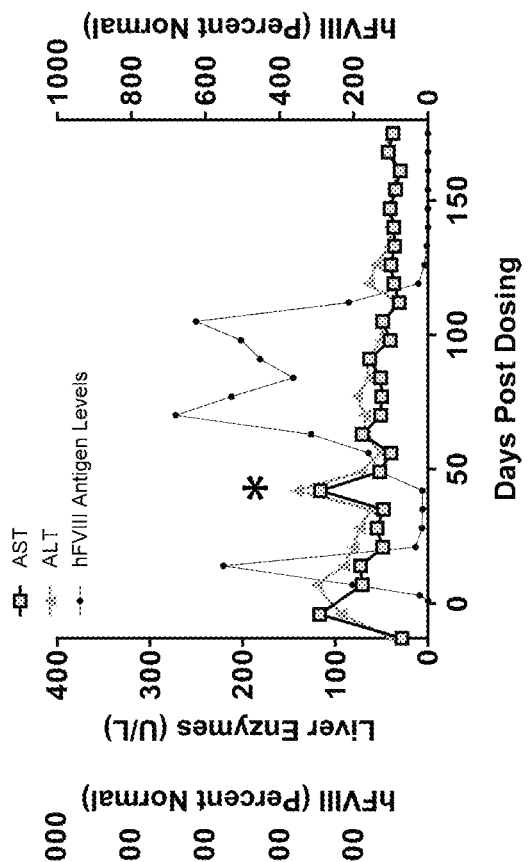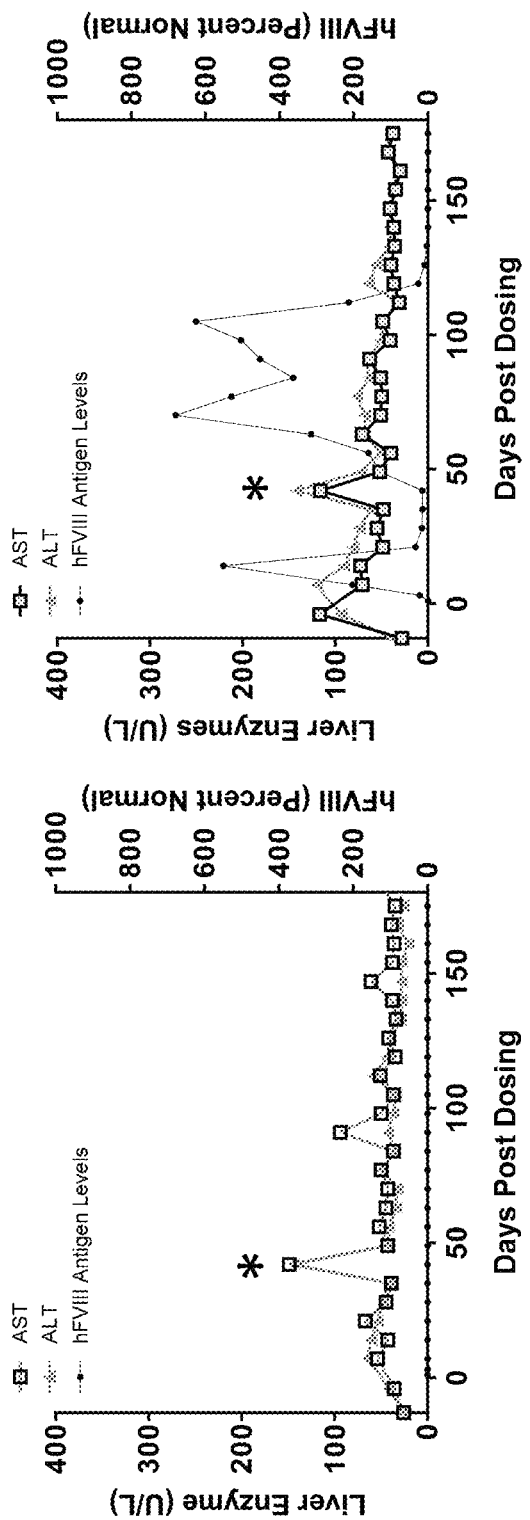
* Elevated levels observed post-liver biopsies (day 41)

Group 2, AAV2/6, 2E+12 vg/kg

Group 3, AAV2/6, 6E+12 vg/kg

Group 4, AAV2/8, 6E+12 vg/kg

Group 5, AAV2/8, 6E+12 vg/kg

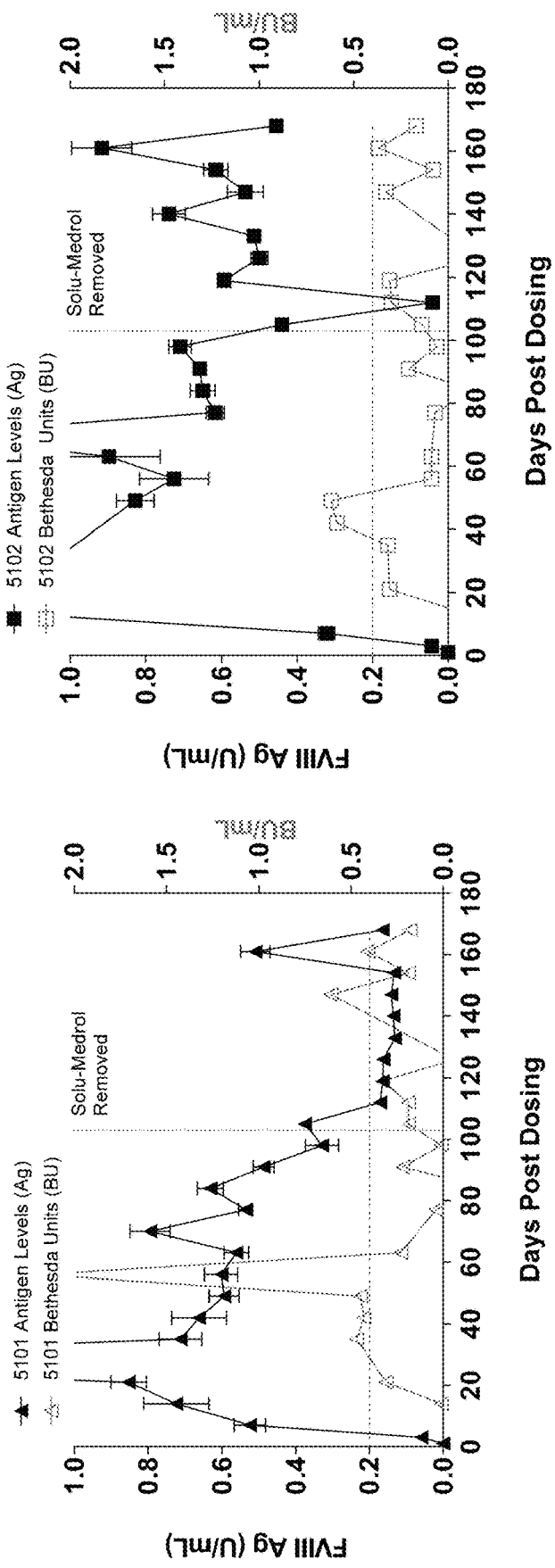
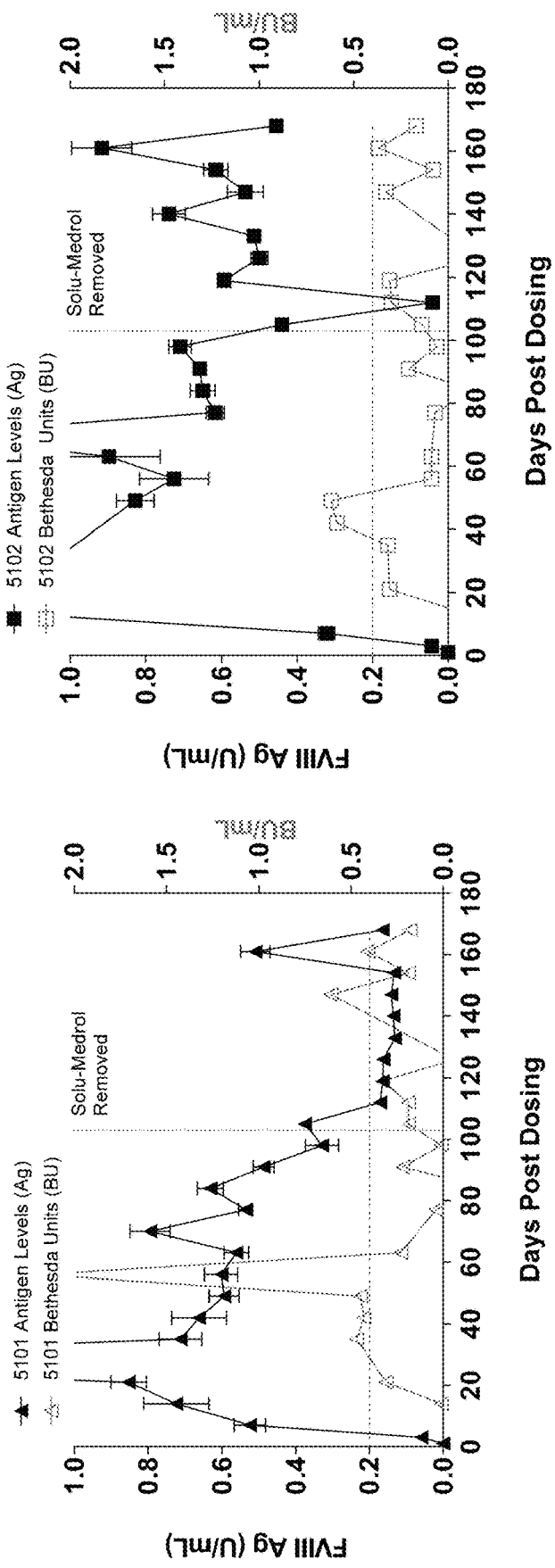
Figure 34D
Figure 34E
Group 5, AAV2/8, 6E+12 vg/kg

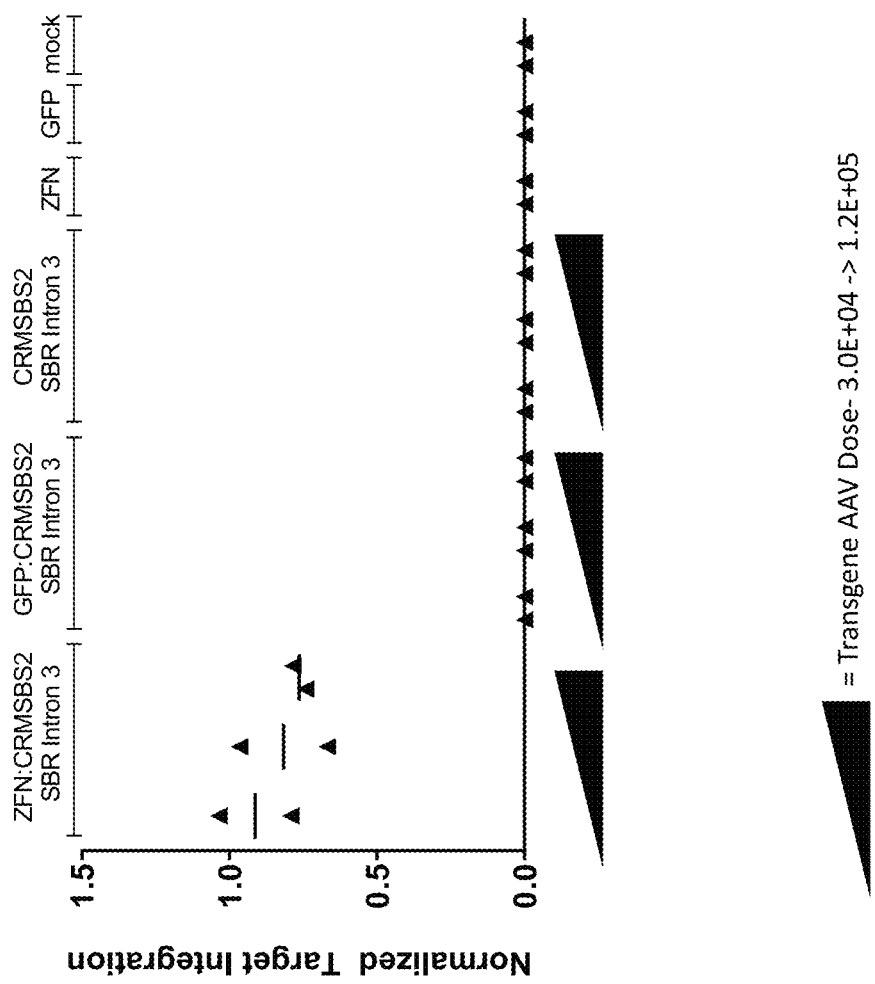

SEQUENCE LISTING

```
<160> NUMBER OF SEQ ID NOS: 47

<210> SEQ ID NO 1
<211> LENGTH: 40
<212> TYPE: DNA
<213> ORGANISM: Homo sapiens

<400> SEQUENCE: 1
gtcaccccag ttatcggagg agcaaacagg ggctaagtcc                40

<210> SEQ ID NO 2
<211> LENGTH: 40
<212> TYPE: DNA
<213> ORGANISM: Pan troglodytes

<400> SEQUENCE: 2
gtcaccccag ttatcggagg agcaaacagg ggctaagtcc                40

<210> SEQ ID NO 3
<211> LENGTH: 40
<212> TYPE: DNA
<213> ORGANISM: Gorilla sp.

<400> SEQUENCE: 3
gtcaccccag ttatcggagg agcaaacagg ggctaagtcc                40

<210> SEQ ID NO 4
<211> LENGTH: 40
<212> TYPE: DNA
<213> ORGANISM: Pongo sp.

<400> SEQUENCE: 4
gtcaccccag ttatcggagg agcaaacagg ggctaagtcc                40

<210> SEQ ID NO 5
<211> LENGTH: 40
<212> TYPE: DNA
<213> ORGANISM: Unknown
<220> FEATURE:
<223> OTHER INFORMATION: Description of Unknown: Oligonucleotide from
      Gibbon species

<400> SEQUENCE: 5
gtcaccccag ttatcggagg agcaaacagg ggctaagtcc                40

<210> SEQ ID NO 6
<211> LENGTH: 40
<212> TYPE: DNA
<213> ORGANISM: Macaca mulatta

<400> SEQUENCE: 6
atcaccccag ttaccggagg agcaaacagg gactaagttc                40
```

<210> SEQ ID NO 7
<211> LENGTH: 40
<212> TYPE: DNA
<213> ORGANISM: Macaca fascicularis

<400> SEQUENCE: 7
atcaccccag ttaccggagg agcaaacagg gactaagttc                              40

<210> SEQ ID NO 8
<211> LENGTH: 40
<212> TYPE: DNA
<213> ORGANISM: Papio sp.

<400> SEQUENCE: 8
atcaccccag ttaccggagg agcaaacagg gactaagttc                              40

<210> SEQ ID NO 9
<211> LENGTH: 40
<212> TYPE: DNA
<213> ORGANISM: Chlorocebus sabaeus

<400> SEQUENCE: 9
atcaccccag ttaccggagg agcaaacagg gactaagttc                              40

<210> SEQ ID NO 10
<211> LENGTH: 40
<212> TYPE: DNA
<213> ORGANISM: Unknown
<220> FEATURE:
<223> OTHER INFORMATION: Description of Unknown: Oligonucleotide from
      Callitrichidae family

<400> SEQUENCE: 10
gtcagcccag ttatcggagg agcaaacagg ggctaagtcc                              40

<210> SEQ ID NO 11
<211> LENGTH: 39
<212> TYPE: DNA
<213> ORGANISM: Saimiri sp.

<400> SEQUENCE: 11
gtcagcccag ttaccggagg agcaaacagg gctaagtcc                               39

<210> SEQ ID NO 12
<211> LENGTH: 38
<212> TYPE: DNA
<213> ORGANISM: Unknown
<220> FEATURE:
<223> OTHER INFORMATION: Description of Unknown: Oligonucleotide from
      Bush baby species

<400> SEQUENCE: 12
gtcacccagt tatcagggag caaacaggag ctaagtcc                                38

<210> SEQ ID NO 13
<211> LENGTH: 40
<212> TYPE: DNA
<213> ORGANISM: Mus sp.

<400> SEQUENCE: 13
gtcaccacag ttattggtag agcaaacagg ggctatgtcc                              40

<210> SEQ ID NO 14
<211> LENGTH: 88

```
<212> TYPE: DNA
<213> ORGANISM: Minute virus of mice

<400> SEQUENCE: 14
aagaggtaag ggtttaaggg atggttggtt ggtggggtat taatgtttaa ttacctgttt     60
tacaggcctg aaatcacttg gttttagg                                        88

<210> SEQ ID NO 15
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aagaggtaag ggtttaaggg atggttggtt ggtggggcat taatgtttaa ttacctgaac     60
gacgcgccac taatcacttt ttttcaggtt gg                                   92

<210> SEQ ID NO 16
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aagaggtaag ggtttaaggg atggttggtt ggtggggcat taatgtttaa ttacgacaac     60
gacgcgcctg aaatcacttt ttttcaggtt gg                                   92

<210> SEQ ID NO 17
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aagaggtaag ggtttaagtt atcgttagtt cgtgcaccat taatgtttaa ttacctggag     60
cacctgcctg aaatcacttt ttttttcagg ttgg                                 94

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggagatgaag aaggaggact ttg                                             23

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
acatctacga cgaggacgag aacca                                           25
```

```
<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tccacagcag caatgaagta g                                              21

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cctgggccag ttcctgct                                                  18

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
ttctgccaca tcagcagcca cca                                            23

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggcctccatg ccatcatg                                                  18

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agtgcaaagt aacttagagt gact                                           24

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
ccatcactag gggttcctgc ggcct                                          25
```

```
<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctgaaggtg gcaatggt                                                      18

<210> SEQ ID NO 27

<400> SEQUENCE: 27

000

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggaaccattg ccaccttca                                                     19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ctatccattg cactatgct                                                     19

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tttcctgtaa cgatcggg                                                      18

<210> SEQ ID NO 31
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aataaaatat ctttattttc attacatctg tgtgttggtt ttttgtgtgt t                 51

<210> SEQ ID NO 32
<211> LENGTH: 69
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 32
ataaaatatc tttattttca ttacatctgt gtgttggttt tttgtgtgtt ctatccattg      60
cactatgct                                                             69

<210> SEQ ID NO 33
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aataaaatat ctttattttc attacatctg tgtgttggtt ttttgtgtgt tttcctgtaa      60
cgatcggg                                                              68

<210> SEQ ID NO 34
<211> LENGTH: 4800
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gcggcctaag cttggaacca ttgccacctt caggggagg ctgctggtga atattaacca       60
agatcacccc agttaccgga ggagcaaaca gggactaagt tcacacgcgt ggtaccgtct     120
gtctgcacat ttcgtagagc gagtgttccg atactctaat ctccctaggc aaggttcata    180
tttgtgtagg ttacttattc tccttttgtt gactaagtca ataatcagaa tcagcaggtt    240
tggagtcagc ttggcaggga tcagcagcct gggttggaag gagggggtat aaaagccccct   300 tcaccaggag aagccgtcac acagatccac aagctcctgc tagtatgcag atcgagctct    360
ccacctgctt ctttctgtgc ctgttgagat tctgcttcag cgccaccagg agatactacc    420
tgggggctgt ggagctgagc tgggactaca tgcagtctga cctgggggag ctgcctgtgg    480
atgccaggtt ccccccccaga gtgcccaaga gcttcccctt caacacctct gtggtgtaca    540
agaagaccct gtttgtggag ttcactgacc acctgttcaa cattgccaag cccaggcccc    600
cctggatggg cctgctgggc ccaccatcc aggctgaggt gtatgacact gtggtgatca     660
ccctgaagaa catggccagc caccctgtga gcctgcatgc tgtggggtg agctactgga    720 aggcctctga gggggctgag tatgatgacc agaccagcca gagggagaag gaggatgaca    780
aggtgttccc tggggggcagc cacacctatg tgtggcaggt gctgaaggag aatggcccca    840
tggcctctga ccccctgtgc ctgacctaca gctacctgag ccatgtggac ctggtgaagg    900
acctgaactc tggcctgatt ggggccctgc tggtgtgcag gagggcagc ctggccaagg     960 agaagaccca gaccctgcac aagttcatcc tgctgtttgc tgtgtttgat gagggcaaga  1020
gctggcactc tgaaaccaag aacagcctga tgcaggacag ggatgctgcc tctgccaggg   1080
cctggcccaa gatgcacact gtgaatggct atgtgaacag gagcctgcct ggcctgattg   1140
gctgccacag gaagtctgtg tactggcatg tgattggcat gggcaccacc cctgaggtgc   1200
acagcatctt cctggagggc cacacttcc tggtcaggaa ccacaggcag gccagcctgg     1260
agatcagccc catcacctct ctgactgccc agaccctgct gatggacctg ggccagttcc  1320
```

```
tgctgttctg ccacatcagc agccaccagc atgatggcat ggaggcctat gtgaaggtgg    1380
acagctgccc tgaggagccc cagctgagga tgaagaacaa tgaggaggct gaggactatg    1440
atgatgacct gactgactct gagatggatg tggtgaggtt tgatgatgac aacagcccca    1500
gcttcatcca gatcaggtct gtggccaaga agcaccccaa gacctgggtg cactacattg    1560
ctgctgagga ggaggactgg gactatgccc ccctggtgct ggcccctgat gacaggagct    1620
acaagagcca gtacctgaac aatggccccc agaggattgg caggaagtac aagaaggtca    1680
ggttcatggc ctacactgat gaaaccttca agaccaggga ggccatccag catgagtctg    1740
gcatcctggg cccctgctg tatggggagg tggggacac cctgctgatc atcttcaaga    1800
accaggccag caggccctac aacatctacc cccatggcat cactgatgtg aggcccctgt    1860
acagcaggag gctgcccaag ggggtgaagc acctgaagga cttccccatc ctgcctgggg    1920
agatcttcaa gtacaagtgg actgtgactg tggaggatgg ccccaccaag tctgacccca    1980
ggtgcctgac cagatactac agcagctttg tgaacatgga gagggacctg gcctctggcc    2040
tgattggccc cctgctgatc tgctacaagg agtctgtgga ccagaggggc aaccagatca    2100
tgtctgacaa gaggaatgtg atcctgttct ctgtgtttga tgagaacagg agctggtacc    2160
tgactgagaa catccagagg ttcctgccca accctgctgg ggtgcagctg gaggaccctg    2220
agttccaggc cagcaacatc atgcacagca tcaatggcta tgtgtttgac agcctgcagc    2280
tgtctgtgtg cctgcatgag gtggcctact ggtacatcct gagcattggg gcccagactg    2340
acttcctgtc tgtgttcttc tctggctaca ccttcaagca caagatggtg tatgaggaca    2400 ccctgacct gttccccttc tctggggaga ctgtgttcat gagcatggag aaccctggcc    2460
tgtggattct gggctgccac aactctgact caggaacag gggcatgact gccctgctga    2520
aagtctccag ctgtgacaag aacactgggg actactatga ggacagctat gaggacatct    2580
ctgcctacct gctgagcaag aacaatgcca ttgagcccag gagcttcagc cagaatccac    2640
ccgtccttaa gcgccatcag cgcgagatca ccaggaccac cctgcagtct gaccaggagg    2700
agattgacta tgatgacacc atctctgtgg agatgaagaa ggaggacttt gacatctacg    2760
acgaggacga gaaccagagc cccagggagc tccagaagaa gaccaggcac tacttcattg    2820
ctgctgtgga gaggctgtgg gactatggca tgagcagcag ccccatgtgc tgaggaaca    2880 gggcccagtc tggctctgtg ccccagttca gaaggtggt gttccaggag ttcactgatg    2940
gcagcttcac ccagccctg tacagagggg agctgaatga gcacctgggc ctgctgggcc    3000
cctacatcag ggctgaggtg gaggacaaca tcatggtgac cttcaggaac caggccagca    3060
ggccctacag cttctacagc agcctgatca gctatgagga ggaccagagg caggggctg    3120 agcccaggaa gaactttgtg aagcccaatg aaaccaagac ctacttctgg aaggtgcagc    3180
accacatggc ccccaccaag gatgagtttg actgcaaggc ctgggcctac ttctctgatg    3240
tggacctgga aaggatgtg cactctggcc tgattggccc cctgctggtg tgccacacca    3300
acaccctgaa ccctgcccat ggcaggcagg tgactgtgca ggagtttgcc ctgttcttca    3360
ccatctttga tgaaaccaag agctggtact tcactgagaa catggagagg aactgcaggg    3420
ccccctgcaa catccagatg gaggacccca ccttcaagga aactacagg ttccatgcca    3480 tcaatggcta catcatggac accctgcctg gcctggtgat ggcccaggac cagaggatca    3540
ggtggtacct gctgagcatg ggcagcaatg agaacatcca cagcatccac ttctctggcc    3600
atgtgttcac tgtgaggaag aaggaggagt acaagatggc cctgtacaac ctgtaccctg    3660
```

```
gggtgtttga gactgtggag atgctgccca gcaaggctgg catctggagg gtggagtgcc    3720
tgattgggga gcacctgcat gctggcatga gcaccctgtt cctggtgtac agcaacaagt    3780
gccagacccc cctgggcatg gcctctggcc acatcaggga cttccagatc actgcctctg    3840
gccagtatgg ccagtgggcc cccaagctgg ccaggctgca ctactctggc agcatcaatg    3900
cctggagcac caaggagccc ttcagctgga tcaaggtgga cctgctggcc cccatgatca    3960
tccatggcat caagacccag ggggccaggc agaagttcag cagcctgtac atcagccagt    4020
tcatcatcat gtacagcctg gatggcaaga agtggcagac ctacaggggc aacagcactg    4080
gcaccctgat ggtgttcttt ggcaatgtgg acagctctgg catcaagcac aacatcttca    4140 accccccat cattgccaga tacatcaggc tgcaccccac ccactacagc atcaggagca     4200
ccctgaggat ggagctgatg ggctgtgacc tgaacagctg cagcatgccc ctgggcatgg    4260
agagcaaggc catctctgat gcccagatca ctgccagcag ctacttcacc aacatgtttg    4320
ccacctggag ccccagcaag gccaggctgc atctgcaggg caggagcaat gcctggaggc    4380
cccaggtcaa caaccccaag gagtggctgc aggtggactt ccagaagacc atgaaggtga    4440
ctggggtgac cacccagggg gtgaagagcc tgctgaccag catgtatgtg aaggagttcc    4500
tgatcagcag cagccaggat ggccaccagt ggaccctgtt cttccagaat ggcaaggtga    4560
aggtgttcca gggcaaccag gacagcttca cccctgtggt gaacagcctg gacccccccc    4620
tgctgaccag atacctgagg attcaccccc agagctgggt gcaccagatt gccctgagga    4680
tggaggtgct gggctgtgag gcccaggacc tgtactgagg atccaataaa atatctttat    4740
tttcattaca tctgtgtgtt ggttttttgt gtgttttcct gtaacgatcg ggctcgagcg    4800
```

<210> SEQ ID NO 35
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

```
gggggaggct gctggtgaat attaaccaag atcagcccag ttaccggagg agcaaacagg    60
ggctaagttc ac                                                       72
```

<210> SEQ ID NO 36
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

```
gggggaggct gctggtgaat attaaccaag atcaccccag ttaccggagg agcaaacagg    60
gactaagttc ac                                                       72
```

<210> SEQ ID NO 37
<211> LENGTH: 4894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
gcggcctaag cttggaacca ttgccacctt caggggagg ctgctggtga atattaacca      60
agatcacccc agttaccgga ggagcaaaca gggactaagt tcacacgcgt ggtaccgtct    120
gtctgcacat ttcgtagagc gagtgttccg atactctaat ctccctaggc aaggttcata    180
tttgtgtagg ttacttattc tccttttgtt gactaagtca ataatcagaa tcagcaggtt    240
tggagtcagc ttggcaggga tcagcagcct gggttggaag gaggggtat aaaagcccct     300
tcaccaggag aagccgtcac acagatccac aagctcctga agaggtaagg gtttaagtta    360
tcgttagttc gtgcaccatt aatgtttaat tacctggagc acctgcctga aatcattttt    420
ttttcaggtt ggctagtatg cagatcgagc tctccacctg cttctttctg tgcctgttga    480
gattctgctt cagcgccacc aggagatact acctggggc tgtggagctg agctgggact     540
acatgcagtc tgacctgggg gagctgcctg tggatgccag gttcccccc agagtgccca     600
agagcttccc cttcaacacc tctgtggtgt acaagaagac cctgtttgtg gagttcactg    660
accacctgtt caacattgcc aagcccaggc ccccctggat gggcctgctg gccccacca     720
tccaggctga ggtgtatgac actgtggtga tcaccctgaa gaacatggcc agccaccctg    780
tgagcctgca tgctgtgggg gtgagctact ggaaggcctc tgagggggct gagtatgatg    840
accagaccag ccagagggag aaggaggatg acaaggtgtt ccctggggc agccacacct     900
atgtgtggca ggtgctgaag gagaatggcc ccatggcctc tgaccccctg tgcctgacct    960
acagctacct gagccatgtg gacctggtga aggacctgaa ctctggcctg attggggccc   1020
tgctggtgtg cagggagggc agcctggcca aggagaagac ccagaccctg cacaagttca   1080
tcctgctgtt tgctgtgttt gatgagggca gagctggca ctctgaaacc aagaacagcc    1140
tgatgcagga cagggatgct gcctctgcca gggcctggcc aagatgcac actgtgaatg    1200
gctatgtgaa caggagcctg cctggcctga ttggctgcca caggaagtct gtgtactggc   1260
atgtgattgg catgggcacc accctgaggg tgcacagcat cttcctggag ggccacacct   1320
tcctggtcag gaaccacagg caggccagcc tggagatcag ccccatcacc ttcctgactg   1380
cccagaccct gctgatggac ctgggccagt tcctgctgtt ctgccacatc agcagccacc   1440
agcatgatgg catggaggcc tatgtgaagg tggacagctg ccctgaggag ccccagctga   1500
ggatgaagaa caatgaggag gctgaggact atgatgatga cctgactgac tctgagatgg   1560
atgtggtgag gtttgatgat gacaacagcc ccagcttcat ccagatcagg tctgtggcca   1620
agaagcaccc caagacctgg gtgcactaca ttgctgctga ggaggaggac tgggactatg   1680
ccccccctggt gctggcccct gatgacagga gctacaagag ccagtacctg aacaatggcc   1740
cccagaggat tggcaggaag tacaagaagg tcaggttcat ggcctacact gatgaaacct    1800
tcaagaccag ggaggccatc cagcatgagt ctggcatcct gggccccctg ctgtatgggg   1860
aggtggggga caccctgctg atcatcttca gaaccaggc cagcaggccc tacaacatct    1920
accccccatgg catcactgat gtgaggcccc tgtacagcag gaggctgccc aaggggtga    1980
agcacctgaa ggacttcccc atcctgcctg gggagatctt caagtacaag tggactgtga   2040
ctgtggagga tggccccacc aagtctgacc ccaggtgcct gaccagatac tacagcagct   2100
ttgtgaacat ggagagggac ctggcctctg gcctgattgg ccccctgctg atctgctaca   2160
aggagtctgt ggaccagagg ggcaaccaga tcatgtctga caagaggaat gtgatcctgt   2220
tctctgtgtt tgatgagaac aggagctggt acctgactga gaacatccag aggttcctgc   2280
```

```
ccaaccctgc tggggtgcag ctggaggacc ctgagttcca ggccagcaac atcatgcaca    2340
gcatcaatgg ctatgtgttt gacagcctgc agctgtctgt gtgcctgcat gaggtggcct    2400
actggtacat cctgagcatt ggggcccaga ctgacttcct gtctgtgttc ttctctggct    2460
acaccttcaa gcacaagatg gtgtatgagg acaccctgac cctgttcccc ttctctgggg    2520
agactgtgtt catgagcatg gagaaccctg gcctgtggat tctggctgc cacaactctg     2580 acttcaggaa caggggcatg actgccctgc tgaaagtctc cagctgtgac aagaacactg    2640
gggactacta tgaggacagc tatgaggaca tctctgccta cctgctgagc aagaacaatg    2700
ccattgagcc caggagcttc agccagaatc cacccgtcct taagcgccat cagcgcgaga    2760
tcaccaggac caccctgcag tctgaccagg aggagattga ctatgatgac accatctctg    2820
tggagatgaa gaaggaggac tttgacatct acgacgagga cgagaaccag agccccagga    2880
gcttccagaa gaagaccagg cactacttca ttgctgctgt ggagaggctg tgggactatg    2940
gcatgagcag cagcccccat gtgctgagga caagggccca gtctggctct gtgccccagt    3000
tcaagaaggt ggtgttccag gagttcactg atggcagctt cacccagccc ctgtacagag    3060 ggagctgaa tgagcacctg gcctgctgg gcccctacat cagggctgag gtggaggaca     3120
acatcatggt gaccttcagg aaccaggcca gcaggccta cagcttctac agcagcctga    3180
tcagctatga ggaggaccag aggcaggggg ctgagcccag gaagaacttt gtgaagccca    3240
atgaaaccaa gacctacttc tggaaggtgc agcaccacat ggccccacc aaggatgagt     3300 ttgactgcaa ggcctgggcc tacttctctg atgtggacct ggagaaggat gtgcactctg    3360
gcctgattgg ccccctgctg gtgtgccaca ccaacaccct gaaccctgcc catggcaggc    3420
aggtgactgt gcaggagttt gccctgttct tcaccatctt tgatgaaacc aagagctggt    3480
acttcactga gaacatggag aggaactgca gggcccctg caacatccag atggaggacc    3540
ccaccttcaa ggagaactac aggttccatg ccatcaatgg ctacatcatg gacaccctgc    3600
ctggcctggt gatggcccag gaccagagga tcaggtggta cctgctgagc atgggcagca    3660
atgagaacat ccacagcatc cacttctctg gccatgtgtt cactgtgagg aagaaggagg    3720
agtacaagat ggcccctgtac aacctgtacc ctgggggtgtt tgagactgtg gagatgctgc    3780
ccagcaaggc tggcatctgg agggtggagt gcctgattgg ggagcacctg catgctggca    3840
tgagcaccct gttcctggtg tacagcaaca agtgccagac ccccctgggc atggcctctg    3900
gccacatcag ggacttccag atcactgcct ctggccagta tggccagtgg gcccccaagc    3960
tggccaggct gcactactct ggcagcatca atgcctggag caccaaggag cccttcagct    4020
ggatcaaggt ggacctgctg gcccccatga tcatccatgg catcaagacc cagggggcca    4080
ggcagaagtt cagcagcctg tacatcagcc agttcatcat catgtacagc ctggatggca    4140
agaagtggca gacctacagg ggcaacagca ctggcaccct gatggtgttc tttggcaatg    4200
tggacagctc tggcatcaag cacaaacatct tcaaccccccc catcattgcc agatacatca    4260
ggctgcaccc caccactac agcatcagga gcaccctgag gatggagctg atgggctgtg    4320
acctgaacag ctgcagcatg cccctgggca tggagagcaa ggccatctct gatgcccaga    4380
tcactgccag cagctacttc accaacatgt tgccacctg gagcccccagc aaggccaggc    4440 tgcatctgca gggcaggagc aatgcctgga ggccccaggt caacaacccc aaggagtggc    4500
tgcaggtgga cttccagaag accatgaagg tgactggggt gaccacccag ggggtgaaga    4560
gcctgctgac cagcatgtat gtgaaggagt tcctgatcag cagcagccag gatggccacc    4620
agtggaccct gttcttccag aatggcaagg tgaaggtgtt ccagggcaac caggacagct    4680
```

-continued

```
tcacccctgt ggtgaacagc ctggaccccc ccctgctgac cagatacctg aggattcacc    4740
cccagagctg ggtgcaccag attgccctga ggatggaggt gctgggctgt gaggcccagg    4800
acctgtactg aggatccaat aaaatatctt tattttcatt acatctgtgt gttggttttt    4860
tgtgtgtttt cctgtaacga tcgggctcga gcgc                                4894
```

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttgaattcat aactatccca a                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtgtagcaga gaggaaccat t                                              21

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
ccatcactag gggttcctgc ggcct                                          25

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gttaatattc accagcagcc t                                              21

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
agtgtagcag agaggaacca                                                20

<210> SEQ ID NO 43
<211> LENGTH: 25
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 43
ccatcactag gggttcctgc ggcct                                              25

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cagggtgagc ccagaaac                                                      18

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aactttgagt gtagcagaga gg                                                 22

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
taccggagga gcaaacaggg acta                                               24

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ctctacgaaa tgtgcagaca ga                                                 22
```

LIVER-SPECIFIC CONSTRUCTS FACTOR VIII EXPRESSION CASSETTES AND METHODS OF USE THEREOF

CROSS-REFERENCE TO RELATED APPLICATIONS

The present application is a divisional of U.S. application Ser. No. 15/209,363, filed Jul. 13, 2016, which claims the benefit of U.S. Provisional Patent Application No. 62/247,469, filed Oct. 28, 2015; U.S. Provisional Patent Application No. 62/307,897, filed Mar. 14, 2016; U.S. Provisional Patent Application No. 62/326,229, filed Apr. 22, 2016; U.S. Provisional Patent Application No. 62/315,438, filed Mar. 30, 2016; and U.S. Provisional Patent Application No. 62/355,106, filed Jun. 27, 2016, the disclosures of which are hereby incorporated by reference in their entireties.

TECHNICAL FIELD

The present disclosure is in the field of gene therapy, particularly targeted delivery of transgene-encoding constructs to the liver for expression of beneficial (therapeutic) proteins. In particular, the disclosure relates to the treatment of hemophilias such as Hemophilia A.

BACKGROUND

Gene therapy can be used to genetically engineer a cell to have one or more inactivated genes and/or to cause that cell to express a product not previously being produced in that cell (e.g., via transgene insertion and/or via correction of an endogenous sequence). Examples of uses of transgene insertion include the insertion of one or more genes encoding one or more novel therapeutic proteins, insertion of a coding sequence encoding a protein that is lacking in the cell or in the individual, insertion of a wild type gene in a cell containing a mutated gene sequence, and/or insertion of a sequence that encodes a structural nucleic acid such as a microRNA or siRNA. Examples of useful applications of 'correction' of an endogenous gene sequence include alterations of disease-associated gene mutations, alterations in sequences encoding splice sites, alterations in regulatory sequences and/or targeted alterations of sequences encoding structural characteristics of a protein.

Hepatic gene transfer provides an effective means of delivering transgenes to a subject for treatment and/or prevention of various disorders, including hemophilias and lysosomal storage disorders. See, e.g., U.S. Pat. No. 9,150,847 and U.S. Publication Nos. 20130177983 and 20140017212. Vectors specific for liver-directed gene therapy have also been described. See, e.g., WO 2014064277; WO 2009130208; EP 2451474B1, Chuah et al., (2014) *Molecular Therapy,* 22, 1605-1613; and Nair et al. (2014) *Blood* 123:3195-3199. These vectors can include the wild-type mouse minute virus (MVM) intron sequence. See, e.g., Haut and Pintel (1998) *J. Virol.* 72:1834-1843; Haut and Pintel (1998) *Virol.* 258:84-94.

In whole mammals, there are complex mechanisms that can regulate either the activation or the suppression of the cellular members of the immune system. For example, dendritic cells (DCs) have been established as central players in the balance between immune activation versus immune tolerance. They are the most potent antigen presenting cells in the immune system and specifically capture and present antigens to naïve T cells. Immature DCs interact with potential antigens through specific receptors such as Toll-like receptors where the antigen is brought into the cell by micropinocytosis. The antigen is then broken up into smaller peptides that are presented to T cells by the major histocompatibility complexes. In addition, mature DCs secrete inflammatory mediators such as IL-1β, IL-12, IL-6 and TNF which further serve to activate the T cells. On the other side, DCs also play a role in tolerizing the body to some antigens in order to maintain central and peripheral tolerance. Tolerogenic DCs (tolDC) have low amounts of co-stimulatory signals on the cell surfaces and have a reduced expression of the inflammatory mediators described above. However, these tolDCs express large amounts of anti-inflammatory cytokines like IL-10 and when these cells interact with naïve T cells, the T cells are driven to become anergic/regulatory T cells (CD8+ Tregs). In fact, it has been shown that this process is enhanced upon repeated stimulation of T cells with these immature/tolerogenic DCs. Several factors have also been identified that work in concert with tolDCs to induce different types of Tregs. For example, naïve T cells co-exposed with tolDCs and HGF, VIP peptide, TSLP or Vitamin D3 leads to the induction of CD4+CD25+ Foxp3+ Tregs, co-exposure with TGF-β or IL-10 leads to Tr1 T regs and co-exposure with corticosteroids, rapamycin, retinoic acid can lead to CD4+/CD8+ Tregs (Raker et al (2015) *Front Immunol* 6: art 569 and Osorio et al (2015) *Front Immunol* 6: art 535).

Hemophilias such as Hemophilia A and Hemophilia B, are genetic disorders of the blood-clotting system, characterized by bleeding into joints and soft tissues, and by excessive bleeding into any site experiencing trauma or undergoing surgery. Hemophilia A is clinically indistinguishable from Hemophilia B, but factor VIII (FVIII or F8) is deficient or absent in Hemophilia A while factor IX (FIX or F.IX) is deficient or absent in patients with Hemophilia B. The F8 gene encodes a plasma glycoprotein that circulates in association with von Wilebrand's factor in its inactive form. Upon surface injury, the intrinsic clotting cascade initiates and FVIII is released from the complex and is activated. The activated form works with Factor IX to activate Factor X to become the activated Xa, eventually leading to change of fibrinogen to fibrin and clot induction. See, Levinson et al. (1990) *Genomics* 7(1):1-11. 40-50% of Hemophilia A patients have a chromosomal inversion involving F8 intron 22 (also known as IVS22). The inversion is caused by an intra-chromosomal recombination event between a 9.6 kb sequence within the intron 22 of the F8 gene and one of the two closely related inversely orientated sequences located about 300 kb distal to the F8 gene, resulting in an inversion of exons 1 to 22 with respect to exons 23 to 26. See, *Textbook of Hemophilia,* Lee et al. (eds) 2005, Blackwell Publishing. Other hemophilia A patients have defects in F8 including active site mutations, and nonsense and missense mutations.

Clinically, Hemophilia A patients are evaluated and stratified depending on how often a patient has a bleeding episode, and how long those episodes last. Both of these characteristics are directly dependent on the amount of FVIII protein in a patient's blood. Patients with severe hemophilia typically have less than 1% of the normal blood level of FVIII, experience bleeding following injury and often spontaneous bleeding into their joints. Moderate patients have 1-5% of the normal FVIII level while mild patients have 6% or more of normal FVIII and have bleeding episodes only after serious injury, trauma or surgery (Kulkarni et al (2009) *Haemophilia* 15:1281-90). Patients with Hemophilia A are treated with replacement FVIII protein derived either from human plasma or produced recombinantly where the frequency of treatment is based upon bleeding patterns and severity of the hemophilia. Patients with severe Hemophilia A receive prophylaxtic treatment on a regular basis to prevent bleeds from occurring while less severe patients can receive treatment only as needed following injury.

Gene therapy for patients with Hemophilia A or B, involving the introduction of plasmid and other vectors (e.g., AAV) encoding a functional FVIII or F.IX proteins have been described. (See, e.g., U.S. Pat. Nos. 6,936,243; 7,238,346 and 6,200,560; Shi et al. (2007)*J Thromb Haemost.* (2):352-61; Lee et al. (2004) *Pharm. Res.* 7:1229-1232; Graham et al. (2008) *Genet Vaccines Ther.* 3:6-9; Manno et al. (2003) *Blood* 101(8): 2963-72; Manno et al. (2006) *Nature Medicine* 12(3): 342-7; Nathwani et al. (2011)*Mol Ther* 19(5): 876-85; Nathwani et al. (2011); *N Engl J Med.* 365(25): 2357-65 and McIntosh et al. (2013) *Blood* 121(17): 3335-44). However, in these protocols, the formation of inhibitory anti-factor VIII or IX (anti-FVIII or anti-F.IX) antibodies, and antibodies against the delivery vehicle remains a major complication of FVIII and F.IX replacement-based treatment for hemophilia. See, e.g., Scott & Lozier (2012) *Br J Haematol.* 156(3):295-302.

However, there remains a need for liver-specific polynucleotides (expression constructs and transcription modules) that drive expression of one or more transgenes (including transgenes encoding one or more proteins lacking in a hemophilia) in liver cells at high levels.

SUMMARY

The present invention describes compositions and methods for expressing a transgene in a liver cell. The transgene may be expressed extra-chromosomally (episomally) or may be integrated into the genome of the liver cell (e.g., via nuclease-mediated targeted integration, for example into an albumin locus). In some embodiments, the transgene encodes a protein involved in the clotting cascade. In preferred embodiments, the transgene encodes a FVIII polypeptide. The compositions and methods described herein result in high levels of protein production both in vitro and in vivo, including at levels sufficient to show clinically relevant (therapeutic) effects in vivo.

In one aspect, described herein is a polynucleotide expression construct comprising at least one spacer sequence comprising an insulator sequence, a liver-specific enhancer sequence (e.g., a wild-type or mutated Serpin 1 enhancer sequence), a promoter sequence (e.g., a wild-type or mutated transthyretin (TTR) promoter) and a transgene (e.g., a nuclease and/or a therapeutic protein such as a protein lacking and/or deficient in a hemophilia or a lysosomal storage disease). In certain embodiments, the polynucleotide expression construct further comprises an intron sequence (e.g., a wild-type or mutated minute virus of mice (MVM) intron sequence). In certain embodiments, the polynucleotide expression cassette comprises two spacer sequences flanking the liver-specific enhancer sequence, the promoter sequence, the intron sequence and the transgene and optionally, a polyadenylation signal. Any insulator sequence(s) can be used, including but not limited to any wild-type or mutated insulator sequence (e.g., one or more of SEQ ID NO:28, 29, 30 and/or 38 in any combination). In certain embodiments, the polynucleotide expression construct comprises a polynucleotide designated CRMSBS1 (SEQ ID NO:37) or CRMSBS2 (SEQ ID NO:34).

In another aspect, described herein is a polynucleotide expression construct comprising a liver-specific enhancer sequence (e.g., a wild-type or mutated Serpin 1 enhancer sequence), a promoter sequence (e.g., a wild-type or mutated transthyretin (TTR) promoter), an intron sequence as shown in any one of SEQ ID NO:15, 16 or 17 and a transgene (e.g., a nuclease and/or a therapeutic protein such as a protein lacking and/or deficient in a hemophilia or a lysosomal storage disease). In certain embodiments, the polynucleotide expression cassette further comprises at least one spacer sequence comprising an insulator sequence and/or a polyadenylation signal.

In yet another aspect, described herein is a polynucleotide expression construct comprising a liver-specific enhancer sequence having mutations at positions 1, 5, 14, 32 and/or 39 of any of SEQ ID NOs:1-13 (e.g., as shown in SEQ ID NO:35 or 36), a promoter sequence (e.g., a wild-type or mutated transthyretin (TTR) promoter), and a transgene (e.g., a nuclease and/or a therapeutic protein such as a protein lacking and/or deficient in a hemophilia or a lysosomal storage disease). In certain embodiments, the polynucleotide expression constructs further comprises an intron sequence (e.g., a wild-type or mutated minute virus of mice (MVM) intron sequence) and/or at least one spacer sequence comprising an insulator sequence and/or a polyadenylation signal.

In other aspects, an AAV vector comprising any of the polynucleotide expression constructs described herein is provided (e.g., in which polynucleotide expression construct is between the 5' and 3' inverted terminal repeats (ITRs) of the AAV vector).

In yet other aspects, provided herein are pharmaceutical compositions comprising one or more AAV vectors and/or one or more polynucleotide expression constructs as described herein.

Also provided are methods for providing a protein to a subject in need thereof, the method comprising administering to the liver of the subject a polynucleotide expression construct, an AAV vector or a pharmaceutical composition as described herein to the subject, wherein the transgene encodes the protein and the protein is produced in the subject. In certain embodiments, the transgene is integrated into the genome of a liver cell in the subject. Optionally, the methods further comprise administering one or more nucleases to the subject, wherein the nuclease cleave an endogenous albumin gene and the transgene is integrated into the endogenous albumin gene. Methods of genetically modifying a cell to include a transgene (e.g., that produces a protein) are also provided, including methods introducing the transgene into the cell (episomally or integrated including nuclease-mediated targeted integration). Also provided are methods of inducing tolerance in a mammal to a therapeutic protein, the method comprising genetically modifying a cell (e.g., a cell that has been modified to produce a protein as described herein) in a subject as described herein and treating the one or more steroids and/or B-cell inhibitors such that the mammal becomes tolerized to the therapeutic protein.

In one aspect, described herein is a polynucleotide expression construct comprising an enhancer sequence (e.g., a wild-type or mutated Serpin1 enhancer), a promoter sequence (e.g., a transthyretin minimal promoter (TTRm) promoter), and the transgene and, optionally, a polyadenylation sequence (e.g., a synthetic polyadenylation sequence (SPA) and/or a signal peptide (SP). In certain embodiments, the expression construct further comprises an intron sequence (e.g., wild-type MVM or a mutated MVM sequence and/or chimeric intron). In certain embodiments, the expression constructs comprise in 5' to 3' orientation, an enhancer sequence, a promoter sequence, an intronic sequence, a transgene (optionally comprising a signal peptide), and a polyadenylation signal.

The expression cassette may be included in any viral or non-viral vector, including but not limited to plasmid vectors, adenovirus vector, retroviral vectors and adeno associated vector (AAV). In a preferred embodiment, the expression construct is carried on an AAV construct and further comprises 5' and 3' ITRs flanking the expression constructs as described herein. Optionally, insulator (spacer) molecules are also included between one or more of the components of the expression construct, for example, between the 5' ITR and the enhancer and/or between the polyadenylation signal and the 3' ITR. In some embodiments, the insulator (spacer) regions comprise homology arms to facilitate targeted integration. In certain embodiments, the construct is a construct as shown in any of FIG. 1, 2, 4, 6, 7, 10, 19, 20 or 25. Two exemplary constructs are shown in SEQ ID NO:34 and in SEQ ID NO:37. It will be apparent that the individual components (promoter, insulator(s), enhancer, transgene) can be combined in any combination with other components as described herein.

In any of the polynucleotides describes herein, the enhancer may be derived from a Serpin-1 enhancer. In certain embodiments, the enhancer is a wild-type sequence. In other embodiments, the enhancer comprises one or more modifications as compared to wild-type, for example a Serpin1 enhancer containing one or more nucleotide modifications as shown in FIG. 5, modifications of nucleotides at one or more of residues 1, 5, 14, 32 and/or 39 of the sequence shown in any of SEQ ID NOs:1-13. In certain embodiments, the Serpin1 enhancer comprises modifications at positions 1, 5, 14 and 32 of any of SEQ ID NOs:1-13 while in other embodiments, the Serpin1 enhancer comprises modification at positions 1, 14, 32 and 39 or any of SEQ ID NOs:1-13. Exemplary enhancer sequences are shown in SEQ ID NO:35 and 36. In some embodiments, the polynucleotides described herein comprise 1, 2, 3, 4, 5 or more enhancer elements. In certain embodiments, the 1, 2, 3, 4, 5 or more enhancer elements are identical wherein other embodiments, more than one type of enhancer element is used.

Any of the polynucleotides described herein may further optionally comprise an intronic sequence. In certain embodiments, the expression construct include a chimeric intron sequence, for example as shown in the bottom panels of FIGS. 6 and 7. The T-chimeric intron is a truncated version of the chimeric intron in pCI-neo (GenBank U47120). The chimeric intron in pCI-neo is the 5' splice donor site from the human β-globin gene, and the branchpoint and 3' acceptor site of an immunoglobulin gene heavy chain variable region. The T-chimeric intron contains a 45 bp deletion between the 5' splice donor and the branchpoint. In yet other embodiments, the expression constructs include a mutated MVM intron sequence (e.g., one or more of the mutations shown in FIGS. 12, 13 and 14 (SEQ ID NOs:15-17). Alternatively, the expression constructs as described herein may lack an intronic sequence, for example as shown in the constructs depicted in the middle panels of FIGS. 6, 7, 19 and 20.

The expression constructs of the invention also may include optimized insulator sequences between the AAV ITRs and the expression cassette. In certain embodiments, the expression construct comprises insulator (spacer) regions (e.g. Ins1 and Ins3, SEQ ID NOs 15 or 28 and SEQ ID NOs: 17 or 30, (respectively), and Ins2 (SEQ ID NOs:16 or 29). In certain embodiments, the expression construct comprises Ins4 (SEQ ID NO:38). Any of the insulator sequences may be used in either the 5' or 3' location, and any combination of the insulator sequences may be used within an expression construct. Particularly preferred are combinations of Ins1 at the 5' location and Ins3 at the 3' location.

The expression constructs as described herein also include and express one or more transgenes. Any transgene(s) can be expressed using the polynucleotides described herein, including, but not limited to, transgenes encoding functional versions of proteins lacking or deficient in any genetic disease, including but not limited to, lysosomal storage disorders (e.g., Gaucher's, Fabry's, Hunter's, Hurler's, Neimann-Pick's, Phenylketonuria (PKU) etc.), metabolic disorders, and/or blood disorders such as hemophilias and hemoglobinopathies, etc. See, e.g., U.S. Publication No. 20140017212 and 20140093913; U.S. Pat. Nos. 9,255,250 and 9,175,280. Non-limiting examples of proteins that may be expressed as described herein include fibrinogen, prothrombin, tissue factor, Factor V, Factor VII, Factor VIII, Factor IX, Factor X, Factor XI, Factor XII (Hageman factor), Factor XIII (fibrin-stabilizing factor), von Willebrand factor, prekallikrein, high molecular weight kininogen (Fitzgerald factor), fibronectin, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, plasminogen activator inhibitor-2, glucocerebrosidase (GBA), α-galactosidase A (GLA), iduronate sulfatase (IDS), iduronidase (IDUA), acid sphingomyelinase (SMPD1), MMAA, MMAB, MMACHC, MMADHC (C2orf25), MTRR, LMBRD1, MTR, propionyl-CoA carboxylase (PCC) (PCCA and/or PCCB subunits), a glucose-6-phosphate transporter (G6PT) protein or glucose-6-phosphatase (G6Pase), an LDL receptor (LDLR), ApoB, LDLRAP-1, a PCSK9, a mitochondrial protein such as NAGS (N-acetylglutamate synthetase), CPS1 (carbamoyl phosphate synthetase I), and OTC (ornithine transcarbamylase), ASS (argininosuccinic acid synthetase), ASL (argininosuccinase acid lyase) and/or ARG1 (arginase), and/or a solute carrier family 25 (SLC25A13, an aspartate/glutamate carrier) protein, a UGT1A1 or UDP glucuronsyltransferase polypeptide A1, a fumarylacetoacetate hydrolyase (FAH), an alanine-glyoxylate aminotransferase (AGXT) protein, a glyoxylate reductase/hydroxypyruvate reductase (GRHPR) protein, a transthyretin gene (TTR) protein, an ATP7B protein, a phenylalanine hydroxylase (PAH) protein, a lipoprotein lyase (LPL) protein, an engineered nuclease, an engineered transcription factor and/or an engineered single chain variable fragment antibody (diabody, camelid, etc.). In one preferred embodiment, the transgene encodes a FVIII polypeptide. In some embodiments, the FVIII polypeptide comprises a deletion of the B domain.

In some embodiments, the one or more transgenes include sequences encoding engineered nucleases (e.g. ZFNs, TALENs, TtAgo and CRISPR/Cas systems). In other embodiments, the transgenes include sequences encoding engineered transcription factors (e.g. ZFP-TFs, TALE-TFs, CRISPR/Cas-TF systems). The transgenes may also include sequences encoding a single chain antibody specific for a target of interest. In addition, the transgene may include sequences encoding a structural RNA (e.g. RNAi, shRNA, miRNA).

In certain aspects, the polynucleotides as described herein are introduced into a cell such that they are maintained episomally while driving expression of the transgene. In other aspects, the expression constructs are randomly integrated into the genome of the cell into which they are introduced. In further aspects the expression constructs driving transgene expression are integrated into a genome by nuclease-mediated targeted integration.

In further aspects, described herein are methods for expressing one or more transgenes in a liver cell, the methods comprising introducing one or more expression constructs as described herein into the cell such that the transgene is expressed in the cell. In certain embodiments, the expression construct is carried on a viral or non-viral vector, preferably an AAV vector (for example AAV2 or AAV2/6).

In another aspect, provided herein is a method of expressing one or more transgenes in a live animal, the methods comprising administering one or more expression cassettes as described herein to the live animal. In certain embodiments, the expression cassettes are administered to the liver of the live animal. In certain embodiments, the expression construct is carried on a viral or non-viral vector, preferably an AAV vector (for example AAV2, AAV2/6 or AAV2/8).

In some embodiments, provided herein are methods and compositions to express therapeutically relevant levels of one or more therapeutic proteins from one or more transgenes. In certain embodiments, expression of a transgene construct encoding a replacement protein results in 1% of normal levels of the protein produced, while in others, 2%, 3%, 4%, 5%, 10%, 15%, 20%, 30%, 50%, 80%, 100%, 150%, 200%, or more of normal levels of the protein are produced. In some preferred embodiments, the transgene encodes a FVIII protein and a therapeutically relevant amount of the protein is produced. In some embodiments, as a result of the use of the methods and compositions of the invention, a human patient has an increased amount of a therapeutic protein in their blood that results in a decrease in clinical symptoms. In certain aspects, the production of the therapeutic protein by the methods and compositions described herein in a human patient results in a decreased clotting time following injury as compared to a patient that has not been treated or compared to the patient prior to treatment. In some aspects, a human patient treated with the methods and compositions of the invention requires a decreased amount of replacement therapy than a patient who has not been treated or compared to the patient prior to treatment.

In some embodiments, the method and compositions of the invention as described herein can be used to induce tolerance in a mammal to a therapeutic protein such that the levels of the therapeutic protein encoded by the transgene remain at therapeutically relevant levels following a transient rise in anti-therapeutic protein antibodies. Thus, provided herein is a method of inducing tolerance to a therapeutic protein in a subject, the method comprising genetically modifying a cell in a subject using the method as described herein (e.g., so that the cell produces the therapeutic protein), optionally treating the subject with additional compositions (e.g., steroids and/or B-cell inhibitors) such that the animal becomes tolerized to the therapeutic protein. In some embodiments, insertion (integration) of the therapeutic protein into the recipient cells is done at the same time as treatment with an immune-inhibitory steroid or B-cell inhibitor, whereas in other instances, no immunomodulatory substances are administered to the animal. In some instances, the immunomodulatory agent is administered only if anti-therapeutic protein antibodies are generated. In further instances, the immunomodulatory agent is discontinued after a period of time.

In another aspect, pharmaceutical compositions comprising one or more of the cells, expression constructs and/or optional nucleases described herein are provided.

In certain aspects, described herein are methods and systems for targeted integration of a liver-specific expression cassette. The methods and systems comprise administering one or more expression cassettes as described herein and administering one or more nucleases specific for a target gene to a cell. Following nuclease-mediated cleavage of the target gene, the expression cassette is integrated into the gene via homology-dependent or homology-independent mechanisms. In certain embodiments, the target gene is an endogenous albumin gene.

For nuclease-mediated targeted integration of the expression constructs of the present invention, any nuclease can be used, including but not limited to, one or more zinc finger nucleases (ZFNs), TALENs, CRISPR/Cas nucleases and/or TtAgo nucleases, such that the expression construct is integrated into the region (gene) cleaved by the nuclease(s). In certain embodiments, one or more pairs of nucleases are employed. The nucleases may be introduced in mRNA form or may be administered to the cell using non-viral or viral vectors. In some aspects, the nuclease polynucleotides may be delivered by lentivirus or by non-integrating lentivirus. In other aspects, the expression cassette may be delivered by AAV and/or DNA oligos.

In another aspect, provided herein are methods for providing one or more functional proteins lacking or deficient in a mammal, or in a primate, such as a human primate, such as a human patient with a disease (e.g., a metabolic disease, a lysosomal storage disease (LSD), a hemoglobinopathy and/or a hemophilia), for example for treating the disease by supplying the protein(s) lacking or deficient in the subject. In another aspect, provided herein are methods for providing a functional protein for treating a disorder in which the protein is lacking, deficient or aberrantly expressed. In further embodiments, the methods comprise administering an expression cassette encoding a therapeutic protein useful for preventing or treating a disorder. In a further aspect, methods are described herein for providing a therapeutic protein for treating a disorder where the therapeutic protein is a single chain antibody. In certain embodiments, the methods comprise administering an expression cassette (e.g., AAV vector) as described herein to the liver of a subject in need thereof. In other embodiments, the method comprises administering a modified cell (expressing a functional version of a protein that is aberrantly expressed in a subject from an expression cassette as described) to the subject. Thus, an isolated cell may be introduced into the subject (ex vivo cell therapy) or a cell may be modified when it is part of the subject (in vivo).

In any of the compositions and methods described, expression cassettes and/or nucleases may be carried on an AAV vector, including but not limited to AAV1, AAV3, AAV4, AAV5, AAV6, AAV8, AAV9 and AAVrh10 or pseudotyped AAV such as AAV2/8, AAV8.2, AAV2/5 and AAV2/6 and the like. In certain embodiments, the polynucleotides (expression constructs and/or nucleases) are delivered using the same AAV vector types. In other embodiments, the polynucleotides are delivered using different AAV vector types. The polynucleotides may be delivered using one or more vectors. In certain embodiments, the polynucleotides are delivered via intravenous (e.g., intraportal vein) administration into the liver of an intact animal. In other embodiments, the polynucleotides are delivered via intravenous administration in a peripheral vein.

In any of the compositions and methods described herein, the protein encoded by the transgene may comprise a F8 protein, for example a B-Domain Deleted Factor VIII (BDD-F8). In other embodiments, the protein encoded by the transgene comprises a Factor IX protein. In other embodiments, the protein encoded by the transgene comprises a Factor VII protein. In other embodiments, the protein encoded by the transgene comprises a Factor X protein. In some embodiments, the protein encoded by the transgene comprises a glucocerebrosidase. In other embodiments, the protein encoded by the transgene comprises an a galactosidase. In further embodiments, the protein encoded by the transgene comprises an iduronate-2-sulfatase. In some embodiments, the protein encoded by the transgene comprises an alpha-L iduronidase. In further embodiments, the protein encoded by the transgene comprises sphingomyelin phosphodiesterase. In some embodiments, the transgene encodes a single chain antibody. In other embodiments, the transgene encodes a structural RNA. In any of the compositions or methods described herein, the transgene also comprises a transcriptional regulator while in others, it does not and transcription is regulated by an endogenous regulator. In another aspect, the methods of the invention comprise a composition for therapeutic treatment of a subject in need thereof. In some embodiments, the composition comprises engineered stem cells comprising a safe harbor specific nuclease, and a transgene encoding Factor VII, F8, F.IX, Factor X, GBA, GLA, IDS, IDUA, single chain antibody and/or SMPD1 protein or a functional fragment and/or truncation thereof. In other embodiments, the composition comprises engineered stem cells that have been modified and express a transgene encoding Factor VII, F8, F.IX, Factor X, GBA, GLA, IDS, IDUA, single chain antibody and/or SMPD1 protein or a functional fragment and/or truncation thereof.

The methods described herein can be practiced in vitro, ex vivo or in vivo. In certain embodiments, the compositions are introduced into a live, intact mammal. The mammal may be at any stage of development at the time of delivery, e.g., embryonic, fetal, neonatal, infantile, juvenile or adult. Additionally, targeted cells may be healthy or diseased. In certain embodiments, one or more of the compositions are delivered intravenously (e.g., to the liver via the intraportal vein, for example tail vein injection), intra-arterially, intraperitoneally, intramuscularly, into liver parenchyma (e.g., via injection), into the hepatic artery (e.g., via injection), and/or through the biliary tree (e.g., via injection).

For targeting the compositions to a particular type of cell, e.g., platelets, fibroblasts, hepatocytes, etc., one or more of the administered compositions may be associated with a homing agent that binds specifically to a surface receptor of the cell. For example, the vector may be conjugated to a ligand (e.g., galactose) for which certain hepatic system cells have receptors. The conjugation may be covalent, e.g., a crosslinking agent such as glutaraldehyde, or noncovalent, e.g., the binding of an avidinated ligand to a biotinylated vector. Another form of covalent conjugation is provided by engineering the AAV helper plasmid used to prepare the vector stock so that one or more of the encoded coat proteins is a hybrid of a native AAV coat protein and a peptide or protein ligand, such that the ligand is exposed on the surface of the viral particle.

A kit, comprising one or more of the expression constructs, AAV vectors, cell and/or pharmaceutical compositions described herein, is also provided. The kit may further comprise nucleic acids encoding nucleases, (e.g. RNA molecules encoding ZFNs, TALENs or Cas and modified Cas proteins, and guide RNAs), or aliquots of the nuclease proteins, cells, instructions for performing the methods of the invention, and the like.

These and other aspects will be readily apparent to the skilled artisan in light of disclosure as a whole.

BRIEF DESCRIPTION OF THE DRAWINGS

FIG. 8A shows secreted hFVIII-BDD levels on day 7 after administration and FIG. 8B shows secreted hFVIII-BDD levels over the duration of the 28-day study. The left y-axis of each graph shows ng/mL and the right y-axis shows the percent normal where, 1U=100% normal=200 ng/mL. *** denotes p>0.001, * denotes p>0.05. Each individual shape within the groupings represents the results from a single animal.

FIG. 9A shows human factor VIII-BDD (hFVIII) mRNA levels as analyzed from the indicated tissues (brain, heart, kidney, lung, liver, spleen, testes). As shown, hFVIII-BDD mRNA was only detected in liver and no other tissues from either the parent F8-BDD cDNA construct (open symbols) or CRMSBS2 no intron (filled symbols). FIG. 9B shows vector genome (VG) biodistribution from the same tissues depicted in FIG. 9A. Serotype AAV2/6 primarily transduces liver.

FIG. 14 (SEQ ID NO:17) shows an overview of the changes made to the wild-type MVM intron in the SBR Intron 3 used in constructs as described herein. Changes are boxed in grey and include: mutation of the G-rich intronic enhancer sequence, IES ko; minor mutation to potential branch point acceptor 1 (PBPA1); mutated acceptor site 1 poly-pyrimidine tract, A1PPT (−); mutated acceptor site 1, A1(−); strengthened acceptor site 2 poly-pyrimidine tract, A2PPT(+, 9T) by addition of more thymidines (T); Improved acceptor site 2, A2(+)

FIG. 15 has graphs depicting levels of secreted human Factor VIII (hFVIII) B-domain deleted from mice, represented as either ng/mL (left-y-axis) or percent normal (right y-axis), 1U=100% normal=200 ng/mL. C57BL/6 mice were transduced with 6E+12 vg/kg of AAV2/6 hFVIII constructs as denoted on the x-axis. FIG. 15A shows the secreted hFVIII levels on day 7. FIG. 15B shows the peak secreted hFVIII levels over the duration of the 28-day study. Numbers denote the mean hFVIII percent normal levels for the group.

FIG. 16A is a graph showing the mRNA values encoding Human factor VIII (hFVIII) that was analyzed from tissues (brain, heart, kidney, lung, liver, spleen, testes) in the study represented in FIG. 15. hFVIII mRNA was only detected in liver and no other tissues from either the parent F8 cDNA construct (open symbols) or CRMSBS2 SBR Intron 3 (filled symbols). FIG. 16B shows the vector genome (VG) biodistribution from the same tissues analyzed in FIG. 16A. Serotype AAV2/6 primarily transduces liver as previously published.

FIG. 17 has graphs depicting levels of enzymatically active secreted human Factor VIII (hFVIII) B-domain deleted from Hemophilia A R593C mice, represented as percent normal, 1U=100% normal. Hemophilia A knockout mice R593C were transduced with ~7E+12 vg/kg of AAV2/6 hFVIII-BDD construct as denoted on the x-axis. FIG. 17A shows the secreted hFVIII activity levels on day 14. FIG. 17B shows the secreted hFVIII activity levels on day 42. Numbers denote the mean hFVIII percent normal levels for the group.

FIG. 25A is a schematic of the donor, which is also shown in FIG. 10. FIG. 25B shows the amount of hFVIII-BDD detectable in the plasma, expressed both as ng/mL and percent normal (in normal human plasma). Male C57BL/6 mice were intravenously injected with 1.8E+11 vg/mouse (~7E+12 vg/kg) of AAV2/6 CRMSBS2 SBR Intron 3 cDNA (n=8). Shown are mean peak levels of hFVIII-BDD in the plasma of C57BL/6 mice as measured by hFVIII ELISA.

FIGS. 26A and 26B show the dosing scheme with for the human FVIII-BDD in various non-human primate (NHP) studies, including studies with removal of all immunosuppression at Day 103. FIG. 26A shows an overview of Rituxan and Solu-Medrol dosing. Rituxan (10 mg/kg; IV) dosing was pre-test article administration while methylprednisolone (Solu-Medrol) (10 mg/kg; IM) dosing was daily up until Day 103. FIG. 26B shows dosing schemes for experiments with pre- and post-test article addition and also shows the timing of Rituxan and Solu-Medrol dosing. Groups 1-5 followed an immunosuppression regimen of pre-test article injection, whereas Groups 6-8 followed an immunosuppression regimen of post-test article injection. The duration of this study was 56 days.

FIG. 27 shows individual animals for the formulation control group (Group 1, animal IDs 1101-1102), and the 6E+12 vg/kg dose group (Group 3, animal IDs 3101-3103). At day 14 following test article addition, circulating levels and activity of hFVIII were analyzed by ELISA or APTT clotting activity. Normal levels of Cynomolgus monkey FVIII are ~1U/mL (~100% normal) reflected in the clotting activity data for the formulation control group as the clotting activity assay is not specific for human FVIII. The ELISA is specific for human FVIII over Cynomolgus monkey FVIII thus, as expected there is no hFVIII levels as measured by ELISA in the formulation control group. In the Group 3 animals there are supraphysiological levels and activity of circulating hFVIII, upwards of 8U/mL (800% normal).

FIGS. 28A and 28B are graphs showing liver enzyme profiles in NHP treated with the AAV hF8 cDNA. Cynomolgus monkeys were administered formulation buffer or 6E+12 vg/kg of AAV2/6 hF8 cDNA (parent vector). Shown are representative liver enzyme profiles in animals for the formulation control group (Group 1, animal ID 1101), and the 6E+12 vg/kg dose group (Group 3, animal ID 3102) as an indicator of liver condition. Shown are alanine aminotransferase (ALT) and aspartate aminotransferase (AST). The acceptable upper limit reference values to still be in a normal range for Cynomlogus monkeys for ALT is 126 U/L and 120 U/L for AST. For both the formulation control group and the 6E+12 vg/kg AAV hF8 cDNA (parent vector) group ALT/AST levels were elevated post-liver biopsy (liver biopsy was on day 41), denoted by an asterisk. Otherwise AAV hF8 cDNA was well-tolerated over the entirety of the study (247 days).

FIG. 29A shows results for Group 2 animals (AAV2/6, 2E+12 vg/kg); FIG. 29B shows results for Group 3 animals (AAV2/6, 6E+12 vg/kg); FIG. 29C shows results for Group 4 animals (AAV2/8, 6E+12 vg/kg); and FIG. 29D shows results for Group 5 animals (AAV2/8, 6E+12 vg/kg). 1U/mL of human factor VIII is considered physiological normal, and thus equals 100% of normal physiological circulating human factor VIII.

FIG. 31A shows animal 2101; FIG. 31B shows animal 2102; and FIG. 31C shows animal 2103.

FIG. 32A shows animal 3101; FIG. 32B shows animal 3102; and FIG. 32C shows animal 3103.

FIG. 33D is a 'blow up' of the lower values in the graph for animal 4103 (note that the y axis in FIGS. 33A-33C goes from 0-5 U/mL of FVIII antigen while FIG. 33D goes from 0-1 U/mL of FVIII antigen). The dotted horizontal line represents the Bethesda Unit cutoff point, below which values would not be considered positive for anti-FVIII neutralizing antibodies. The Solu-Medrol was stopped at day 103-indicated by the vertical dashed line. Each graph shows the results for a single monkey: FIG. 33A shows animal 4101; FIG. 33B shows animal 4102; FIGS. 33C and 33D shows animal 4103.

FIGS. 34A through 34E are graphs depicting the results from individual cynomolgus monkeys (n=3) dosed with the high dose (6E+12 vg/kg, Group 5) of AAV2/8-FVIII-BDD cDNA over a time period of 168 days post dosing. In FIGS. 34A-34C, concentrations of FVIII-BDD in the plasma, as measured through ELISA, are shown in black. Additionally, concentrations of neutralizing anti-FVIII antibody (shown as Bethesda Units) in plasma are shown in grey. FIGS. 34D and 34E are 'blow ups' of the lower values in the graph (note that the y axis in 34A-C goes from 0-5 U/mL of FVIII antigen while the axis for 34D and 34E goes from 0-1 U/mL of FVIII antigen). The dotted horizontal line represents the Bethesda Unit cutoff point, below which values would not be considered positive for anti-FVIII neutralizing antibodies. The Solu-Medrol was stopped at day 103-indicated by the vertical dashed line. Each graph shows the results for a single monkey (animal 5101: FIG. 34A, 5102: FIG. 34B and 5103: FIG. 34C).

As shown in FIG. 35A, the BU reached ~0.9 BU/mL following the Xyntha® challenge, indicated by the grey area of the graph. Animal ID 3103 had high BU levels, upwards of 3U/mL for numerous weeks, and the added hFVIII biologic challenge (indicated by the dashed vertical lines) did not induce additional detectable inhibitory antibodies (BU) (FIG. 35B). In all groups that received AAV hF8 cDNA, and had sustained hFVIII levels there no increase in inhibitory antibodies, BU (FIGS. 35C through F, indicated by grey arrows). FIG. 35C shows that the hFVIII levels for animal ID 3101 were durable for 19 weeks at ~150% of normal hFVIII, while FIG. 35D shows that the hFVIII levels for animal ID 4103 were durable for 19 weeks at ~10% of normal hFVIII. FIG. 35E shows that the hFVIII levels for animal ID 5101 were durable for 19 weeks at ~15% of normal hFVIII, while in FIG. 35F, hFVIII levels for animal ID 5102 were durable for 19 weeks at ~35% of normal hFVIII. The dotted horizontal line represents the Bethesda Unit cutpoint, below which values would not be considered positive for anti-FVIII neutralizing antibodies. The vertical dotted line represents removal of Solu-Medrol at Day 103 post-test article dosing in FIGS. 35B, 35E and 35F.

FIG. 36A is a graph showing hFVIII-BDD detected in HepG2 cellular supernatant over time (t=days) following administration of albumin-targeted ZFNs (SBS #47171/47898, AAV2/6-ZFN) and a hFVIII-BDD cDNA AAV2/6-FVIII-BDD (CRMSBS2 No Intron) to HepG2 cellsAAV2/6-FVIII-BDD administered at 3.0E+04, 6.0E+04 and 1.2E+05 together with AAV2/6-ZFN 3.0E+05. FIG. 36B is a graph showing hFVIII cDNA alone (no ZFN). Data shown are of n=3 biological replicates. Error bars represent the standard error of the mean of replicates Dotted line is the limit of detection of the hFVIII ELISA.

FIGS. 40A and 40B are graphs showing in vitro production and detection of hVIII from the endogenous albumin locus. FIG. 40A shows total levels of hFVIII detected in HepG2 cellular supernatant following administration of albumin-targeted ZFNs (SBS #42906/43043) and a hFVIII cDNA (CRMSBS2 SBR Intron 3) to HepG2 cells (assayed at Day 19). In this example the hFVIII cDNA was used at increasing doses from 3.0E+04, 6.0E+04 and 1.2E+05 together with ZFN 3.0E+05. Also shown are hFVIII cDNA with GFP (no ZFN) to control for total virus added to the cells, and hFVIII cDNA alone (no ZFN), both of the latter demonstrating little to no detectable secreted hFVIII. This is because the episomal hFVIII is degraded prior to build up of sufficient amounts of detectable secreted hFVIII. Data shown are of n=2 biological replicates. Error bars represent the standard error of the mean of technical and biological replicates. Dotted line is the limit of detection of the hFVIII ELISA. FIG. 40B shows levels of endogenous albumin-hFVIII target integration by NHEJ using quantitative PCR. The 5' primer is located within the endogenous human albumin locus, the probe is located within the ITR of the hFVIII cassette and the 3' primer within the hFVIII.

DETAILED DESCRIPTION

Figure 1:
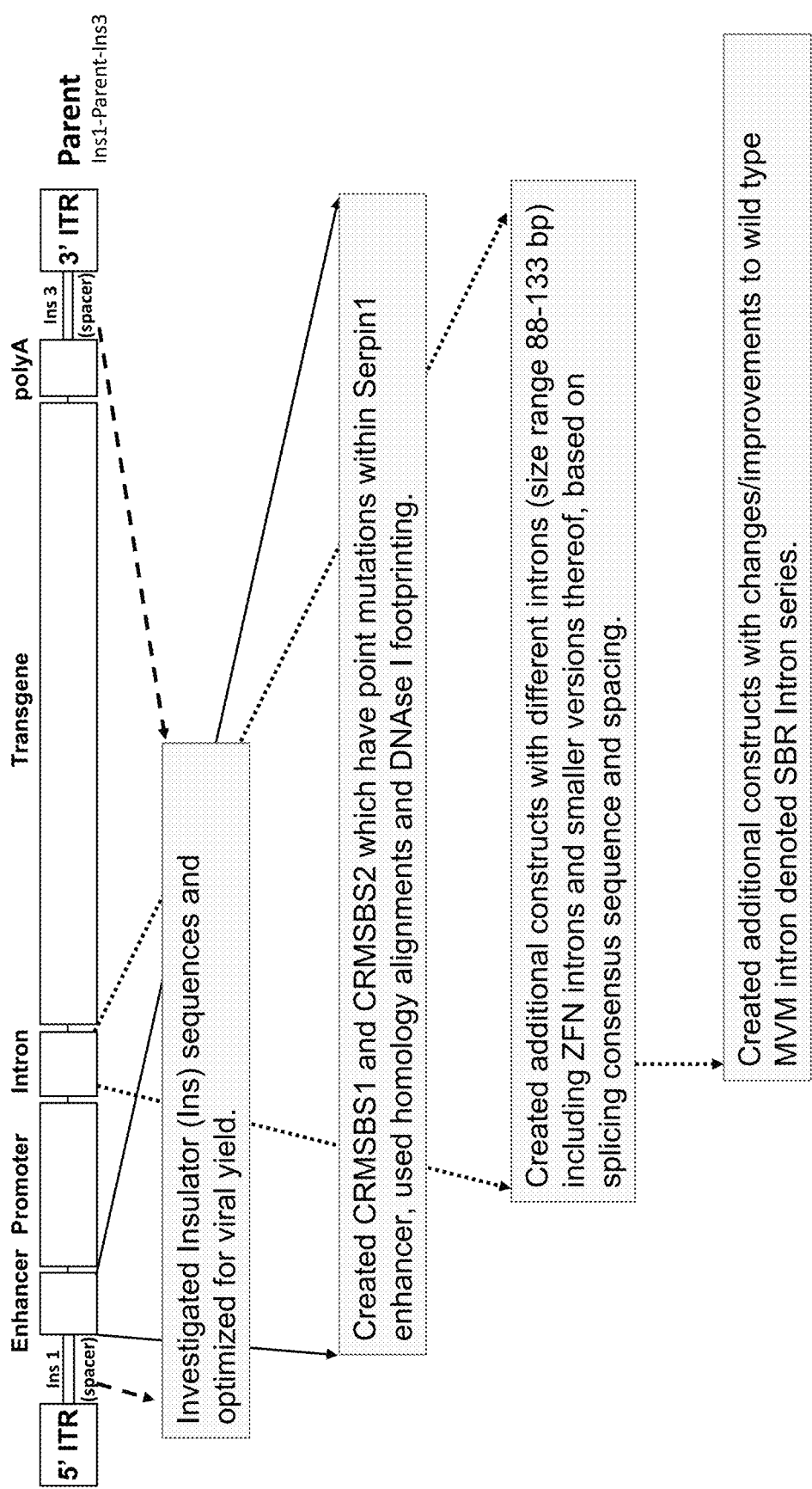
FIG. 1 is a schematic showing transgene cassette elements, and the steps taken to identify improved enhancers and introns.

Disclosed herein are expression cassettes for expression of a transgene, particularly in liver cells. The constructs can be used to deliver any transgene(s) to liver cells, in vivo or in vitro and can be used for the treatment and/or prevention of any disease or disorder which can be ameliorated by the provision of one or more of the transgenes. Unlike currently used hepatic-targeted constructs, the constructs described herein include modified enhancer and/or intronic sequences and, in addition, express the transgene at high levels even without the use of an MVM intron. These constructs are also small, allowing for successful use with transgenes delivered by small vector systems such as AAV.

The constructs described herein can be used to express hFVIII BDD in the liver of non-human primates. Depending on the initial dose of the AAV hF8 cDNA expression cassette, circulating plasma levels of hFVIII were upwards of 800% of normal circulating hFVIII. Following these initial high doses, many animals settled in to expression of 10-150% of normal levels for greater than eight weeks. In addition, some of the animals did not mount an anti-hFVIII antibody response upon challenge with injected hFVIII protein (Xyntha®), suggestive of the development of tolerance to the hFVIIII protein in these animals over the course of the experiment.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Recombination" refers to a process of exchange of genetic information between two polynucleotides, including but not limited to, capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms.

In certain methods of the disclosure, one or more targeted nucleases as described herein create a double-stranded break (DSB) in the target sequence (e.g., cellular chromatin) at a predetermined site (e.g., albumin gene). The DSB mediates integration of a construct as described herein. Optionally, the construct has homology to the nucleotide sequence in the region of the break. The expression construct may be physically integrated or, alternatively, the expression cassette is used as a template for repair of the break via homologous recombination, resulting in the introduction of all or part of the nucleotide sequence as in the expression cassette into the cellular chromatin. Thus, a first sequence in cellular chromatin can be altered and, in certain embodiments, can be converted into a sequence present in an expression cassette. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, the exogenous nucleotide sequence (the "expression construct" or "expression cassette" or "vector") can contain sequences that are homologous, but not identical, to genomic sequences in the region of interest, thereby stimulating homologous recombination to insert a non-identical sequence in the region of interest. Thus, in certain embodiments, portions of the expression cassette sequence that are homologous to sequences in the region of interest exhibit between about 80 to 99% (or any integer therebetween) sequence identity to the genomic sequence that is replaced. In other embodiments, the homology between the expression cassette and genomic sequence is higher than 99%, for example if only 1 nucleotide differs as between the homology regions of the expression cassette and genomic sequences of over 100 contiguous base pairs. In certain cases, a non-homologous portion of the expression cassette can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest.

The term "sequence" refers to a nucleotide sequence of any length, which can be DNA or RNA; can be linear, circular or branched and can be either single-stranded or double stranded. The term "transgene" refers to a nucleotide sequence that is inserted into a genome. A transgene can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes. The liver specific constructs described herein may be epiosomally maintained or, alternatively, may be stably integrated into the cell.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, ligases, deubiquitinases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™) Agrobacterium-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of fusion molecules include, but are not limited to, fusion proteins (for example, a fusion between a protein DNA-binding domain and a cleavage domain), fusions between a polynucleotide DNA-binding domain (e.g., sgRNA) operatively associated with a cleavage domain, and fusion nucleic acids (for example, a nucleic acid encoding the fusion protein).

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells), including stem cells (pluripotent and multipotent).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the B-domain deleted human Factor VIII is a functional fragment of the full-length Factor VIII protein.

A polynucleotide "vector" or "construct" is capable of transferring gene sequences to target cells. Typically, "vector construct," "expression vector," "expression construct," "expression cassette," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the expression cassettes of the invention can be administered. Subjects of the present invention include those with a disorder.

Liver-Specific Expression Constructs

Described herein are expression cassettes (constructs) for use in directing expression of a transgene in a liver cell, including in vivo following administration of the expression cassette(s) to the subject (e.g., hepatic delivery). The expression construct may be maintained episomally and drive expression of the transgene extrachromosomally or, alternatively, the expression construct may be integrated into the genome of a liver cell, for example by nuclease-mediated targeted integration.

The polynucleotide expression construct comprises an enhancer sequence, a promoter sequence, and one or more transgenes. Optionally included are one or more of the following: an intronic sequence, a polyadenylation sequence and/or a signal peptide. Any enhancer sequence may be used in the expression constructs described herein. In certain embodiments, the enhancer is a wild-type or modified Serpin1 enhancer (Chuah et al., (2014) *Molecular Therapy,* 22, 1605-1613, Nair et al., (2014) *Blood,* 123, 3195-3199)

Figure 5:
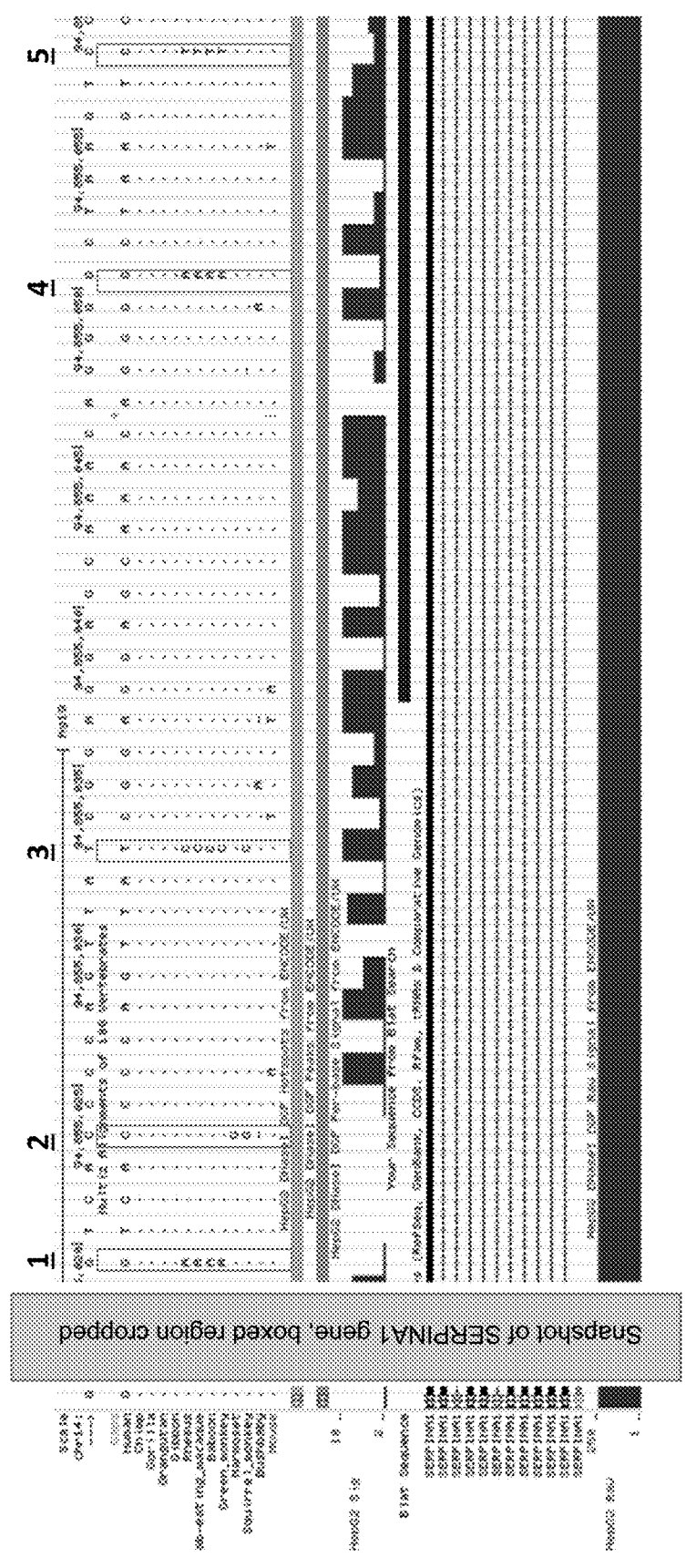
FIG. 5 (SEQ ID NO:1 to 13) shows an alignment of SERPINA1 gene from multiple species using ENCODE Alignment of multiple species of the SERPINA1 gene. Identical residues are not shown (denoted by "."). Boxed regions denoted 1 through 5 are the sites of modification to the sequence. Also shown by black bars in the middle panel are the regions of DNAse I sensitivity in HepG2 cells. CRMSBS1 includes changes at boxed positions 1, 2, 3, and 4 and CRMSBS2 includes changes at boxed positions 1, 3, 4, and 5. "CRM" refers to cis-regulatory module. "SBS1/2" refers to Sangamo Biosciences internal numeric references for the constructs 1 and 2. The light gray boxed region is sequences of the SERPINA1 gene that were omitted.

In preferred embodiments, the Serpin1 enhancer comprises one or more mutations (e.g., point mutations) as compared to wild-type, for example a Serpin1 enhancer containing one or more nucleotide modifications as shown in FIG. 5, namely modifications of nucleotides at one or more of residues 1, 5, 14, 32 and/or 39 of the sequence shown in any of SEQ ID NOs:1-13. In certain embodiments, the Serpin1 enhancer comprises modifications at positions 1, 5, 14 and 32 (constructs designated CRMSBS1) of any of SEQ ID NOs:1-13 while in other embodiments, the Serpin1 enhancer comprises modification at positions 1, 14, 32 and 39 (constructs designated CRMSBS2) or any of SEQ ID NOs:1-13. Exemplary enhancer sequences are shown below:

```
CRMSBS1 (SEQ ID NO: 35):
5'GGGGGAGGCTGCTGGTGAATATTAACCAAGATCAGCCCAGTTACCGGAG

GAGCAAACAGGGGCTAAGTTCAC

CRMSBS2 (SEQ ID NO: 36):
5'GGGGGAGGCTGCTGGTGAATATTAACCAAGATCACCCCAGTTACCGGAG

GAGCAAACAGGGACTAAGTTCAC
```

Similarly, any promoter sequence can be used in the expression cassettes of the invention. In certain embodiments, the promoter is a constitutive promoter. In other embodiments, the promoter is an inducible or tissue specific promoter. In some embodiments, the promoter is a liver-specific promoter. In certain embodiments, the promoter is a transthyretin minimal promoter (TTRm) promoter. In other embodiments, the promoter is an alpha-1 anti-trypsin (hAAT) promoter.

Figure 12:
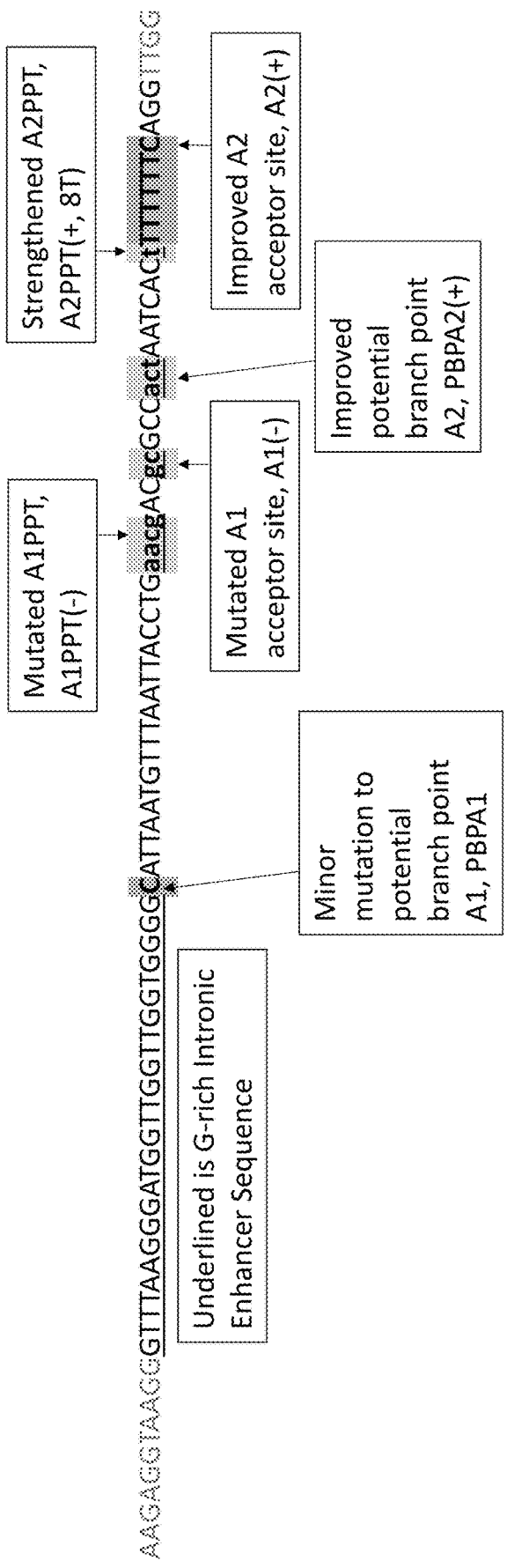
FIG. 12 (SEQ ID NO:15) shows an overview of the changes made to the wild-type MVM intron in SBR Intron 1 used in constructs described herein. Changes are boxed in grey and include: minor mutation to potential branch point acceptor 1 (PBPA1); mutated acceptor site 1 poly-pyrimidine tract, A1PPT (−); mutated acceptor site 1, A1(−); improved potential branch point acceptor site 2, PBPA2(+); strengthened acceptor site 2 poly-pyrimidine tract, A2PPT (+, 8T) by addition of more thymidines (T); Improved acceptor site 2, A2(+).
Figure 13:
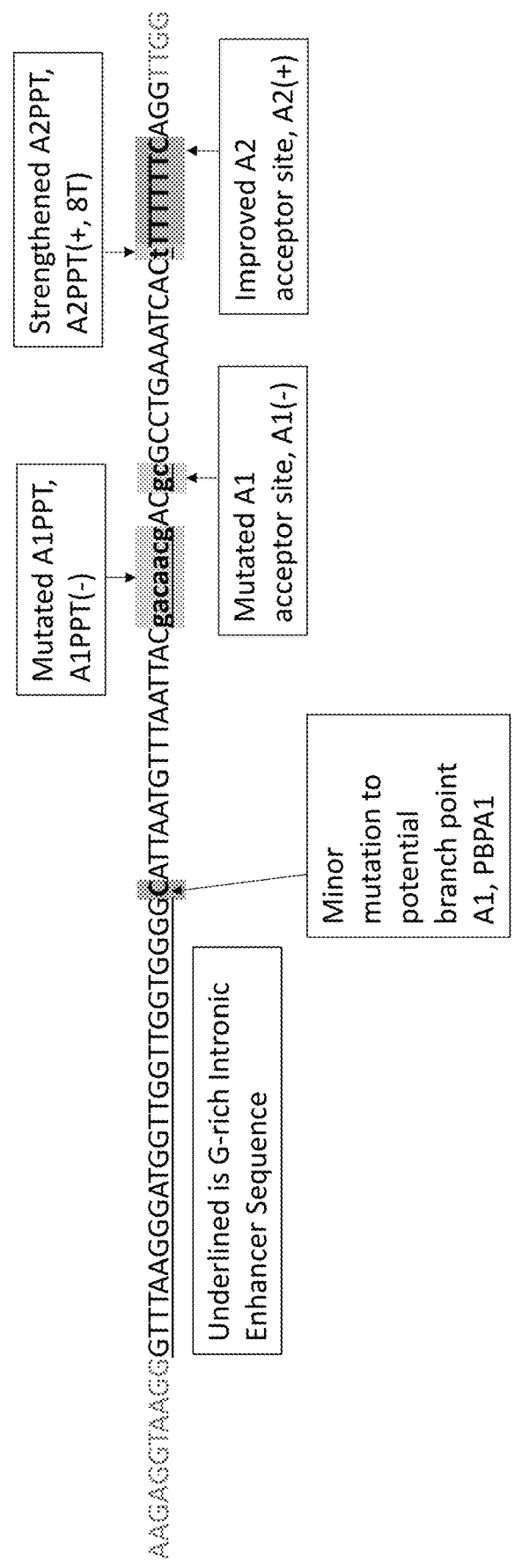
FIG. 13 (SEQ ID NO:16) shows an overview of the changes made to the wild-type MVM intron in the SBR Intron 2 used in constructs as described herein. Changes are boxed in grey and include: minor mutation to potential branch point acceptor 1 (PBPA1); mutated acceptor site 1 poly-pyrimidine tract, A1PPT (−); mutated acceptor site 1, A1(−); strengthened acceptor site 2 poly-pyrimidine tract, A2PPT(+, 8T) by addition of more thymidines (T); Improved acceptor site 2, A2(+).

Any of the polynucleotides described herein may further optionally comprise an intronic sequence. In certain embodiments, the expression construct includes a truncated chimeric intron (T-chimeric intron) sequence, for example as shown in the bottom panels of FIGS. 6, 7, 19 and 20. The T-chimeric intron is a truncated version of the chimeric intron in pCI-neo (GenBank U47120). The chimeric intron in pCI-neo is the 5' splice donor site from the human β-globin gene, and the branchpoint and 3' acceptor site of an immunoglobulin gene heavy chain variable region. The T-chimeric intron contains a 45 bp deletion between the 5' splice donor and the branchpoint. In yet other embodiments, the expression constructs include a mutated MVM intron sequence (e.g., one or more of the mutations shown in FIGS. 12, 13 and 14 (SEQ ID NOs:15-17).

Alternatively, the expression constructs as described herein may lack an intronic sequence, for example as shown in the constructs depicted in the middle panels of FIGS. 6, 7, 19 and 20. An exemplary construct, with annotations including a Factor VIII transgene is shown below and it will be apparent that the F8 transgene can be replaced with any transgene and that the promoter and insulator sequences may be further modified as described herein:

hF8 cDNA, no intron (complete sequence including promoter module, poly A and Ins, CRMSBS2 No intron) (SEQ ID NO:34):

Name: CRMSBS2 No Intron

| Module | Residues |
|---|---|
| Ins 1 | 14-32 |
| CRMSBS2 | 33-104 |
| TTRm | 117-339 |
| hF8_BDD | 345-4718 |
| SPA51 | 4725-4775 |
| Ins 3 | 4776-4792 |

```
GCGGCCTAAGCTTGGAACCATTGCCACCTTCAGGGGGAGGCTGCTGGTGA  -   50
ATATTAACCAAGATCACCCCAGTTACCGGAGGAGCAAACAGGGACTAAGT  -  100
TCACACGCGTGGTACCGTCTGTCTGCACATTTCGTAGAGCGAGTGTTCCG  -  150
ATACTCTAATCTCCCTAGGCAAGGTTCATATTTGTGTAGGTTACTTATTC  -  200
TCCTTTTGTTGACTAAGTCAATAATCAGAATCAGCAGGTTTGGAGTCAGC  -  250
TTGGCAGGGATCAGCAGCCTGGGTTGGAAGGAGGGGGTATAAAAGCCCCT  -  300
TCACCAGGAGAAGCCGTCACACAGATCCACAAGCTCCTGCTAGTATGCAG  -  350
ATCGAGCTCTCCACCTGCTTCTTTCTGTGCCTGTTGAGATTCTGCTTCAG  -  400
CGCCACCAGGAGATACTACCTGGGGGCTGTGGAGCTGAGCTGGGACTACA  -  450
TGCAGTCTGACCTGGGGGAGCTGCCTGTGGATGCCAGGTTCCCCCCCAGA  -  500
GTGCCCAAGAGCTTCCCCTTCAACACCTCTGTGGTGTACAAGAAGACCCT  -  550
GTTTGTGGAGTTCACTGACCACCTGTTCAACATTGCCAAGCCCAGGCCCC  -  600
CCTGGATGGGCCTGCTGGGCCCCACCATCCAGGCTGAGGTGTATGACACT  -  650
GTGGTGATCACCCTGAAGAACATGGCCAGCCACCCTGTGAGCCTGCATGC  -  700
TGTGGGGGTGAGCTACTGGAAGGCCTCTGAGGGGGCTGAGTATGATGACC  -  750
AGACCAGCCAGAGGGAGAAGGAGGATGACAAGGTGTTCCCTGGGGGCAGC  -  800
CACACCTATGTGTGGCAGGTGCTGAAGGAGAATGGCCCCATGGCCTCTGA  -  850
CCCCCTGTGCCTGACCTACAGCTACCTGAGCCATGTGGACCTGGTGAAGG  -  900
ACCTGAACTCTGGCCTGATTGGGGCCCTGCTGGTGTGCAGGGAGGGCAGC  -  950
CTGGCCAAGGAGAAGACCCAGACCCTGCACAAGTTCATCCTGCTGTTTGC  - 1000
TGTGTTTGATGAGGGCAAGAGCTGGCACTCTGAAACCAAGAACAGCCTGA  - 1050
TGCAGGACAGGGATGCTGCCTCTGCCAGGGCCTGGCCCAAGATGCACACT  - 1100
GTGAATGGCTATGTGAACAGGAGCCTGCCTGGCCTGATTGGCTGCCACAG  - 1150
GAAGTCTGTGTACTGGCATGTGATTGGCATGGGCACCACCCCTGAGGTGC  - 1200
ACAGCATCTTCCTGGAGGGCCACACCTTCCTGGTCAGGAACCACAGGCAG  - 1250
GCCAGCCTGGAGATCAGCCCCATCACCTTCCTGACTGCCCAGACCCTGCT  - 1300
GATGGACCTGGGCCAGTTCCTGCTGTTCTGCCACATCAGCAGCCACCAGC  - 1350
ATGATGGCATGGAGGCCTATGTGAAGGTGGACAGCTGCCCTGAGGAGCCC  - 1400
CAGCTGAGGATGAAGAACAATGAGGAGGCTGAGGACTATGATGATGACCT  - 1450
GACTGACTCTGAGATGGATGTGGTGAGGTTTGATGATGACAACAGCCCCA  - 1500
GCTTCATCCAGATCAGGTCTGTGGCCAAGAAGCACCCCAAGACCTGGGTG  - 1550
CACTACATTGCTGCTGAGGAGGAGGACTGGGACTATGCCCCCCTGGTGCT  - 1600
GGCCCCTGATGACAGGAGCTACAAGAGCCAGTACCTGAACAATGGCCCCC  - 1650
AGAGGATTGGCAGGAAGTACAAGAAGGTCAGGTTCATGGCCTACACTGAT  - 1700
```

```
GAAACCTTCAAGACCAGGGAGGCCATCCAGCATGAGTCTGGCATCCTGGG  - 1750
CCCCCTGCTGTATGGGAGGTGGGGGACACCCTGCTGATCATCTTCAAGA  - 1800
ACCAGGCCAGCAGGCCCTACAACATCTACCCCCATGGCATCACTGATGTG  - 1850
AGGCCCCTGTACAGCAGGAGGCTGCCCAAGGGGTGAAGCACCTGAAGGA  - 1900
CTTCCCCATCCTGCCTGGGGAGATCTTCAAGTACAAGTGGACTGTGACTG  - 1950
TGGAGGATGGCCCCACCAAGTCTGACCCCAGGTGCCTGACCAGATACTAC  - 2000
AGCAGCTTTGTGAACATGGAGAGGGACCTGGCCTCTGGCCTGATTGGCCC  - 2050
```

```
1         10        20        30        40        50
|         |         |         |         |         |
CCTGCTGATCTGCTACAAGGAGTCTGTGGACCAGAGGGGCAACCAGATCA  - 2100
TGTCTGACAAGAGGAATGTGATCCTGTTCTCTGTGTTTGATGAGAACAGG  - 2150
AGCTGGTACCTGACTGAGAACATCCAGAGGTTCCTGCCCAACCCTGCTGG  - 2200
GGTGCAGCTGGAGGACCCTGAGTTCCAGGCCAGCAACATCATGCACAGCA  - 2250
TCAATGGCTATGTGTTTGACAGCCTGCAGCTGTCTGTGTGCCTGCATGAG  - 2300
GTGGCCTACTGGTACATCCTGAGCATTGGGGCCCAGACTGACTTCCTGTC  - 2350
TGTGTTCTTCTCTGGCTACACCTTCAAGCACAAGATGGTGTATGAGGACA  - 2400
CCCTGACCCTGTTCCCCTTCTCTGGGGAGACTGTGTTCATGAGCATGGAG  - 2450
AACCCTGGCCTGTGGATTCTGGGCTGCCACAACTCTGACTTCAGGAACAG  - 2500
GGGCATGACTGCCCTGCTGAAAGTCTCCAGCTGTGACAAGAACACTGGGG  - 2550
ACTACTATGAGGACAGCTATGAGGACATCTCTGCCTACCTGCTGAGCAAG  - 2600
AACAATGCCATTGAGCCCAGGAGCTTCAGCCAGAATCCACCCGTCCTTAA  - 2650
GCGCCATCAGCGCGAGATCACCAGGACCACCCTGCAGTCTGACCAGGAGG  - 2700
AGATTGACTATGATGACACCATCTCTGTGGAGATGAAGAAGGAGGACTTT  - 2750
GACATCTACGACGAGGACGAGAACCAGAGCCCCAGGAGCTTCCAGAAGAA  - 2800
GACCAGGCACTACTTCATTGCTGCTGTGGAGAGGCTGTGGGACTATGGCA  - 2850
TGAGCAGCAGCCCCCATGTGCTGAGGAACAGGGCCCAGTCTGGCTCTGTG  - 2900
CCCCAGTTCAAGAAGGTGGTGTTCCAGGAGTTCACTGATGGCAGCTTCAC  - 2950
CCAGCCCCTGTACAGAGGGGAGCTGAATGAGCACCTGGGCCTGCTGGGCC  - 3000
CCTACATCAGGGCTGAGGTGGAGGACAACATCATGGTGACCTTCAGGAAC  - 3050
CAGGCCAGCAGGCCCTACAGCTTCTACAGCAGCCTGATCAGCTATGAGGA  - 3100
GGACCAGAGGCAGGGGCTGAGCCCAGGAAGAACTTTGTGAAGCCCAATG  - 3150
AAACCAAGACCTACTTCTGGAAGGTGCAGCACCACATGGCCCCCACCAAG  - 3200
GATGAGTTTGACTGCAAGGCCTGGGCCTACTTCTCTGATGTGGACCTGGA  - 3250
GAAGGATGTGCACTCTGGCCTGATTGGCCCCCTGCTGGTGTGCCACACCA  - 3300
ACACCCTGAACCCTGCCCATGGCAGGCAGGTGACTGTGCAGGAGTTTGCC  - 3350
CTGTTCTTCACCATCTTTGATGAAACCAAGAGCTGGTACTTCACTGAGAA  - 3400
CATGGAGAGGAACTGCAGGGCCCCCTGCAACATCCAGATGGAGGACCCCA  - 3450
CCTTCAAGGAGAACTACAGGTTCCATGCCATCAATGGCTACATCATGGAC  - 3500
ACCCTGCCTGGCCTGGTGATGGCCCAGGACCAGAGGATCAGGTGGTACCT  - 3550
GCTGAGCATGGGCAGCAATGAGAACATCCACAGCATCCACTTCTCTGGCC  - 3600
ATGTGTTCACTGTGAGGAAGAAGGAGGAGTACAAGATGGCCCTGTACAAC  - 3650
CTGTACCCTGGGGTGTTTGAGACTGTGGAGATGCTGCCCAGCAAGGCTGG  - 3700
CATCTGGAGGGTGGAGTGCCTGATTGGGGAGCACCTGCATGCTGGCATGA  - 3750
GCACCCTGTTCCTGGTGTACAGCAACAAGTGCCAGACCCCCCTGGGCATG  - 3800
GCCTCTGGCCACATCAGGGACTTCCAGATCACTGCCTCTGGCCAGTATGG  - 3850
CCAGTGGGCCCCCAAGCTGGCCAGGCTGCACTACTCTGGCAGCATCAATG  - 3900
CCTGGAGCACCAAGGAGCCCTTCAGCTGGATCAAGGTGGACCTGCTGGCC  - 3950
CCCATGATCATCCATGGCATCAAGACCCAGGGGCCAGGCAGAAGTTCAG  - 4000
CAGCCTGTACATCAGCCAGTTCATCATCATGTACAGCCTGGATGGCAAGA  - 4050
AGTGGCAGACCTACAGGGGCAACAGCACTGGCACCCTGATGGTGTTCTTT  - 4100
GGCAATGTGGACAGCTCTGGCATCAAGCACAACATCTTCAACCCCCCCAT  - 4150
CATTGCCAGATACATCAGGCTGCACCCCACCCACTACAGCATCAGGAGCA  - 4200
CCCTGAGGATGGAGCTGATGGGCTGTGACCTGAACAGCTGCAGCATGCCC  - 4250
CTGGGCATGGAGAGCAAGGCCATCTCTGATGCCCAGATCACTGCCAGCAG  - 4300
CTACTTCACCAACATGTTTGCCACCTGGAGCCCCAGCAAGGCCAGGCTGC  - 4350
ATCTGCAGGGCAGGAGCAATGCCTGGAGGCCCCAGGTCAACAACCCCAAG  - 4400
GAGTGGCTGCAGGTGGACTTCCAGAAGACCATGAAGGTGACTGGGGTGAC  - 4450
CACCCAGGGGGTGAAGAGCCTGCTGACCAGCATGTATGTGAAGGAGTTCC  - 4500
TGATCAGCAGCAGCCAGGATGGCCACCAGTGGACCCTGTTCTTCCAGAAT  - 4550
GGCAAGGTGAAGGTGTTCCAGGGCAACCAGGACAGCTTCACCCCTGTGGT  - 4600
GAACAGCCTGGACCCCCCCCTGCTGACCAGATACCTGAGGATTCACCCCC  - 4650
AGAGCTGGGTGCACCAGATTGCCCTGAGGATGGAGGTGCTGGGCTGTGAG  - 4700
GCCCAGGACCTGTACTGAGGATCCAATAAAATATCTTTATTTTCATTACA  - 4750
```

```
1         10        20        30        40        50
|         |         |         |         |         |
TCTGTGTGTTGGTTTTTTGTGTGTTTTCCTGTAACGATCGGG**CTCGAGCG  - 4800
5'
```

Another exemplary construct, with annotations including a Factor VIII transgene is shown below and it will also be apparent that the F8 transgene can be replaced with any transgene and that the promoter and insulator sequences may be further modified as described herein:

hF8 cDNA, including intron (complete sequence including promoter module, poly A and Ins, CRMSBS2 SBR Intron 3) (SEQ ID NO:37):

```
Name: CRMSBS2 SBR Intron 3

Module          Residues

Ins 1           14-32
     CRMSBS2         33-104
     TTRm            117-339
     SBR Intron 3    340-432
     hF8 BDD         438-4811
     SPA51           4818-4868
     Ins 3           4869-4885
```

```
1         10        20        30        40        50
|         |         |         |         |         |
GCGGCCTAAGCTTGGAACCATTGCCACCTTCAGGGGGAGGCTGCTGGTGA -   50
ATATTAACCAAGATCACCCCAGTTACCGGAGGAGCAAACAGGGACTAAGT -  100
TCACACGCGTGGTACCGTCTGTCTGCACATTTCGTAGAGCGAGTGTTCCG -  150
ATACTCTAATCTCCCTAGGCAAGGTTCATATTTGTGTAGGTTACTTATTC -  200
TCCTTTTGTTGACTAAGTCAATAATCAGAATCAGCAGGTTTGGAGTCAGC -  250
TTGGCAGGGATCAGCAGCCTGGGTTGGAAGGAGGGGGTATAAAAGCCCCT -  300
TCACCAGGAGAAGCCGTCACACAGATCCACAAGCTCCTGAAGAGGTAAGG -  350
GTTTAAGTTATCGTTAGTTCGTGCACCATTAATGTTTAATTACCTGGAGC -  400
ACCTGCCTGAAATCATTTTTTTTTCAGGTTGGCTAGTATGCAGATCGAGC -  450
TCTCCACCTGCTTCTTTCTGTGCCTGTTGAGATTCTGCTTCAGCGCCACC -  500
AGGAGATACTACCTGGGGGCTGTGGAGCTGAGCTGGGACTACATGCAGTC -  550
TGACCTGGGGGAGCTGCCTGTGGATGCCAGGTTCCCCCCCAGAGTGCCCA -  600
AGAGCTTCCCCTTCAACACCTCTGTGGTGTACAAGAAGACCCTGTTTGTG -  650
GAGTTCACTGACCACCTGTTCAACATTGCCAAGCCCAGGCCCCCCTGGAT -  700
GGGCCTGCTGGGCCCCACCATCCAGGCTGAGGTGTATGACACTGTGGTGA -  750
TCACCCTGAAGAACATGGCCAGCCACCCTGTGAGCCTGCATGCTGTGGGG -  800
GTGAGCTACTGGAAGGCCTCTGAGGGGCTGAGTATGATGACCAGACCAG -  850
CCAGAGGGAGAAGGAGGATGACAAGGTGTTCCCTGGGGGCAGCCACACCT -  900
ATGTGTGGCAGGTGCTGAAGGAGAATGGCCCCATGGCCTCTGACCCCCTG -  950
TGCCTGACCTACAGCTACCTGAGCCATGTGGACCTGGTGAAGGACCTGAA - 1000
CTCTGGCCTGATTGGGCCCTGCTGGTGTGCAGGGAGGGCAGCCTGGCCA - 1050
AGGAGAAGACCCAGACCCTGCACAAGTTCATCCTGCTGTTTGCTGTGTTT - 1100
GATGAGGGCAAGAGCTGGCACTCTGAAACCAAGAACAGCCTGATGCAGGA - 1150
CAGGGATGCTGCCTCTGCCAGGGCCTGGCCCAAGATGCACACTGTGAATG - 1200
GCTATGTGAACAGGAGCCTGCCTGGCCTGATTGGCTGCCACAGGAAGTCT - 1250
GTGTACTGGCATGTGATTGGCATGGGCACCACCCCTGAGGTGCACAGCAT - 1300
CTTCCTGGAGGGCCACACCTTCCTGGTCAGGAACCACAGGCAGGCCAGCC - 1350
TGGAGATCAGCCCCATCACCTTCCTGACTGCCCAGACCCTGCTGATGGAC - 1400
CTGGGCCAGTTCCTGCTGTTCTGCCACATCAGCAGCCACCAGCATGATGG - 1450
CATGGAGGCCTATGTGAAGGTGGACAGCTGCCCTGAGGAGCCCCAGCTGA - 1500
GGATGAAGAACAATGAGGAGGCTGAGGACTATGATGATGACCTGACTGAC - 1550
TCTGAGATGGATGTGGTGAGGTTTGATGATGACAACAGCCCCAGCTTCAT - 1600
CCAGATCAGGTCTGTGGCCAAGAAGCACCCCAAGACCTGGGTGCACTACA - 1650
TTGCTGCTGAGGAGGAGGACTGGGACTATGCCCCCCTGGTGCTGGCCCCT - 1700
GATGACAGGAGCTACAAGAGCCAGTACCTGAACAATGGCCCCCAGAGGAT - 1750
TGGCAGGAAGTACAAGAAGGTCAGGTTCATGGCCTACACTGATGAAACCT - 1800
TCAAGACCAGGGAGGCCATCCAGCATGAGTCTGGCATCCTGGGCCCCCTG - 1850
CTGTATGGGGAGGTGGGGACACCCTGCTGATCATCTTCAAGAACCAGGC - 1900
CAGCAGGCCCTACAACATCTACCCCCATGGCATCACTGATGTGAGGCCCC - 1950
```

```
1         10        20        30        40        50
|         |         |         |         |         |
TGTACAGCAGGAGGCTGCCCAAGGGGGTGAAGCACCTGAAGGACTTCCCC - 2000
ATCCTGCCTGGGGAGATCTTCAAGTACAAGTGGACTGTGACTGTGGAGGA - 2050
TGGCCCCACCAAGTCTGACCCCAGGTGCCTGACCAGATACTACAGCAGCT - 2100
TTGTGAACATGGAGAGGGACCTGGCCTCTGGCCTGATTGGCCCCCTGCTG - 2150
ATCTGCTACAAGGAGTCTGTGGACCAGAGGGGCAACCAGATCATGTCTGA - 2200
CAAGAGGAATGTGATCCTGTTCTCTGTGTTTGATGAGAACAGGAGCTGGT - 2250
ACCTGACTGAGAACATCCAGAGGTTCCTGCCCAACCCTGCTGGGGTGCAG - 2300
CTGGAGGACCCTGAGTTCCAGGCCAGCAACATCATGCACAGCATCAATGG - 2350
CTATGTGTTTGACAGCCTGCAGCTGTCTGTGTGCCTGCATGAGGTGGCCT - 2400
ACTGGTACATCCTGAGCATTGGGGCCCAGACTGACTTCCTGTCTGTGTTC - 2450
TTCTCTGGCTACACCTTCAAGCACAAGATGGTGTATGAGGACACCCTGAC - 2500
CCTGTTCCCCTTCTCTGGGGAGACTGTGTTCATGAGCATGGAGAACCCTG - 2550
GCCTGTGGATTCTGGGCTGCCACAACTCTGACTTCAGGAACAGGGGCATG - 2600
ACTGCCCTGCTGAAAGTCTCCAGCTGTGACAAGAACACTGGGGACTACTA - 2650
```

```
TGAGGACAGCTATGAGGACATCTCTGCCTACCTGCTGAGCAAGAACAATG   - 2700
CCATTGAGCCCAGGAGCTTCAGCCAGAATCCACCCGTCCTTAAGCGCCAT   - 2750
CAGCGCGAGATCACCAGGACCACCCTGCAGTCTGACCAGGAGGAGATTGA   - 2800
CTATGATGACACCATCTCTGTGGAGATGAAGAAGGAGGACTTTGACATCT   - 2850
ACGACGAGGACGAGAACCAGAGCCCCAGGAGCTTCCAGAAGAAGACCAGG   - 2900
CACTACTTCATTGCTGCTGTGGAGAGGCTGTGGGACTATGGCATGAGCAG   - 2950
CAGCCCCCATGTGCTGAGGAACAGGGCCCAGTCTGGCTCTGTGCCCCAGT   - 3000
TCAAGAAGGTGGTGTTCCAGGAGTTCACTGATGGCAGCTTCACCCAGCCC   - 3050
CTGTACAGAGGGGAGCTGAATGAGCACCTGGGCCTGCTGGGCCCCTACAT   - 3100
CAGGGCTGAGGTGGAGGACAACATCATGGTGACCTTCAGGAACCAGGCCA   - 3150
GCAGGCCCTACAGCTTCTACAGCAGCCTGATCAGCTATGAGGAGGACCAG   - 3200
AGGCAGGGGGCTGAGCCCAGGAAGAACTTTGTGAAGCCCAATGAAACCAA   - 3250
GACCTACTTCTGGAAGGTGCAGCACCACATGGCCCCCACCAAGGATGAGT   - 3300
TTGACTGCAAGGCCTGGGCCTACTTCTCTGATGTGGACCTGGAGAAGGAT   - 3350
GTGCACTCTGGCCTGATTGGCCCCCTGCTGGTGTGCCACACCAACACCCT   - 3400
GAACCCTGCCCATGGCAGGCAGGTGACTGTGCAGGAGTTTGCCCTGTTCT   - 3450
TCACCATCTTTGATGAAACCAAGAGCTGGTACTTCACTGAGAACATGGAG   - 3500
AGGAACTGCAGGGCCCCCTGCAACATCCAGATGGAGGACCCCACCTTCAA   - 3550
GGAGAACTACAGGTTCCATGCCATCAATGGCTACATCATGGACACCCTGC   - 3600
CTGGCCTGGTGATGGCCCAGGACCAGAGGATCAGGTGGTACCTGCTGAGC   - 3650
ATGGGCAGCAATGAGAACATCCACAGCATCCACTTCTCTGGCCATGTGTT   - 3700
CACTGTGAGGAAGAAGGAGGAGTACAAGATGCCCTGTACACCTGTACC    - 3750
CTGGGGTGTTTGAGACTGTGGAGATGCTGCCCAGCAAGGCTGGCATCTGG   - 3800
AGGGTGGAGTGCCTGATTGGGGAGCACCTGCATGCTGGCATGAGCACCCT   - 3850
GTTCCTGGTGTACAGCAACAAGTGCCAGACCCCCCTGGGCATGGCCTCTG   - 3900
GCCACATCAGGGACTTCCAGATCACTGCCTCTGGCCAGTATGGCCAGTGG   - 3950
GCCCCCAAGCTGGCCAGGCTGCACTACTCTGGCAGCATCAATGCCTGGAG   - 4000
CACCAAGGAGCCCTTCAGCTGGATCAAGGTGGACCTGCTGGCCCCCATGA   - 4050
TCATCCATGGCATCAAGACCCAGGGGGCCAGGCAGAAGTTCAGCAGCCTG   - 4100
TACATCAGCCAGTTCATCATCATGTACAGCCTGGATGGCAAGAAGTGGCA   - 4150
GACCTACAGGGGCAACAGCACTGGCACCCTGATGGTGTTCTTTGGCAATG   - 4200
TGGACAGCTCTGGCATCAAGCACAACATCTTCAACCCCCCCATCATTGCC   - 4250
AGATACATCAGGCTGCACCCCACCCACTACAGCATCAGGAGCACCCTGAG   - 4300
GATGGAGCTGATGGGCTGTGACCTGAACAGCTGCAGCATGCCCCTGGGCA   - 4350
TGGAGAGCAAGGCCATCTCTGATGCCCAGATCACTGCCAGCAGCTACTTC   - 4400
ACCAACATGTTTGCCACCTGGAGCCCCAGCAAGGCCAGGCTGCATCTGCA   - 4450
GGGCAGGAGCAATGCCTGGAGGCCCCAGGTCAACAACCCCAAGGAGTGGC   - 4500
TGCAGGTGGACTTCCAGAAGACCATGAAGGTGACTGGGGTGACCACCCAG   - 4550
GGGGTGAAGAGCCTGCTGACCAGCATGTATGTGAAGGAGTTCCTGATCAG   - 4600
CAGCAGCCAGGATGGCCACCAGTGGACCCTGTTCTTCCAGAATGGCAAGG   - 4650

1         10        20        30        40        50
|         |         |         |         |         |
TGAAGGTGTTCCAGGGCAACCAGGACAGCTTCACCCCTGTGGTGAACAGC   - 4700
CTGGACCCCCCCCTGCTGACCAGATACCTGAGGATTCACCCCCAGAGCTG   - 4750
GGTGCACCAGATTGCCCTGAGGATGGAGGTGCTGGGCTGTGAGGCCCAGG   - 4800
ACCTGTACTGAGGATCCAATAAAATATCTTTATTTTCATTACATCTGTGT   - 4850
GTTGGTTTTTTGTGTGTTTTCCTGTAACGATCGGGCTCGAGCGC
```

In preferred embodiments, the constructs described herein comprise insulator (spacer) sequences as shown in FIGS. 1, 2, 4, 6, 7, 10, 19, 20, and 25. Exemplary insulator sequences include Ins1: 5' GGAACCATTGCCACCTTCA (SEQ ID NO:28); Ins2: 5' CTATCCATTGCACTATGCT (SEQ ID NO:29); Ins3: 5' TTTCCTGTAACGATCGGG (SEQ ID NO:30) and Ins4: 5' TTGAATTCATAACTATCCCAA (SEQ ID NO:38).

As will be apparent, any transgene can be used in the constructs described herein. Furthermore, the individual components (promoter, enhancer, insulator, transgene, etc.) of the constructs described herein may be mixed and matched in any combination.

The constructs described herein may be contained within any viral or non-viral vector. The constructs may be maintained episomally or may be integrated into the genome of the cell (e.g., via nuclease-mediated targeted integration).

Non-viral vectors include DNA or RNA plasmids, DNA MCs, naked nucleic acid, and nucleic acid complexed with a delivery vehicle such as a liposome, nanoparticle or poloxamer. Viral vectors that may be used to carry the expression cassettes described herein include, but are not limited to, retroviral, lentivirus, adenoviral, adeno-associated viral vectors, vaccinia and herpes simplex virus vectors.

Integration in the host genome is possible with the retrovirus, lentivirus, and adeno-associated virus gene transfer methods, and as described herein may be facilitated by nuclease-mediated integration.

In certain preferred embodiments, the constructs are included in an adeno-associated virus ("AAV") vector or vector system that may be maintained episomally or integrated into the genome of a liver cell (e.g., via nuclease-mediated targeted integration). Construction of recombinant AAV vectors is in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

Thus, in certain embodiments, the expression construct is carried on an AAV construct and further comprises 5' and 3' ITRs flanking the expression constructs elements (e.g., enhancer, promoter, optional intron, transgene, etc.) as described herein. Optionally, spacer molecules are also included between one or more of the components of the expression construct, for example, between the 5' ITR and the enhancer and/or between the polyadenylation signal and the 3' ITR. The spacers may function as homology arms to facilitate recombination into a safe-harbor locus (e.g. albumin). In certain embodiments, the construct is a construct as shown in any of FIG. 1, 2, 4, 6, 7, 10, 18, 19, 20 or 25.

In certain embodiments, the AAV vectors as described herein can be derived from any AAV. In certain embodiments, the AAV vector is derived from the defective and nonpathogenic parvovirus adeno-associated type 2 virus. All such vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV2, AAV3, AAV4, AAV5, AAV6, AAV7, AAV8, AAV9 and AAVrh.10 and any novel AAV serotype can also be used in accordance with the present invention. In some embodiments, chimeric AAV is used where the viral origins of the LTR sequences of the viral nucleic acid are heterologous to the viral origin of the capsid sequences. Non-limiting examples include chimeric virus with LTRs derived from AAV2 and capsids derived from AAV5, AAV6, AAV8 or AAV9 (i.e. AAV2/5, AAV2/6, AAV2/8 and AAV2/9, respectively).

Retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

The constructs described herein may also be incorporated into an adenoviral vector system. Adenoviral based vectors are capable of very high transduction efficiency in many cell types and do not require cell division. With such vectors, high titer and high levels of expression have been obtained. This vector can be produced in large quantities in a relatively simple system.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Replication-deficient recombinant adenoviral vectors (Ad) can also be used with the polynucleotides described herein. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include HEK293 and Sf9 cells, which can be used to package AAV and adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. In some embodiments, AAV is produced using a baculovirus expression system.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

The polynucleotides described herein may include one or more non-natural bases and/or backbones. In particular, an expression cassette as described herein may include methylated cytosines to achieve a state of transcriptional quiescence in a region of interest.

Furthermore, the expression constructs as described herein may also include additional transcriptional or translational regulatory or other sequences, for example, Kozak sequences, additional promoters, enhancers, insulators, internal ribosome entry sites, sequences encoding 2A peptides, furin cleavage sites and/or polyadenylation signals. Further, the control elements of the genes of interest can be operably linked to reporter genes to create chimeric genes (e.g., reporter expression cassettes).

Transgenes

The constructs described herein can be used for hepatic delivery of any transgene. Exemplary transgenes (also referred to as genes of interest and/or exogenous sequences) include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the transgene comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

In certain embodiments, the transgene(s) encodes functional versions of proteins lacking of deficient in any genetic disease, including but not limited to, lysosomal storage disorders (e.g., Gaucher's, Fabry's, Hunter's, Hurler's, Neimann-Pick's, etc.), metabolic disorders, and/or blood disorders such as hemophilias and hemoglobinopathies, etc. See, e.g., U.S. Publication No. 20140017212 and 20140093913; U.S. Pat. Nos. 9,255,250 and 9,175,280.

For example, the transgene may comprise a sequence encoding a polypeptide that is lacking or non-functional in the subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasiaossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesisimperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240), acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Non-limiting examples of proteins (including functional fragments thereof such as truncated versions) that may be expressed as described herein include fibrinogen, prothrombin, tissue factor, Factor V, Factor VII, Factor VIII, Factor IX, Factor X, Factor XI, Factor XII (Hageman factor), Factor XIII (fibrin-stabilizing factor), von Willebrand factor, prekallikrein, high molecular weight kininogen (Fitzgerald factor), fibronectin, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, plasminogen activator inhibitor-2, glucocerebrosidase (GBA), α-galactosidase A (GLA), iduronate sulfatase (IDS), iduronidase (IDUA), acid sphingomyelinase (SMPD1), MMAA, MMAB, MMACHC, MMADHC (C2orf25), MTRR, LMBRD1, MTR, propionyl-CoA carboxylase (PCC) (PCCA and/or PCCB subunits), a glucose-6-phosphate transporter (G6PT) protein or glucose-6-phosphatase (G6Pase), an LDL receptor (LDLR), ApoB, LDLRAP-1, a PCSK9, a mitochondrial protein such as NAGS (N-acetylglutamate synthetase), CPS1 (carbamoyl phosphate synthetase I), and OTC (ornithine transcarbamylase), ASS (argininosuccinic acid synthetase), ASL (argininosuccinase acid lyase) and/or ARG1 (arginase), and/or a solute carrier family 25 (SLC25A13, an aspartate/glutamate carrier) protein, a UGT1A1 or UDP glucuronsyltransferase polypeptide A1, a fumarylacetoacetate hydrolyase (FAH), an alanine-glyoxylate aminotransferase (AGXT) protein, a glyoxylate reductase/hydroxypyruvate reductase (GRHPR) protein, a transthyretin gene (TTR) protein, an ATP7B protein, a phenylalanine hydroxylase (PAH) protein, a lipoprotein lyase (LPL) protein, an engineered nuclease, an engineered transcription factor and/or a therapeutic single chain antibody.

In certain embodiments, the transgene can comprise a marker gene (described above), allowing selection of cells that have undergone targeted integration, and a linked sequence encoding an additional functionality. Non-limiting examples of marker genes include GFP, drug selection marker(s) and the like.

The constructs described herein may also be used for delivery of non-coding transgenes. Sequences encoding antisense RNAs, RNAi, shRNAs and micro RNAs (miRNAs) may also be used for targeted insertions.

In certain embodiments, the transgene includes sequences (e.g., coding sequences, also referred to as transgenes) greater than 1 kb in length, for example between 2 and 200 kb, between 2 and 10 kb (or any value therebetween). The transgene may also include one or more nuclease target sites.

When integrated (e.g., via nuclease-mediate integration), the transgene may be inserted into an endogenous gene such that all, some or none of the endogenous gene is expressed.

Nucleases

As noted above, the expression cassettes may be maintained episomally or may be integrated into the genome of the cell. Integration may be random. Preferably, integration of the transgene construct(s) is targeted following cleavage of the target gene by one or more nucleases (e.g., zinc finger nucleases ("ZFNs"), TALENs, TtAgo, CRISPR/Cas nuclease systems, and homing endonucleases) and the construct integrated by either homology directed repair (HDR) or by end capture during non-homologous end joining (NHEJ) driven processes. See, e.g., U.S. Pat. Nos. 9,255,250; 9,200,266; 9,045,763; 9,005,973; 9,150,847; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983; 20130196373 and 20150056705, the disclosures of which are incorporated by reference in their entireties for all purposes.

Any nuclease can be used for targeted integration of the transgene expression construct.

In certain embodiments, the nuclease comprises a zinc finger nuclease (ZFN), which comprises a zinc finger DNA-binding domain and a cleavage (nuclease) domain. See, e.g., U.S. Pat. Nos. 9,255,250; 9,200,266; 9,045,763; 9,005,973; 9,150,847; 8,956,828; 8,945,868; 8,703,489; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861.

In other embodiments, the nuclease comprises a TALEN, which comprises a TAL-effector DNA binding domain and a cleavage (nuclease) domain. See, e.g., U.S. Pat. No. 8,586,526 and U.S. Publication No. 20130196373.

In still further embodiments, the nuclease comprises a CRISPR/Cas nuclease system, which includes a single guide RNA for recognition of the target site and one or more cleavage domains. See, e.g., U.S. Patent Publication No. 20150056705. In some embodiments, the CRISPR-Cpf1 system is used (see Fagerlund et al, (2015) *Genom Bio* 16:251). It is understood that the term "CRISPR/Cas" system refers to both CRISPR/Cas and CRISPR/Cfp1 systems.

The cleavage domains of the nucleases may be wild-type or mutated, including non-naturally occurring (engineered) cleavage domains that form obligate heterodimers. See, e.g., U.S. Pat. Nos. 8,623,618; 7,888,121; 7,914,796; and 8,034,598 and U.S. Publication No. 20110201055.

The nuclease(s) may make one or more double-stranded and/or single-stranded cuts in the target site. In certain embodiments, the nuclease comprises a catalytically inactive cleavage domain (e.g., FokI and/or Cas protein). See, e.g., U.S. Pat. Nos. 9,200,266; 8,703,489 and Guillinger et al. (2014) *Nature Biotech.* 32(6):577-582. The catalytically inactive cleavage domain may, in combination with a catalytically active domain act as a nickase to make a single-stranded cut. Therefore, two nickases can be used in combination to make a double-stranded cut in a specific region. Additional nickases are also known in the art, for example, McCaffery et al. (2016) *Nucleic Acids Res.* 44(2):ell. doi: 10.1093/nar/gkv878. Epub 2015 Oct. 19.

In certain embodiments, the nuclease cleaves a safe harbor gene (e.g., CCR5, Rosa, albumin, AAVS1, etc. See, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960. In preferred embodiments, the nuclease cleaves an endogenous albumin gene such that the expression cassette is integrated into the endogenous albumin locus of a liver cell. Albumin-specific nucleases are described, for example, in U.S. Pat. No. 9,150,847; and U.S. Publication Nos. 20130177983 and 20150056705.

Delivery

The constructs described herein (and/or nucleases) may be delivered in vivo or ex vivo by any suitable means into any cell type, preferably to the liver (hepatic delivery). Similarly, when used in combination with nucleases for targeted integration, the nucleases may be delivered in polynucleotide and/or protein form, for example using non-viral vector(s), viral vectors(s) and/or in RNA form, e.g., as mRNA.

Methods of non-viral delivery of nucleic acids include electroporation, lipofection, microinjection, biolistics, virosomes, liposomes, immunoliposomes, other nanoparticle, polycation or lipid:nucleic acid conjugates, naked DNA, artificial virions, and agent-enhanced uptake of DNA. Sonoporation using, e.g., the Sonitron 2000 system (RichMar) can also be used for delivery of nucleic acids. Additional exemplary nucleic acid delivery systems include those provided by AmaxaBiosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336).

In preferred embodiments, the expression constructs are AAV vectors. The optional nucleases may be administered in mRNA form or using one or more viral vectors (AAV, Ad, etc.). Administration can be by any means in which the polynucleotides are delivered to the desired target cells. Both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics,* 6:335-341.

In systems involving delivery of more than one polynucleotides (e.g., construct as described herein and nuclease in polynucleotide form), the two or more polynucleotide(s) are delivered using one or more of the same and/or different vectors. For example, the nuclease in polynucleotide form may be delivered in mRNA form and the liver-specific constructs as described herein may be delivered via other modalities such as viral vectors (e.g., AAV), minicircle DNA, plasmid DNA, linear DNA, liposomes, nanoparticles and the like.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

The effective amount of expression cassette (and optional nuclease(s), and/or modified cells) to be administered will vary from patient to patient. Accordingly, effective amounts are best determined by the physician administering the compositions (e.g., cells) and appropriate dosages can be determined readily by one of ordinary skill in the art. Analysis of the serum, plasma or other tissue levels of the therapeutic polypeptide and comparison to the initial level prior to administration can determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.,* 6:1391-1401.

Formulations for both ex vivo and in vivo administrations include suspensions (e.g., of genetically modified cells, liposomes or nanoparticles) in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods and compositions disclosed herein are for providing therapies for any disease by provision of a transgene that expresses a product that is lacking or deficient in the disease or otherwise treats or prevents the disease. The cell may be modified in vivo or may be modified ex vivo and subsequently administered to a subject. Thus, the methods and compositions provide for the treatment and/or prevention of such genetic diseases.

The following Examples include exemplary embodiments of the present disclosure in which the optionally used nuclease comprises a zinc finger nuclease (ZFN). It will be appreciated that this is for purposes of exemplification only and that other nucleases can be used, for example TALENs, CRISPR/Cas systems, homing endonucleases (meganucleases) with engineered DNA-binding domains and/or fusions of naturally occurring of engineered homing endonucleases (meganucleases) DNA-binding domains and heterologous cleavage domains and/or fusions of meganucleases and TALE proteins. In addition, it will be appreciated that expression constructs as described herein can be carried on other vectors (other than AAV) to produce the same results in the treatment and/or prevention of disorders caused by deficient protein production.

Examples

Example 1: Methods

DNA Constructs

The overall structure and approach followed for the development of exemplary constructs carrying the human Factor VIII cDNA is depicted in FIG. 1. The constructs include a liver-specific enhancer, liver-specific promoter, an optional intron, insulator sequences and a transgene (e.g., codon-optimized human Factor VIII B-domain deleted transgene), synthetic poly adenylation sequence, spacers and 5'/3' inverted terminal repeats. All constructs were assembled using routine molecular biology cloning methods.

As shown in FIG. 1, several steps were followed during the vector development. We initially examined the effect of the construct components on the viral yield obtained during manufacturing. The influence of the sequence of the insulator regions in the constructs was explored by using three difference potential insulator sequences, as shown: Ins 1: 5' GGAACCATTGCCACCTTCA (SEQ ID NO:28), Ins2: 5' CTATCCATTGCACTATGCT (SEQ ID NO:29), and Ins3: 5' TTTCCTGTAACGATCGGG (SEQ ID NO:30). The insulator regions were then inserted into the transgene expression cassette where the insulator used between the 5' ITR sequence and the beginning of the enhancer/promoter sequence was always Ins1. However, the at the 3' end of the construct, either Ins2 or Ins3 sequences were linked to the SPA51 synthetic poly A sequence (5' AATAAAATATCTT-TATTTTCATTA-CATCTGTGTGTTGGTTTTTTGTGTGTT, SEQ ID NO:31) as follows: Ins2-SPA51: 5' ATAAAATATCTTTAT-TTTCATTACATCTGTGTGTTGGTTTTTTGTGTGTTC-TAT CCATTGCACTATGCT, SEQ ID NO:32, and Ins3-SPA51: 5' AATAAAATATCTTTATTTTCATTA-CATCTGTGTGTTGGTTTTTTGTGTGTTTC CTGTAACGATCGGG, SEQ ID NO:33. In some embodiments, Ins4 is linked to the SPA51.

Figure 2:
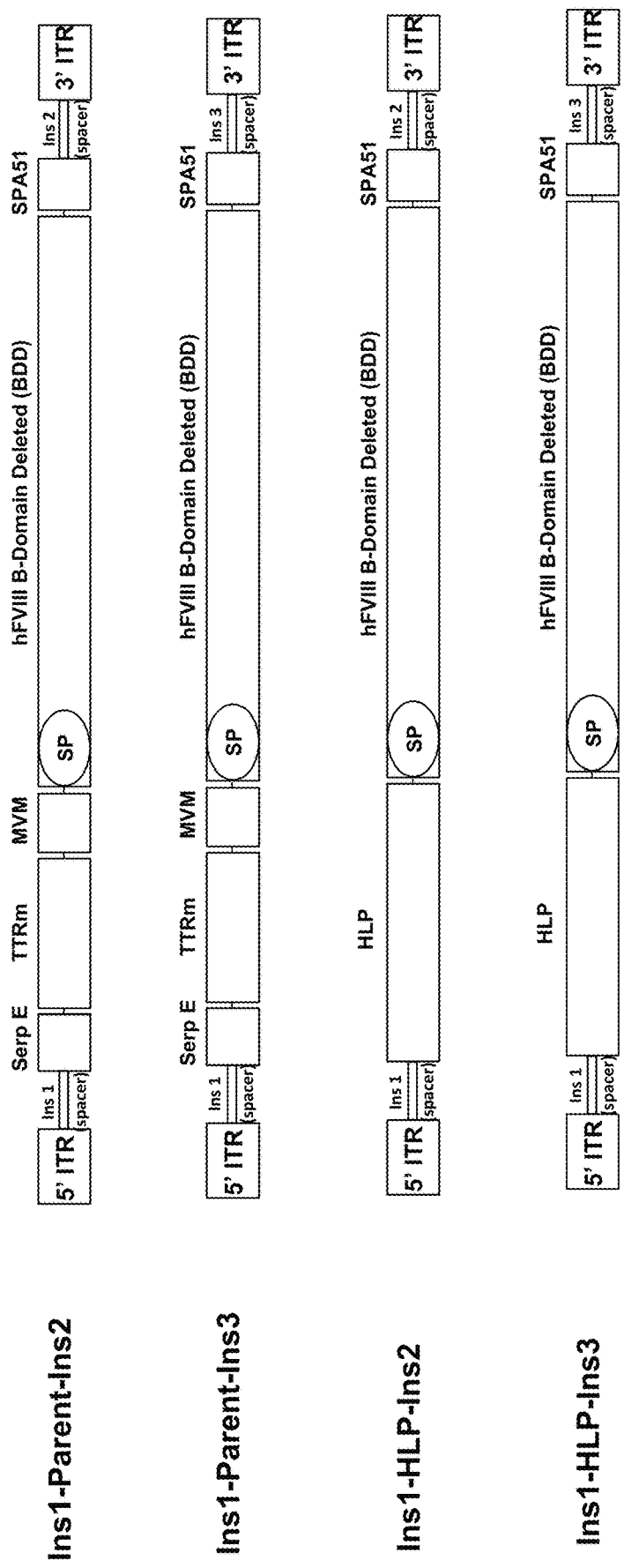
FIG. 2 is a schematic depicting parent TTRm promoter and HLP constructs with Insulators 1-3 ("Ins1-3"). SerpE refers to the Serpin enhancer from the SERPINA1 gene which is a liver-specific Serpin regulatory element. TTRm refers to transthyretin minimal promoter. HLP refers to hybrid liver specific promoter (McIntosh et al., ibid). hFVIII refers to human factor VIII B-domain deleted transgene. SP refers to signal peptide. ITR refers to inverted terminal repeat. SPA refers to synthetic poly adenylation sequence.
Figure 3:
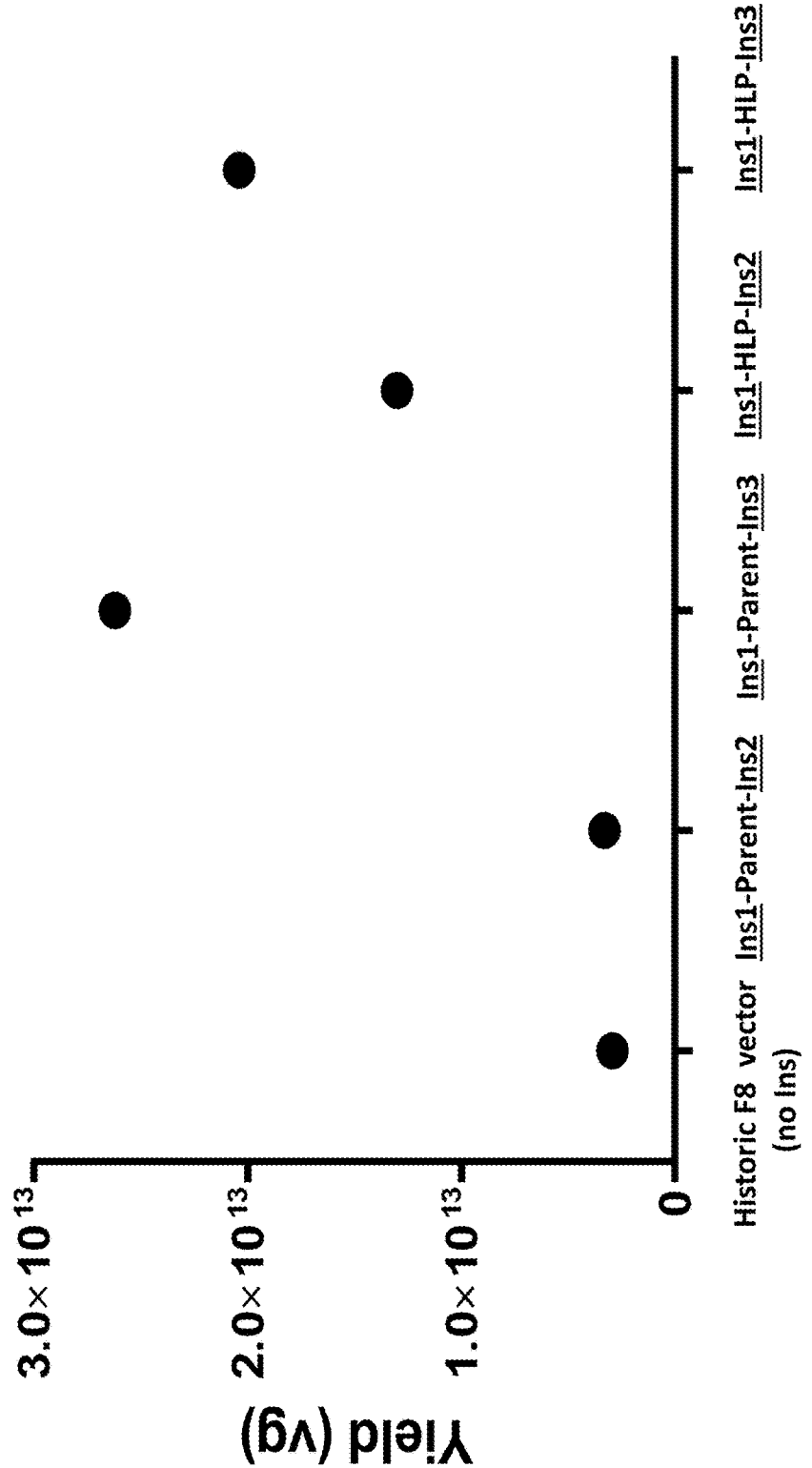
FIG. 3 is a graph depicting the yield of different AAV constructs comprising different insulator sequences or promoter regions. Improved yields from Ins1-Ins3 compared to Ins1-Ins2 in the context of the parent TTRm promoter or HLP constructs are seen in the figure. Virus was produced in HEK293 cells, yields are from two cell factories (2 CF). SerpE refers to the Serpin enhancer from the SERPINA1 gene which is a liver-specific Serpin regulatory element. TTRm refers to transthyretin minimal promoter. HLP refers to hybrid liver specific promoter (McIntosh et al., ibid). hFVIII refers to human factor VIII B-domain deleted transgene. SP refers to signal peptide. ITR refers to inverted terminal repeat. SPA refers to synthetic poly adenylation sequence.
Figure 22:
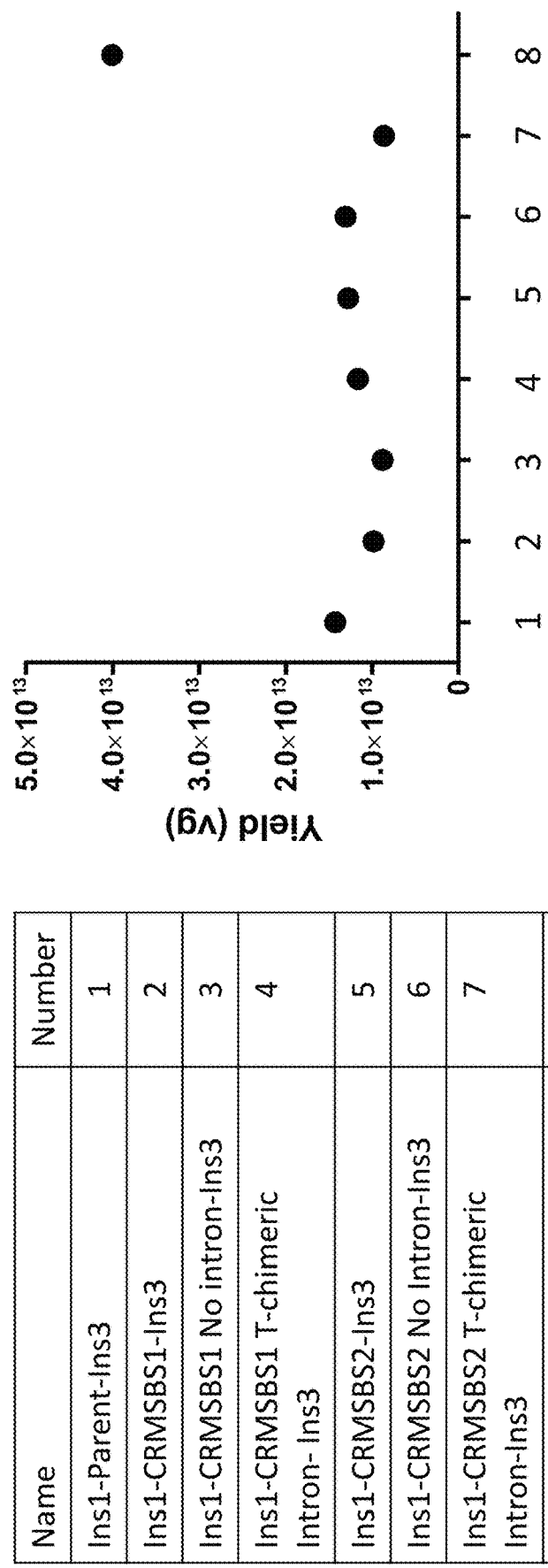
FIG. 22 is a graph showing improved production yields in the context of CRMSBS1 or CRMSBS2 intron series. Virus was produced in HEK293 cells, yields are from two cell factories (2 CF). CRM refers to cis-regulatory element. SBS refers to Sangamo Biosciences. hFVIII refers to human factor VIII. SP refers to signal peptide. ITR refers to inverted terminal repeat. SPA refers to synthetic poly adenylation sequence. Ins1 and Ins3 refers to Insulator 1, and Insulator 3, respectively.

The Ins sequence variants were also used in expression constructs where the SerpE-TTRm-MVM promoter region was replaced with a hybrid liver promoter (HLP, McIntosh et al, ibid). These constructs are illustrated in FIG. 2. These constructs were then packaged into AAV2/6 particles using HEK293 cells where the yields are from 2 cell factories (Yuan et al., (2011) *Hum Gene Ther.,* 22, 613-624, 2011) .The yield (vector genomes) for the constructs containing the modified insulator sequences were found nearly three logs higher for the construct comprising the parent promoter region where the expression cassette was flanked by the Ins1 and Ins3 insulator regions at the 5' and 3' ends, respectively (FIG. 3). In addition, these insulator sequences were also inserted into the modified CRMSBS1 and CRMSBS2 constructs described below in step 2 (FIGS. 19 and 20), and tested for viral yield (FIG. 22). The data showed a 8-10 fold improvement in viral yield for the new construct as compared to the parent construct.

Figure 4:
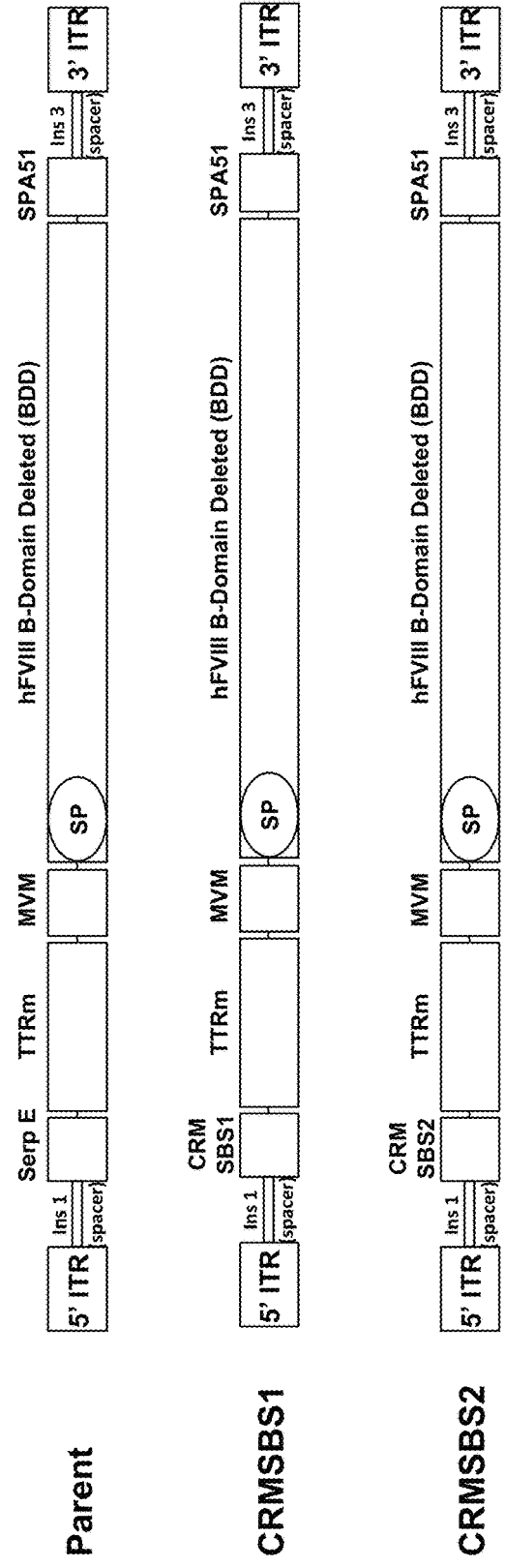
FIG. 4 is a schematic depicting parent, and constructs with new enhancers designated CRMSBS1 and CRMSBS2, each carrying a human Factor VIII B-domain deleted (Factor VIII-BDD) transgene. "SerpE" refers to the Serpin enhancer from the SERPINA1 gene which is a liver-specific Serpin regulatory element. "TTRm" refers to transthyretin minimal promoter. "SBS" refers to an internal Sangamo Biosciences numeric reference. "hFVIII" refers to human factor VIII BDD transgene. "SP" refers to signal peptide. "ITR" refers to inverted terminal repeat. "SPA" refers to synthetic poly adenylation sequence. "Ins1" and "Ins3" are as described above in FIG. 2.

In step 2, point mutations were introduced in the Serpin 1 enhancer to create the first two derivative vectors CRMSBS1 and CRMSBS2 (FIG. 4). These vectors differ in their enhancer sequences where point mutations were introduced as shown in FIG. 5. The specific changes made are the following: for CRMSBS1, denoted as 1, 2, 3, and 4 as depicted in FIG. 5 the following substitutions were made, respectively: 1=G to A, 2=C to G, 3=T to C and 4=G to A. Similarly, for CRMSBS2, positions 1, 3, 4 and 5 were modified as follows: 1=G to A, 3=T to C, 4=G to A and 5=C to T.

Figure 6:
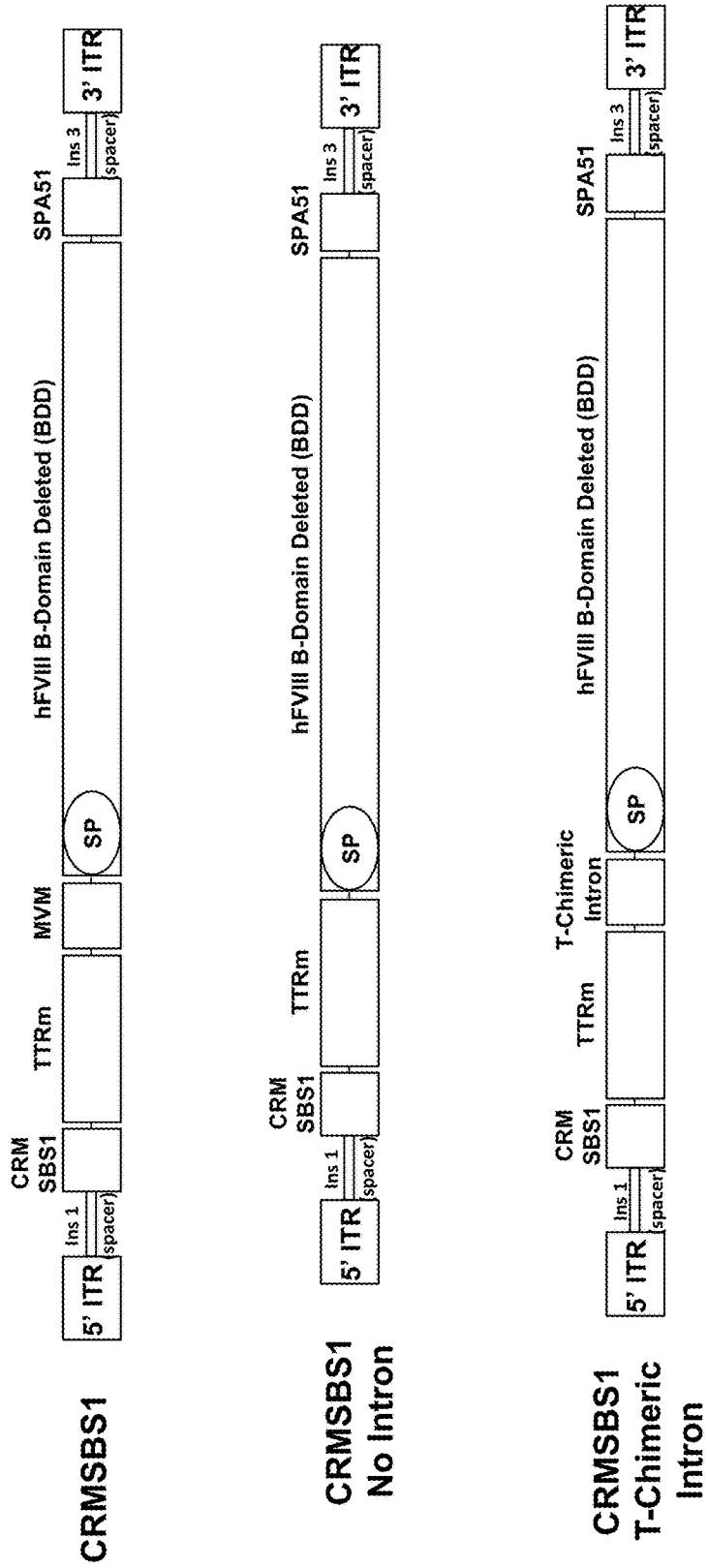
FIG. 6 is a schematic depicting CRMSBS1, and 2 constructs derived from CRMSBS1 with no MVM intron (CRMSBS1 No Intron), or a truncated chimeric intron (CRMSBS1 T-Chimeric Intron), each construct including a Factor VIII BDD transgene. "CRM" refers to cis-regulatory element. "SBS" refers to Sangamo Biosciences internal numeric reference. "hFVIII" refers to human factor VIII-BDD. "SP" refers to signal peptide. "ITR" refers to inverted terminal repeat. "SPA" refers to synthetic poly adenylation sequence. "Ins1" and "Ins3" are as described above in FIG. 2.
Figure 7:
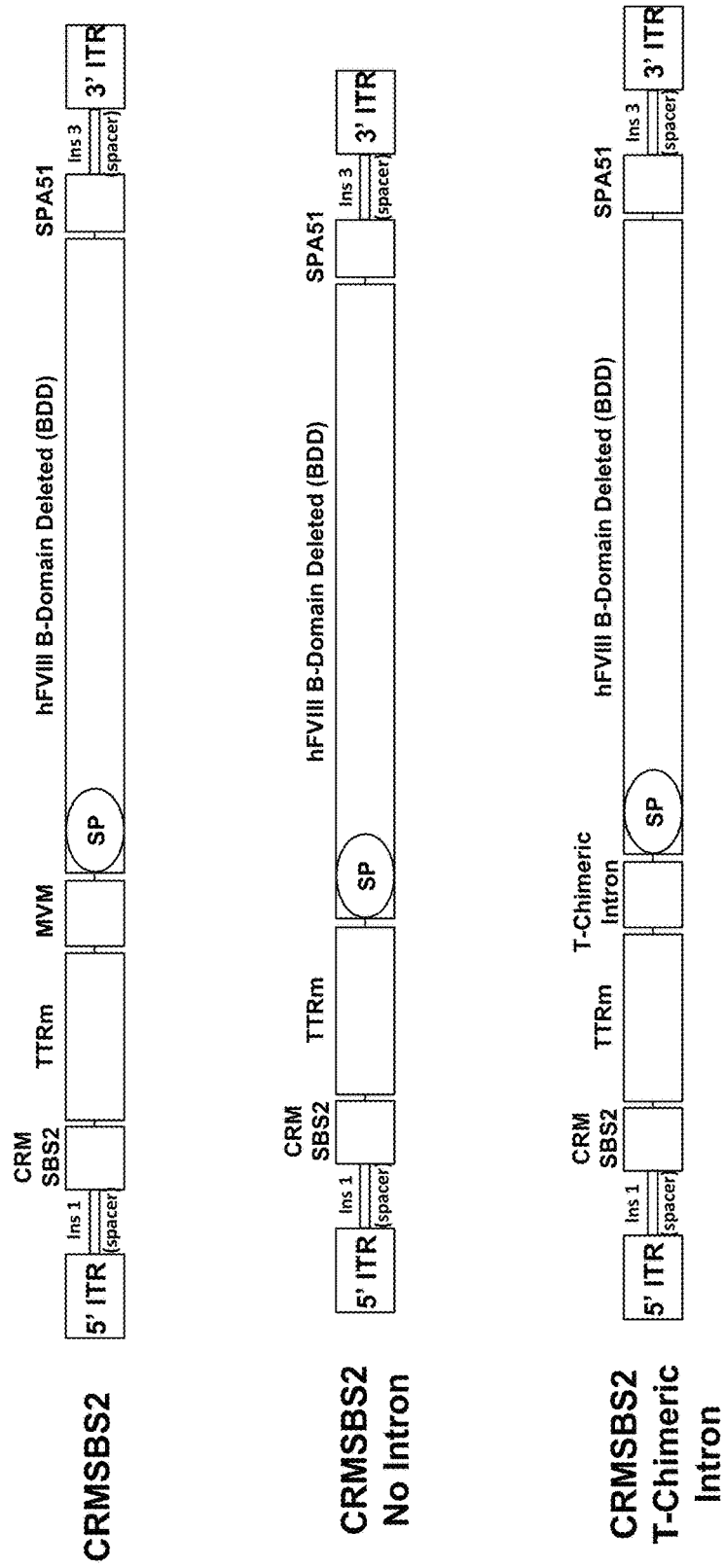
FIG. 7 is a schematic depicting CRMSBS2, and 2 constructs derived from CRMSBS2 with no MVM intron (CRMSBS2 No Intron), or a truncated chimeric intron (CRMSBS2 T-Chimeric Intron), each construct including a Factor VIII BDD transgene. "CRM" refers to cis-regulatory element. "SBS" refers to Sangamo Biosciences internal numeric reference. "hFVIII" refers to human factor VIII BDD. "SP" refers to signal peptide. "ITR" refers to inverted terminal repeat. "SPA" refers to synthetic poly adenylation sequence. "Ins1" and "Ins3" are as described above in FIG. 2.

In step 3, constructs were made to investigate the intron sequence in the vector. As shown in FIGS. 6 and 7, the intron sequences in the CRMSBS2 and CRMSBS2 vectors were modified by removing the MVM intron ("CRMSBS1 No intron", FIG. 6, and "CRMSBS2 No intron", FIG. 7). In another variant, a T-chimeric intron sequence was tested ("CRMSBS1 T-chimeric intron", FIG. 6, and "CRMSBS2 T-chimeric intron", FIG. 7).

Figure 10:
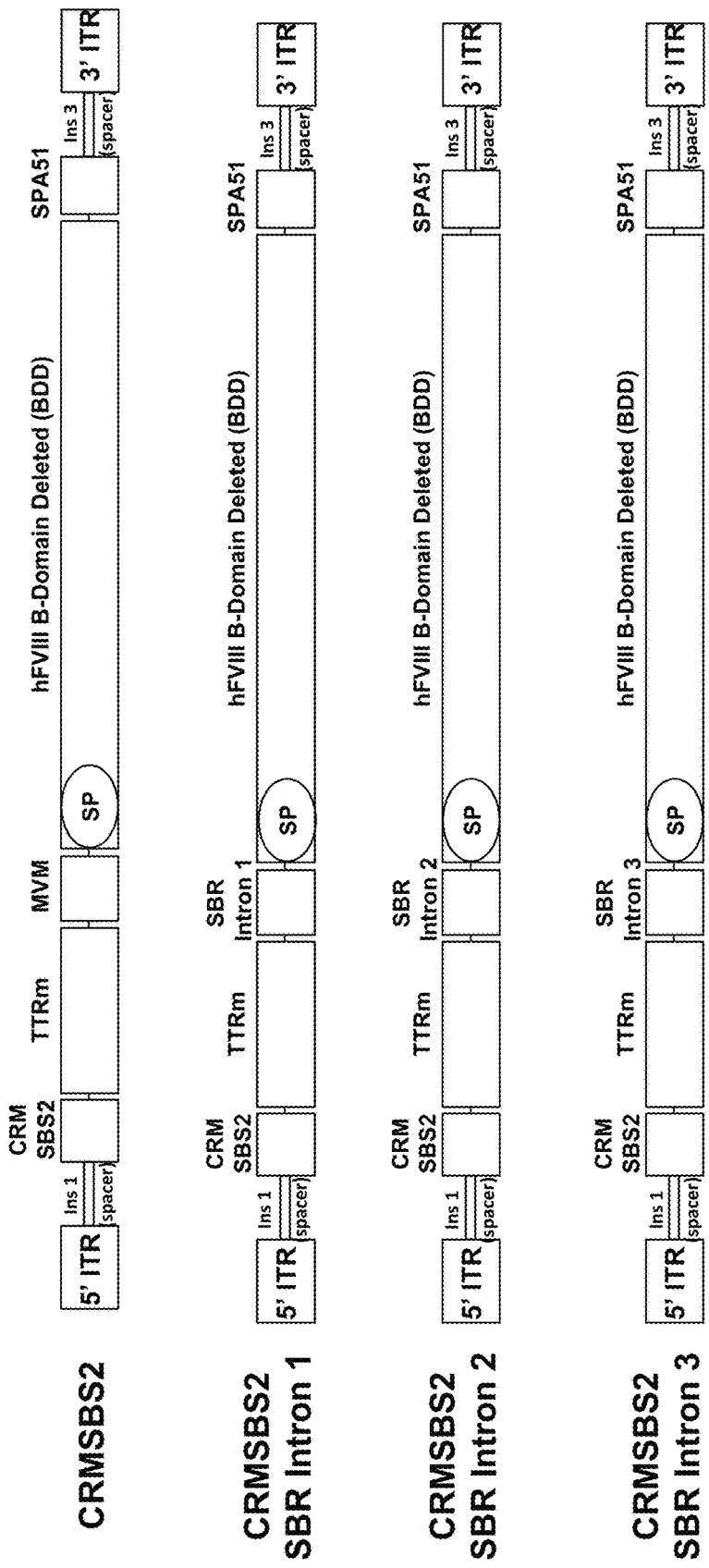
FIG. 10 are schematics depicting construct CRMSBS2, and additional constructs (designated CRMSBS2 SBR Introns 1, 2 or 3). All constructs include a human Factor VIII BDD transgene. "CRM" refers to cis-regulatory element. "SBS" refers to an internal Sangamo Biosciences internal numeric reference. "hFVIII" refers to human factor VIII-BDD transgene. "SP" refers to signal peptide. "ITR" refers to inverted terminal repeat. "SPA" refers to synthetic poly adenylation sequence. "MVM" refers to a MVM intron sequence.
Figure 11:
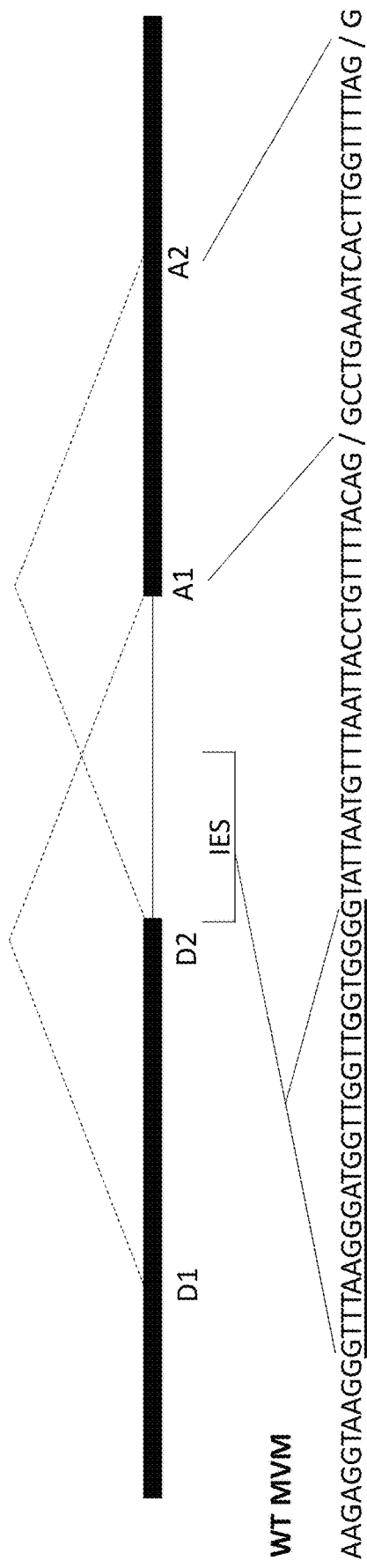
FIG. 11 is a schematic depicting the wild-type minute virus of mouse intron ("WT MVM"), including partial sequence (SEQ ID NO:14) and location of donors and acceptors. "D1" and "D2" refer to donors 1 and 2, respectively. "A1" and "A2" refers to acceptors 1 and 2, respectively. "IES" refers to intronic enhancer sequence. See, also, Haut and Pintel (1998) *J. Virology* 72:1834-1843 and Haut and Pintel (1998) *Virology J.*, 258:84-94.
Figure 21:
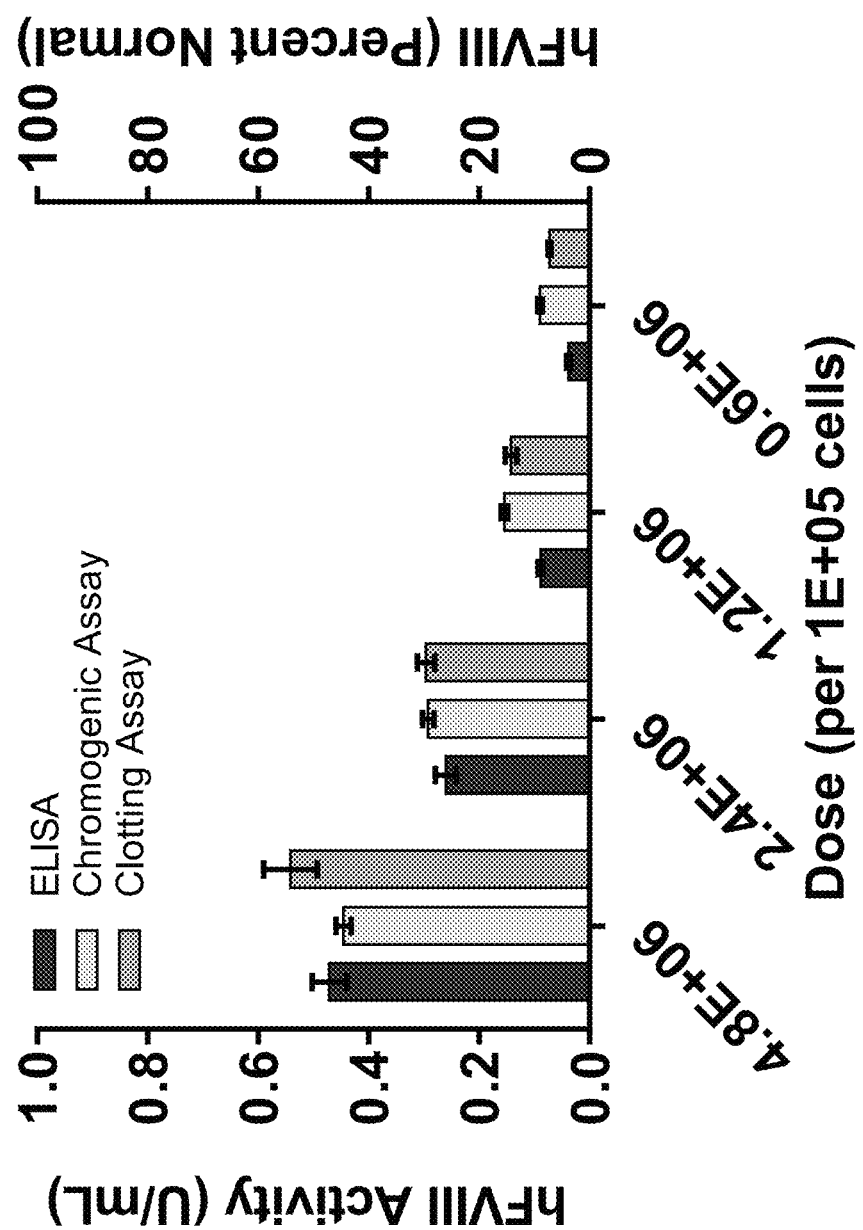
FIG. 21 is a graph depicting the evaluation of hFVIII levels and activity by AAV F8 cDNA expression in vitro in HepG2 cells. AAV2/6 F8 cDNA (CRMSBS2 SBR Intron 3) was added to HepG2 cells at doses of 4.8E+06, 2.4E+06, 1.2E+–6 and 0.6E+06 viral genomes per 1E+05 cells in a 24-well dish (denoted as time t0 days). Supernatants were analyzed for secreted hFVIII levels by ELISA, (left-most bars) and activity by the APTT clotting assay (right-most bars) and the chromogenic activity assay (middle bars) at seven days (t7) post-AAV2/6 virus addition. Results demonstrated good correlation between secreted hFVIII levels and activity (reported as U/mL on the left hand axis, and Percent Normal on the right hand y axis, 1U/mL=100 Percent Normal). Data shown are of n=6 biological replicates. Error bars represent the standard error of the mean.

For step 4, changes were made to the MVM intron through the introduction of mutations aimed at the splice donor and acceptor sites. The maps of these vectors are shown in FIG. 10, where the altered introns are referred to as SBR Intron 1-3. The MVM intron has two potential donor sites and two potential acceptor sites of those donors (see FIG. 11 for an illustration). In FIG. 11, the two donor sites are denoted with D1 and D2, and their corresponding acceptor sites are shown as A1 and A2. The splice junctions made by the splice of D1-A1 and D2-A2 are shown above the gene as dotted lines. A partial sequence of the MVM intron is shown below the gene in FIG. 11 (SEQ ID NO:14) and the location (underlined) of the intronic enhancer sequence (IES) is indicated as well as the sites of the A1 and A2 acceptors (Haut and Pintel, (1998) J Virol, 72:1834-1843; Haut and Pintel, (1998) Virol J, 258:84-94). Three introns were constructed for testing, and these are illustrated in FIG. 10, and are denoted SBR Intron 1-3 (intron sequences shown in SEQ ID NOs:15-17). Activity of the expressed hFVIII delivered by AAV F8 cDNA was also evaluated in vitro. AAV2/6 F8 cDNA (CRMSBS2 SBR Intron 3) was added to HepG2 cells at doses of 4.8E+06, 2.4E+06, 1.2E+06 and 0.6E+06 vector genomes/mL per 1E+05 cells in a 24-well dish (denoted as time, t0 days). Supernatants were analyzed for secreted hFVIII levels by ELISA, and activity by the APTT clotting assay and the Chromogenic activity assay at seven days (t7) post-AAV2/6 virus addition (for methods, see below). Results (FIG. 21) demonstrated good correlation between secreted hFVIII levels and activity. Data shown are of n=6 biological replicates. Error bars represent the standard error of the mean of replicates.

These constructs were then tested in vivo as described below.

Quantitative PCR qRT-PCR (for Human Factor VIII mRNA Levels):

Mouse tissue was lysed using FastPrep and Lysing Matrix D (MP Biomedicals, Santa Ana Calif.) per the manufacturer's instructions. RNA/DNA was isolated from mouse tissue using AllPrep DNA/RNA kit per the manufacturer's instructions (Qiagen, Carlsbad Calif.). Extracted RNA was then used to make cDNA using Quantitect cDNA synthesis kit (Qiagen, Carlsbad Calif.). Quantitative PCR was then carried out using SsoAdvanced Universal Probes Supermix (Biorad, Hercules Calif.) on the Biorad CFX 96 using labelled primer/probe assays from IDT (Coralville Iowa). The mouse GAPDH assay was Mm.PT.39a.1. For the specific detection of human Factor VIII mRNA the primer/probe assay was custom; Forward primer (GGAGAT-GAAGAAGGAGGACTTTG) (SEQ ID NO:18), probe (ACATCTACGACGAGGACGAGAACCA) (SEQ ID NO:19) and Reverse primer (TCCACAGCAGCAAT-GAAGTAG) (SEQ ID NO:20). Quantitative qRT-PCR (not absolute) was used with normalization to GAPDH for each sample, and final data analyses was reported as relative to one mouse sample which was set to 1.0. No template control and no reverse transcriptase controls were run with all samples and produced no detectable signal.

qPCR (for Vector Genome, VG, Analyses):

Mouse tissue was lysed using FastPrep and Lysing Matrix D (MP Biomedicals, Santa Ana Calif.) per the manufacturer's instructions. RNA/DNA was isolated from mouse tissue using AllPrep DNA/RNA kit per the manufacturer's instructions (Qiagen, Carlsbad Calif.). Extracted DNA was used for quantitative PCR with TaqMan Fast Universal PCR Master Mix, No AmpErase UNG (Applied Biosystems, Foster City, Calif.) on the AB 7300 real-time PCR system (Applied Biosystems, Foster City, Calif.). For the specific detection of human Factor VIII the primer/probe assay was custom; forward primer (CCTGGGCCAGTTCCTGCT) (SEQ ID NO:21), probe (TTCTGCCACATCAGCAGCCACCA) (SEQ ID NO:22) and reverse primer (GGCCTCCATGC-CATCATG) (SEQ ID NO:23). No-template controls were run with all samples and produced no detectable signal. The qPCR DNA standard curve was generated from seven, serial 4-fold dilutions of a known amount of purified, linearized human Factor VIII plasmid.

qPCR (for Targeted Integration by NHEJ Using HepG2 Cells)—

DNA was isolated from human HepG2 cells using QIAamp DNA micro per the manufacturer's instructions (Qiagen, Carlsbad Calif.). Quantitative PCR was then carried out using SsoAdvanced Univesal Probes Supermix (Biorad, Hercules Calif.) on the Biorad CFX 96 using labelled primer/probe assays from IDT (Coralville Iowa). The human GAPDH assay was Hs.PT.39a.22214836. For the specific detection of targeted integration of human Factor VIII by NHEJ at the endogenous human albumin locus the primer/probe assay was custom; Forward primer (AGTGCAAAGTAACTTAGAGTGACT) (SEQ ID NO:24), probe (CCATCACTAGGGGTTCCTGCGGCCT) (SEQ ID NO:25) and Reverse primer (CCT-GAAGGTGGCAATGGT) (SEQ ID NO:26). For the purposes of this study we used quantitative qPCR (not absolute) with normalization to GAPDH for each sample, and final data analyses reported as relative to one sample which was set to 1.0. No template control, no transcriptase control and no ZFN controls were run and produced no detectable signal.

qPCR (for Targeted Integration by NHEJ and HDR from Mouse Tissues)—

Mouse tissue was lysed using FastPrep and Lysing Matrix D (MP Biomedicals, Santa Ana Calif.) per the manufacturer's instructions. RNA/DNA was isolated from mouse tissue using AllPrep DNA/RNA kit per the manufacturer's instructions (Qiagen, Carlsbad Calif.). Quantitative PCR was then carried out using SsoAdvanced Universal Probes Supermix (Biorad, Hercules Calif.) on the Biorad CFX 96 using labelled primer/probe assays from IDT (Coralville Iowa). The mouse GAPDH assay was Mm.PT.39a. 1. For the specific detection of targeted integration of human Factor 8 cDNA by NHEJ at the endogenous mouse albumin locus the primer/probe assay was custom; Forward primer (GTGTAGCAGAGAGGAACCATT, SEQ ID NO:39), probe (CCATCACTAGGGGTTCCTGCGGCCT, SEQ ID NO:40) and Reverse primer (GTTAATATT-CACCAGCAGCCT, SEQ ID NO:41). For the specific detection of targeted integration of ZFNs by NHEJ at the endogenous mouse albumin locus the primer/probe assay was custom; Forward primer (AGTGTAGCAGAGAG-GAACCA, SEQ ID NO:42), probe (CCAT-CACTAGGGGTTCCTGCGGCCT, SEQ ID NO:43) and Reverse primer (CAGGGTGAGCCCAGAAAC, SEQ ID NO:44). For the specific detection of targeted integration of human Factor 8 by HDR at the endogenous mouse albumin locus the primer/probe assay was custom; Forward primer (AACTTTGAGTGTAGCAGAGAGG, SEQ ID NO:45), probe (TACCGGAGGAGCAAACAGGGACTA, SEQ ID NO:46) and Reverse primer (CTCTACGAAATGTGCA-GACAGA, SEQ ID NO:47). For the purposes of this study we used quantitative qPCR (not absolute) with final data analyses reported as relative to one sample which was set to 1.0. No template control, no transcriptase control and no ZFN controls were run and produced no detectable signal.

Indel (Insertions and Deletions)—

Mouse tissue was lysed using FastPrep and Lysing Matrix D (MP Biomedicals, Santa Ana Calif.) per the manufacturer's instructions. RNA/DNA was isolated from mouse tissue using AllPrep DNA/RNA kit per the manufacturer's instructions (Qiagen, Carlsbad Calif.). Extracted DNA was used for PCR and deep sequencing to measure indels at the mouse albumin locus.

Plasma—

Blood was collected from all mice on Days 7, 14, 21 (non-terminal) and Day 28, or longer as noted (terminal) for the C57BL/6 studies. Blood was collected from all mice on Days 8, 14, 21, 28, 35 and 42 (non-terminal) for the Hemophilia A mouse studies. All blood was collected into tubes containing sodium citrate and processed to plasma. Non-terminal blood collections were collected via the submandibular vein or the retro-orbital sinus. Blood collections at the time of sacrifice were collected via cardiac puncture or vena cava. The plasma was separated and stored at −60 to −80° C. until use in the ELISA assay or Chromogenix Coamatic activity assay described below.

Liver—

For the C57BL/6 studies, mice were sacrificed at Day 28 and the liver, spleen, testes, brain, heart, lung and kidneys were collected and weighed. The left lateral lobe of the liver was separated and divided into 3 pieces and snap frozen in liquid nitrogen separately from the rest of the liver. The remaining liver lobes and other tissues (whole) were snap frozen in liquid nitrogen. Frozen specimens were stored at −60 to −80° C. until processing for RNA/DNA extraction.

In Vitro Studies, HepG2 AAV F8 cDNA/ZFNs.

Human HepG2 liver cells were maintained per manufacturer's guidelines (ATCC, Manassas Va.). On the day of the experiment, HepG2 cells were washed, trypsinized and counted. ZFNs used were to the human albumin intron 1 locus, left SBS47171 and right SBS47898. ZFNs, together with the hF8 cDNA (CRMSBS2 No Intron) were delivered as AAV2/6, denoted as time zero. AAV2/6 ZFNs were delivered at 3.0E+05, and AAV2/6 hFVIII cDNA CRMSBS2 No Intron at 3.0E+04, 6.0E+04 and 1.2E+05 for 1E+05 cells per well of a 24-well dish. The following day media was exchanged. Supernatants were analyzed for secreted hFVIII using the hFVIII ELISAs described below at time points t3, t5 and t7 days post-AAV2/6 virus addition.

In Vitro Studies, HepG2 AAV F8 cDNA.

Human HepG2 liver cells were maintained per manufacturer's guidelines (ATCC, Manassas Va.). On the day of the experiment, HepG2 cells were washed, trypsinized and counted. AAV2/6 hF8 cDNA (CRMSBS2 SBR Intron 3) was delivered at doses of 6.0E+06, 1.2E+06, 2.4E+06 and 4.8E+06 per 1E+05 cells in a well of a 24-well dish. Media was exchanged at time point t3 (t=day). Supernatants at time points t5 and t7 post-AAV 2/6 virus addition were analyzed for secreted hFVIII levels using the hFVIII ELISA from Affinity Biologics, and for hFVIII activity by the Chromogenic and Clotting Assays described below.

Human Factor VIII ELISA. Affinity Biologics hFVIII ELISA (Mouse and HepG2 Cells).

Secreted human Factor VIII levels were determined using Affinity Biologicals (Canada) ELISA kit (FVIII-AG) according to the manufacture's protocol with the exception of the human Factor VIII standard. The human Factor VIII standard used in the ELISA assay was a recombinant purified human Factor VIII (#F0016-06) from US Biologicals (Salem, Mass.). Briefly mouse plasma was added to the plate, incubated with rocking at room temperature for one and a half hours, followed by washing three times with wash buffer provided in the kit. Detecting antibody, provided with the kit, was added and incubated for forty five minutes at room temperature, followed by washing three times with wash buffer provided in the kit. TMB substrate provided with kit was added and allowed to develop for ten minutes. The reaction was stopped with stop solution and absorbance read at 450 nM using a plate reader.

In-House hFVIII ELISA (Cynomolgus Monkey).

Levels of hFVIII secreted into NHP plasma were determined using a custom ELISA. Polystyrene microplates (Corning, 96-well half-area high binding) were coated overnight at 4° C. with mouse monoclonal anti-hFVIII antibody (Green Mountain, Burlington, Vt.) in 0.2 M carbonate bicarbonate buffer pH 9.4 (Thermo Fisher Scientific, Waltham Mass.). The following day the plates were washed four times using 1×TBST (Thermo Fisher Scientific, Waltham Mass.). 96-well plates were then blocked two hours at room temperature using 3% BSA/TBS blocking buffer, followed by washing four times with 1×TBST. Plasma was added to the plate and incubated with rocking at room temperature for two hours, followed by washing four times with 1×TBST. Detection antibody, biotinylated monoclonal mouse anti-FVIII antibody (Green Mountain, Burlington, Vt.) was added and incubated for one hour at room temperature, followed by washing four times with 1×TBST. Streptavidin HRP (Jackson ImmunoResearch, West Grove Pa.) was added and incubated for one hour at room temperature followed by washing four times with 1×TBST. TMB Ultra (Thermo Fisher Scientific, Waltham Mass.) was added and allowed to develop for ten minutes, reaction was stopped with stop solution and absorbance read at 450 nM using a plate reader. Background absorbance readings were negligible (typically 0).

Chromogenic Human Factor VIII Activity Assay.

Activity of secreted human Factor VIII in plasma was determined using the Diapharma Chromogenic Coamatic Factor VIII assay (West Chester, Ohio) according to the manufacture's protocol with the exception of the human Factor VIII standard. The human Factor VIII standard used in the ELISA assay was a recombinant purified human Factor VIII (#F0016-06) from US Biologicals (Salem, Mass.).

Clotting Activity Assay

Activity of secreted human Factor VIII in HepG2 supernatant (or Cynomolgus monkey plasma) was determined using the activated partial thromboplastin time (aPTT) assay by Diagnostica Stago (Boston Mass.) according to the manufacture's protocol with the exception of the human Factor VIII standard and human Factor VIII-deficient plasma. The human Factor VIII standard was the same as used in the ELISA assay (recombinant purified human Factor VIII, #F0016-06 from US Biologicals, Salem, Mass.). The deficient FVIII reagent used in the clotting assay was FVIII-CD<1% FVIII Activity (frozen deficient FVIII) from Haematologic Technologies, Inc. (Essex Junction, Vt.). Briefly, standard or sample was added to cuvettes containing a steel ball. FVIII-CD<1% FVIII Activity and PTT Automate provided with the kit were added, incubated at 37° C. for one hundred eighty seconds. STA CaCl$_2$ provided with the kit was added to reaction while the steel ball went into motion within the cuvette. Clotting time was measured from the addition for STA CaCl$_2$ until the movement of the steel ball has stopped. Incubation and recording of time was done using the Stago Start Hemostasis Analyzer for this assay.

Example 2: In Vivo Studies

Figure 8B:
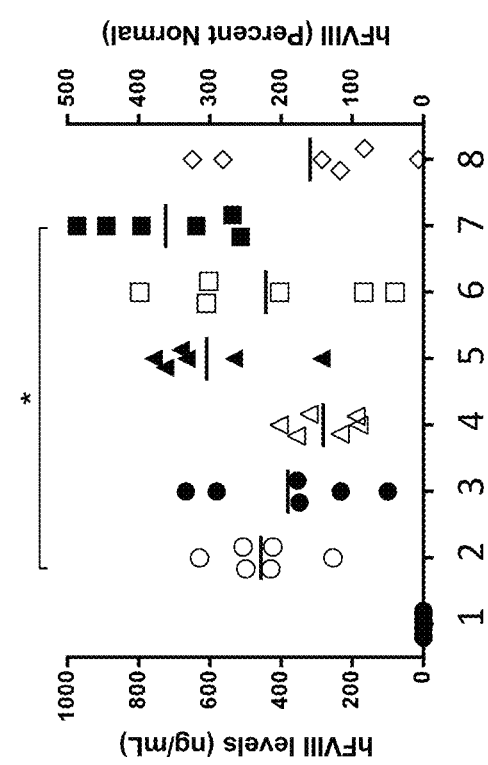
FIGS. 8A and 8B are graphs showing in vivo production of human secreted Factor VIII BDD following administration of the indicated constructs to mice. C57BL/6 mice were transduced with 6E+12 vg/kg of AAV2/6 hFVIII-BDD constructs.
Figure 15B:
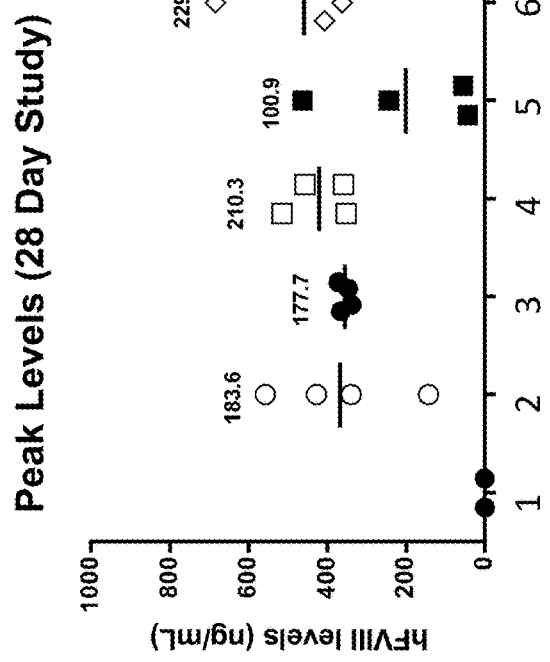
FIGS. 15A and 15B depict the in vivo production of human secreted Factor VIII B-domain deleted in mice with the novel intron sequences.

Wild Type Mice:

Eight to ten week old C57BL/6 mice were used for the in vivo studies. The study complied with the animal welfare act for humane care and use of animals. Test articles (AAV virus containing constructs) were thawed at room temperature prior to dosing, and all animals received a single intravenous (IV) 2004, injection. Table 1 below shows the study design for the testing of the constructs studied in vivo in FIG. 8 (mapped in FIGS. 4, 6 and 7). Table 2 shows the study design for the testing of the constructs outlined in FIG. 15. Doses were 1.8E+11 vg per mouse which was approximately 7E+12 vg/kg. All animals received a follow-up 200 µL intraperitoneal injection of cyclophosphamide on Days 0 and 14. Non-terminal and terminal blood collections were done as outlined in Tables 1 and 2.

Figure 9B:
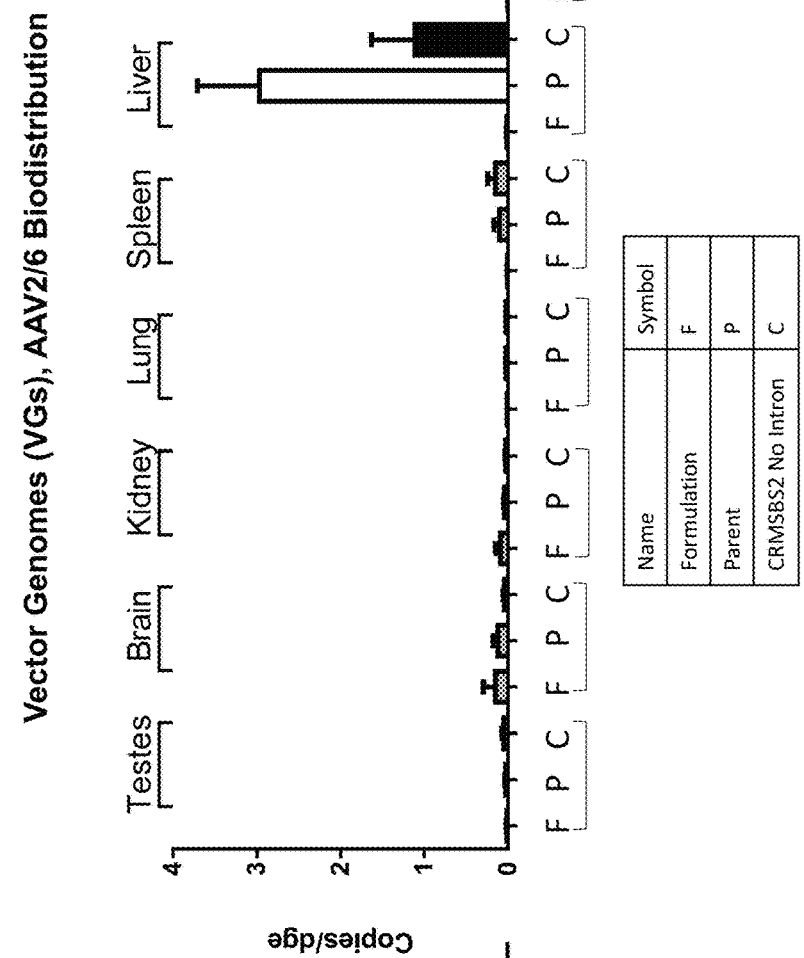
FIGS. 9A and 9B depict liver specific expression of F8-BDD cDNA following administration of vectors as described in FIG. 7.
Figure 9A:
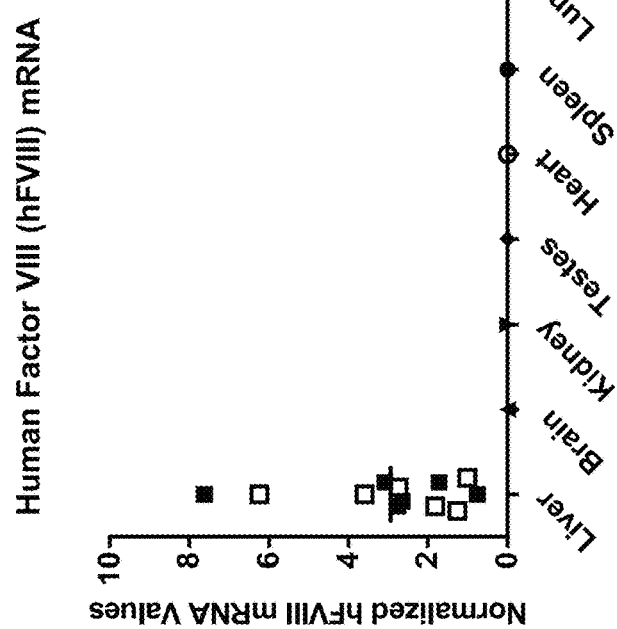
Figure 15A:
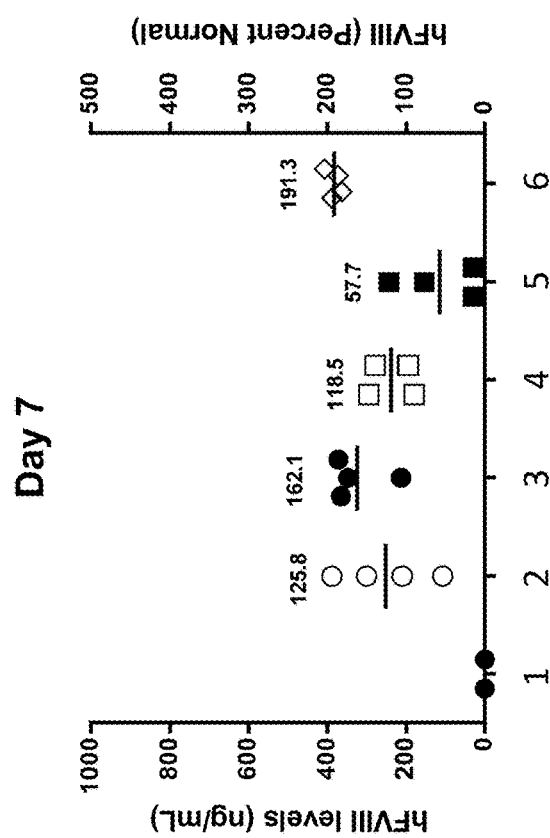
Figure 16B:
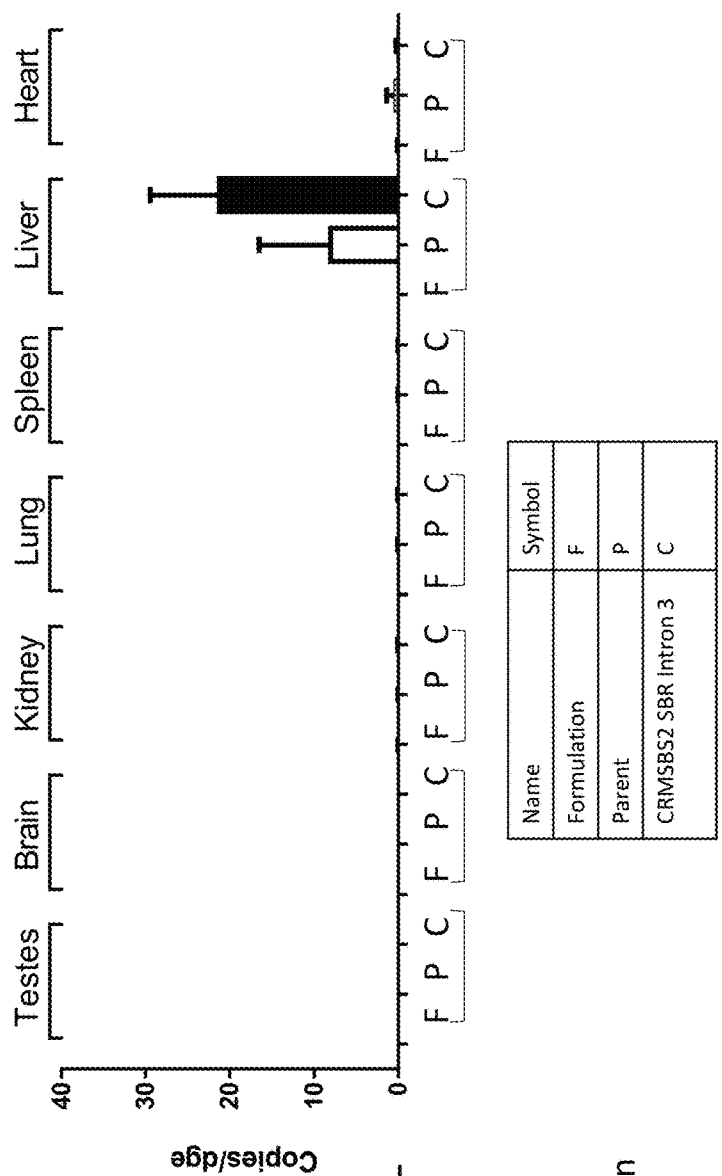
FIGS. 16A and 16B show that expression of the FVIII-BDD cDNA is liver-specific.
Figure 16A:
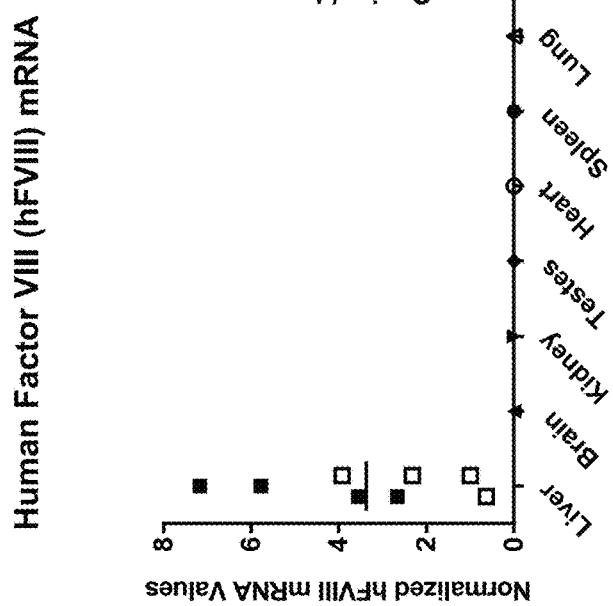

FIG. 15A) and Day 28 (FIG. 8B and FIG. 15B) after administration. Furthermore, as shown in FIGS. 9 and 16, the transgene was expressed only in liver and no other tissues (FIGS. 9A and 16A) and the AAV vector transduces primarily liver cells (vector genome biodistribution analysis as shown in FIGS. 9B and 16B). In these datasets, human factor VIII-BDD (hFVIII-BDD) mRNA was analyzed from tissues (brain, heart, kidney, lung, liver, spleen, testes) in the study represented in Table 1 by qRT-PCR as described above in Example 1. Additionally, vector genome distribution was

TABLE 1

Study design for constructs from FIGS. 4, 6 and 7 (results in FIG. 8)

| Group | Test article Description | Serotype | Immune Supp. | Dose | Total Volume/ mouse (µL) | N/Time point for serial bleed (day) | | | |
|---|---|---|---|---|---|---|---|---|---|
| | | | | | | 7 | 14 | 21 | 28 |
| 1 | Formulation | NA | 50 mg/kg | NA | 200 | 6 | 6 | 6 | 6 |
| 2 | Parent | AAV2/6 | 50 mg/kg | 1.80E+11 | 200 | 6 | 6 | 6 | 6 |
| 3 | CRMSBS1 | AAV2/6 | 50 mg/kg | 1.80E+11 | 200 | 6 | 6 | 6 | 6 |
| 4 | CRMSBS1 No Intron | AAV2/6 | 50 mg/kg | 1.80E+11 | 200 | 6 | 6 | 6 | 6 |
| 5 | CRMSBS1 T-Chimeric Intron | AAV2/6 | 50 mg/kg | 1.80E+11 | 200 | 6 | 6 | 6 | 6 |
| 6 | CRMSBS2 | AAV2/6 | 50 mg/kg | 1.80E+11 | 200 | 6 | 6 | 6 | 6 |
| 7 | CRMSBS2 No Intron | AAV2/6 | 50 mg/kg | 1.80E+11 | 200 | 6 | 6 | 6 | 6 |
| 8 | CRMSBS2 T-Chimeric Intron | AAV2/6 | 50 mg/kg | 1.80E+11 | 200 | 6 | 6 | 6 | 6 |
| | | | | | | | | | 48 |

TABLE 2

Study design for constructs from FIG. 15

| Group | Test article Description | Serotype | Immune Supp. | Dose | Total Volume/ mouse (µL) | N/Time point for serial bleed (day) | | | |
|---|---|---|---|---|---|---|---|---|---|
| | | | | | | 7 | 14 | 21 | 28 |
| 1 | Formulation | NA | 50 mg/kg | NA | 200 | 4 | 4 | 4 | 4 |
| 2 | Parent | AAV2/6 | 50 mg/kg | 1.80E+11 | 200 | 4 | 4 | 4 | 4 |
| 3 | CRMSBS2 | AAV2/6 | 50 mg/kg | 1.80E+11 | 200 | 4 | 4 | 4 | 4 |
| 4 | CRMSBS2 SBR Intron 1 | AAV2/6 | 50 mg/kg | 1.80E+11 | 200 | 4 | 4 | 4 | 4 |
| 5 | CRMSBS2 SBR Intron 2 | AAV2/6 | 50 mg/kg | 1.80E+11 | 200 | 4 | 4 | 4 | 4 |
| 6 | CRMSBS2 SBR Intron 3 | AAV2/6 | 50 mg/kg | 1.80E+11 | 200 | 4 | 4 | 4 | 4 |
| | | | | | | | | | 24 |

Blood was collected from all mice on Days 7, 14, 21 (non-terminal) and Day 28 (terminal). All blood was collected into tubes containing sodium citrate and processed to plasma. Non-terminal blood collections were collected via the submandibular vein or the retro-orbital sinus. Blood collections at the time of sacrifice were collected via cardiac puncture or vena cava. The plasma was separated and stored at −60 to −80° C. until use in the ELISA assay described below.

All animals were sacrificed at Day 28 and the liver, spleen, testes, brain, heart, lung and kidneys were collected and weighed. The left lateral lobe of the liver was separated and divided into 3 pieces and snap frozen in liquid nitrogen separately from the rest of the liver. The remaining liver lobes and other tissues (whole) were snap frozen in liquid nitrogen. Frozen specimens were stored at −60 to −80° C. until processing for RNA/DNA extraction.

Figure 8A:
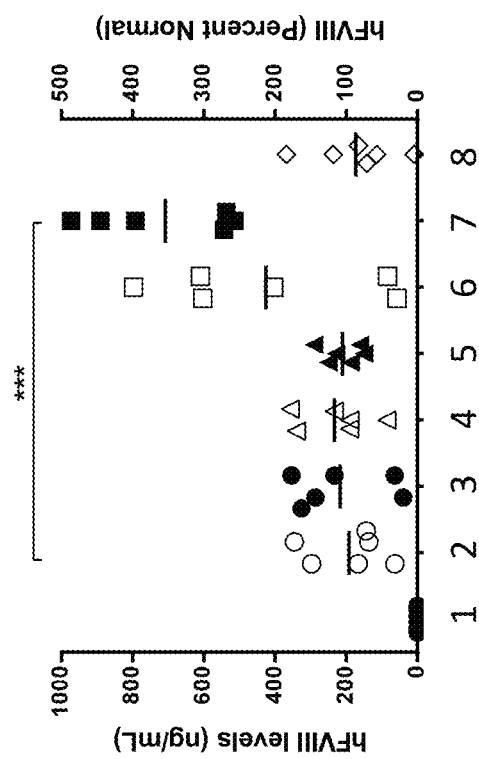

As shown in FIGS. 8 and 15, all constructs tested resulted in in vivo production of the transgene (human secreted Factor VIII B-domain deleted) in vivo at Day 7 (FIG. 8A and analyzed in these same tissues by qPCR (see Example 1) and the results are shown in FIGS. 9B/16B. These data demonstrate that the AAV2/6 vector primarily transduce the liver.

The constructs designed to examine the efficacy of intron modifications were tested in vivo as well in a study outlined in Table 2, and the data for days 7 and at peak levels are shown in FIG. 15. hFVIII-BDD mRNA was also analyzed (FIG. 16A) as was vector genome distribution (FIG. 16B) and showed that hF8 mRNA expression was liver specific, and AAV2/6 primarily transduces liver.

Thus, the constructs described herein provide for robust transgene expression following hepatic delivery.

Figure 23:
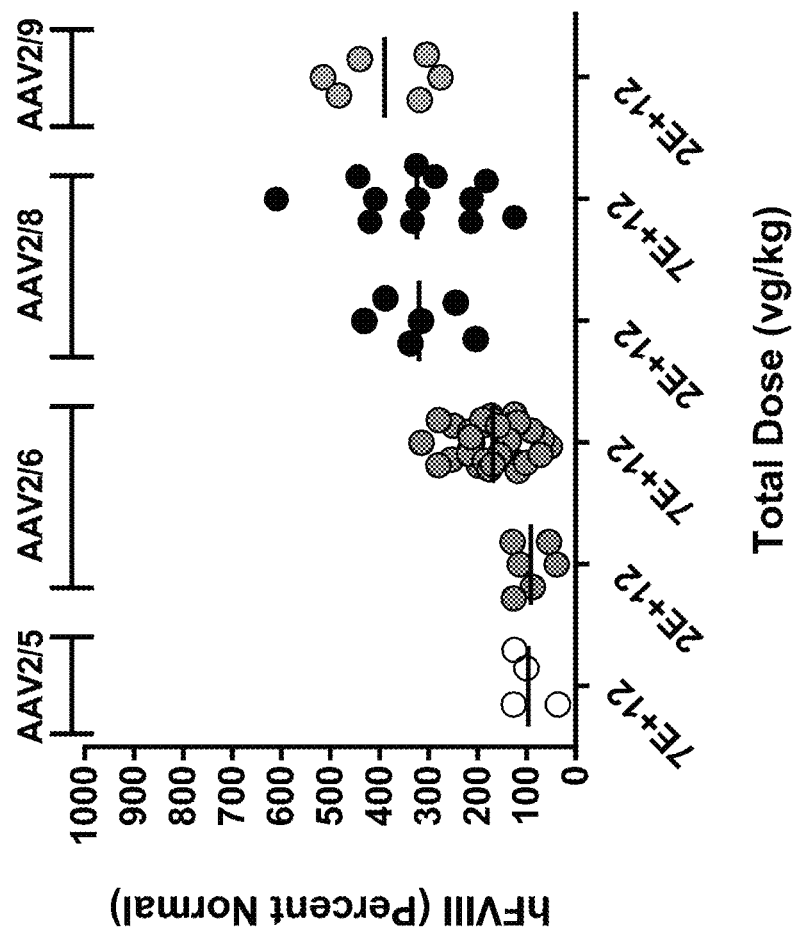
FIG. 23 is a graph depicting hFVIII-BD production levels in wild type mice using multiple AAV serotypes as shown. Male C57BL/6 mice were intravenously injected with 6E+10 vg/mouse (~2E+12 vg/kg) for the AAV2/5 and AAV2/9 constructs, or 6E+10 vg/mouse (~2E+12 vg/kg) and 1.8E+11 vg/mouse (~7E+12 vg/kg) for the AAV2/6 and AAV2/8 constructs. The figure demonstrates supraphysiological hFVIII-BDD detected in the plasma of all samples except some of the lower doses of AAV2/6 and AAV 2/5.

An additional study was carried out to test if the levels of hFVIII-BDD observed in vivo were sensitive to the serotype of the AAV being used. Male C57BL/6 mice were intravenously injected with 6E+10 vg/mouse (~2E+12 vg/kg) or 1.8E+11 vg/mouse (~7E+12 vg/kg) of the AAV2/5, AAV2/6, AAV2/8 or AAV2/9 F8 parent cDNA. Transducing mice with serotype AAV2/6, known to be inefficient at transducing mouse liver, at 6E+10 vg/mouse (~2E+12 vg/kg) mean peak value of 91.9%+/−15.5 SEM (n=6) of normal hFVIII plasma levels in humans was achieved. At a higher dose representing ~7E+12 vg/kg mean peak value of hFVIII plasma over six independent in vivo mouse studies of 169.2%+/−10.1 SEM (n=36) was achieved. Mean peak levels for AAV2/8 at 2E+12 vg/kg were 320% and 323.6% at 6E+12 vg/kg. For AAV2/9 at 2E+12 vg/kg mean peak levels were 389.6% (see FIG. 23, also showing results using AAV2/5 and AAV2/6).

Figure 24:
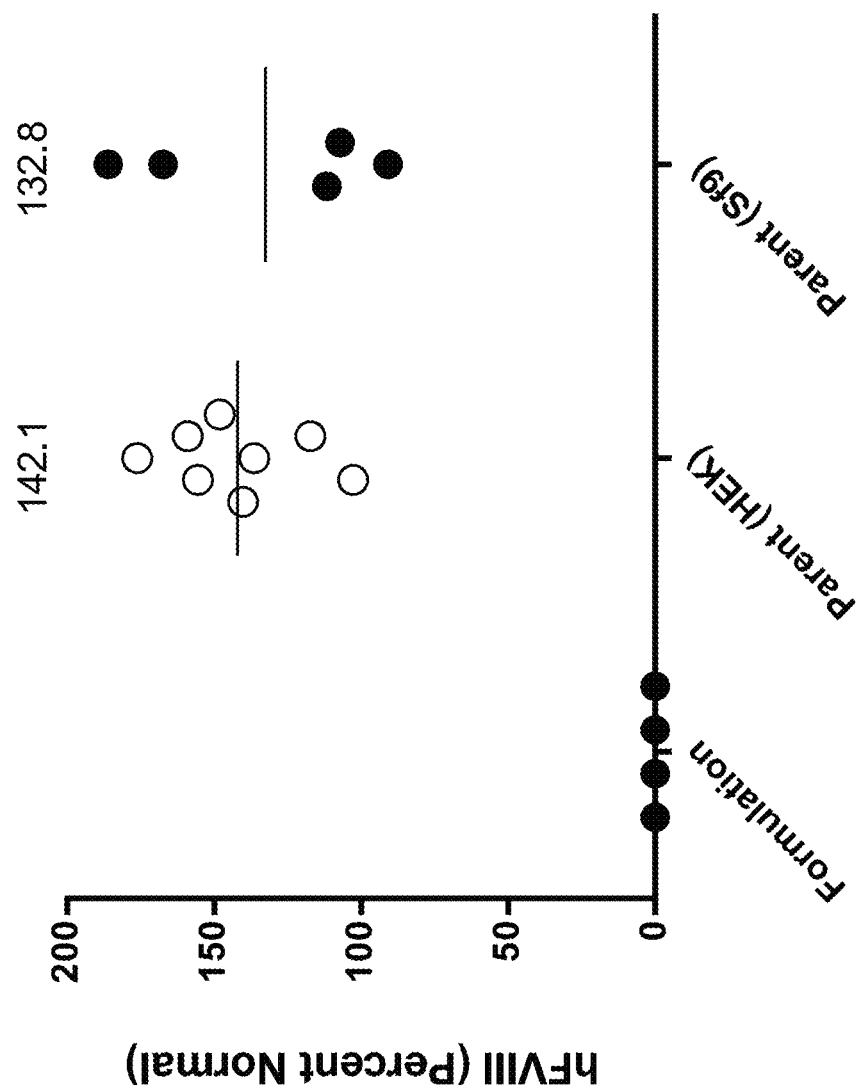
FIG. 24 is a graph depicting the relative expression of the hFVIII-BDD transgene in wild type mice when the transgene was delivered via AAV2/6 purified by either HEK293 production (HEK) or by baculoviral production in Sf9 cells (Sf9). The transgene used with the F8 parent cDNA (FIG. 4). Male C57BL/6 mice were administered parent F8 parent cDNA via IV injection (tail vein) with 1.8E+11 vg/mouse (~7E+12 vg/kg) of the AAV2/6 F8 parent cDNA produced from either HEK293 cells or SP9/rBV (recombinant baculovirus). Treatment with F8 parent cDNA from HEK293 cells achieved a mean peak value of 142.1%±8.3% SEM (n=8) (measured by hFVIII ELISA) of normal human FVIII plasma levels. A similar level of 132.8%±18.6% SEM (n=5) (measured by hFVIII ELISA) was achieved following administration of F8 parent cDNA (Sf9/rBV) to mice.

Studies were also conducted to determine if the production method used to generate the AAV had an impact on the hFVIII-BDD expression achieved in vivo. Male C57BL/6 mice were administered parent F8 parent cDNA via IV injection (tail vein) with 1.8E+11 vg/mouse (~7E+12 vg/kg) of the AAV2/6 F8 parent cDNA produced from either HEK293 cells or Sf9/rBV (recombinant baculovirus). Treatment with F8 parent cDNA from HEK293 cells achieved a mean peak value of 142.1%±8.3% SEM (n=8)(measured by hFVIII ELISA) of normal human FVIII plasma levels. A similar level of 132.8%±18.6% SEM (n=5) (measured by hFVIII ELISA) was achieved following administration of F8 parent cDNA (Sf9/rBV) to mice (FIG. 24).

Figure 25A:
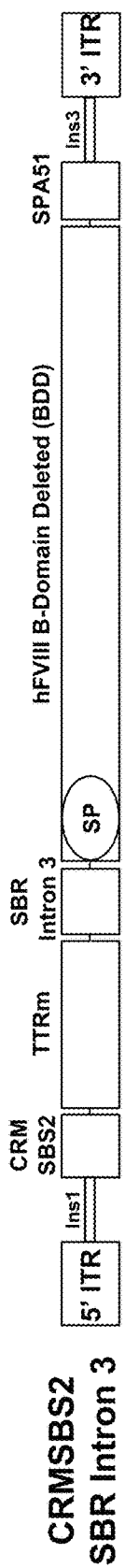
FIGS. 25A and 25B show the expression level in mice of the CRBSBS2 SBR Intron 3 (Ins1-Ins3) cDNA transgene donor.
Figure 25B:
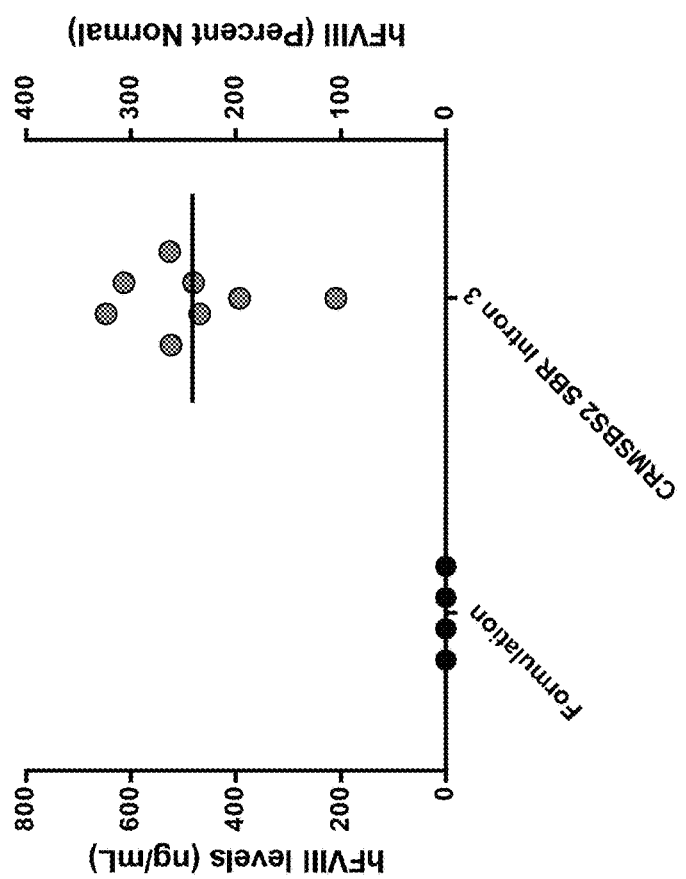

The studies were repeated for comparison purposes with the F8 CRMSBS2 SBR Intron 3 cDNA (see FIG. 10). Male C57BL/6 mice were intravenously injected with 1.8E+11 vg/mouse (~6E+12 vg/kg) of AAV2/6 CRMSBS2 SBR Intron 3 cDNA (n=8). Shown are mean peak levels of hFVIII in the plasma of C57BL/6 mice as measured by hFVIII ELISA (FIG. 25).

Figure 17A:
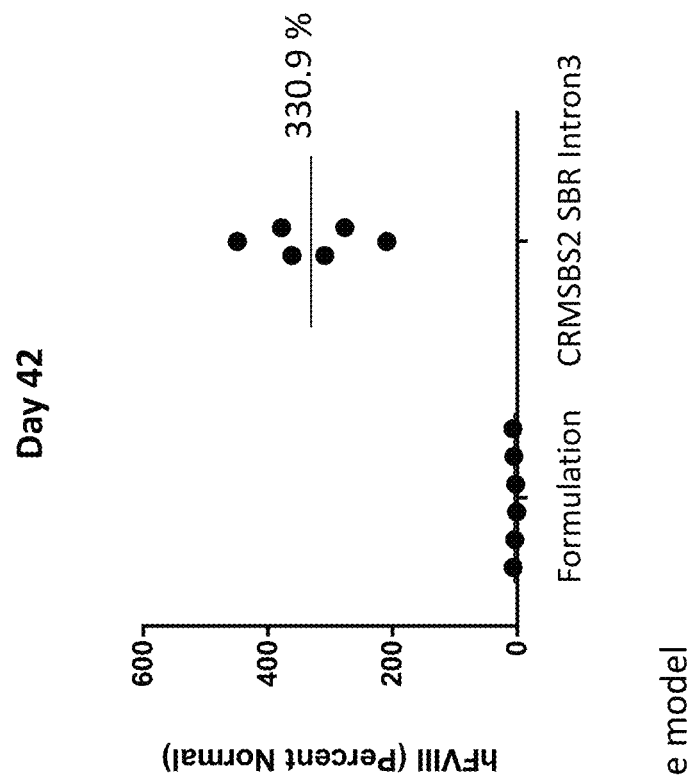
FIGS. 17A and 17B depict the supraphysiological levels of enzymatically active human Factor VIII-BDD in the plasma of Hemophilia A mice.
Figure 17B:
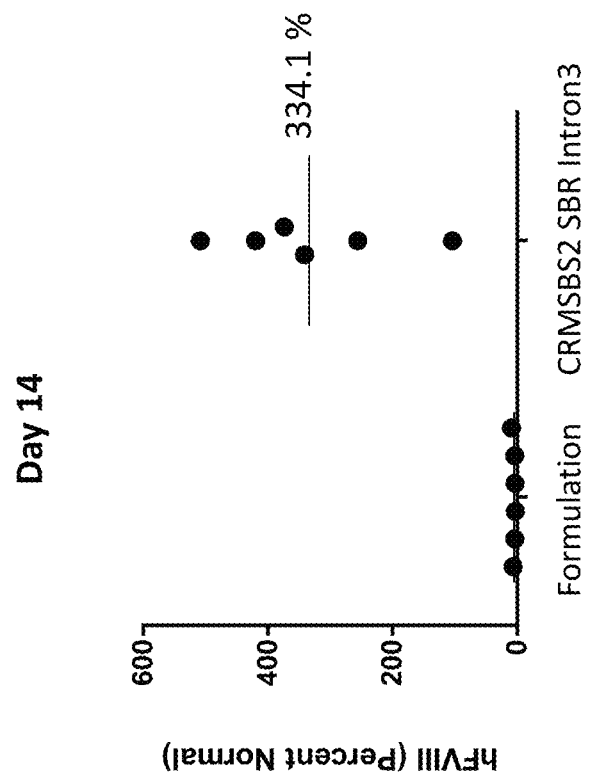
Figure 18:
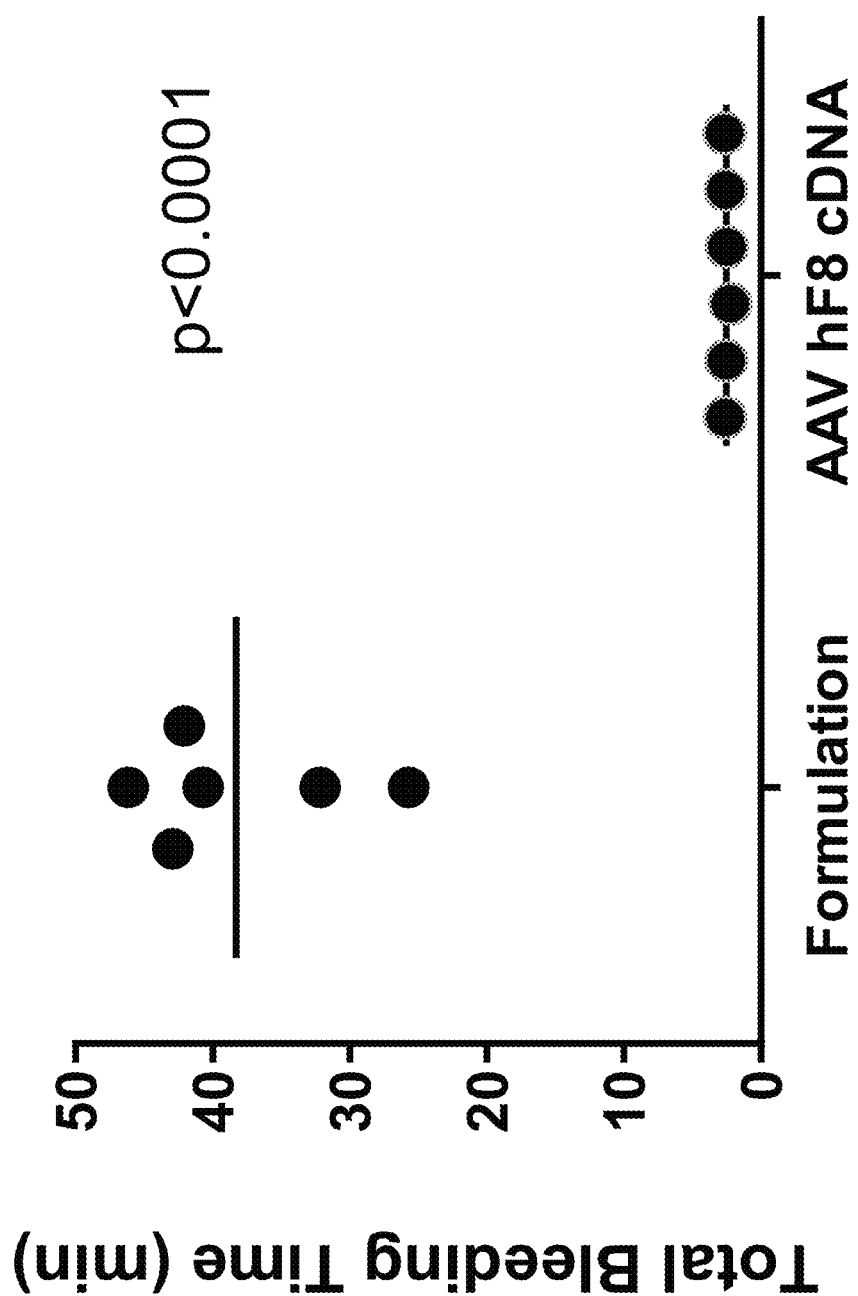
FIG. 18 is a graph showing bleeding times in hemophilia A R593C mice treated with F8 CRMSBS2 SBR Intron 3 cDNA. The results demonstrate a significant reduction in the amount of time to achieve hemostasis (p<0.0001) in the hemophilia mice following tail vein transection.
Figure 19:
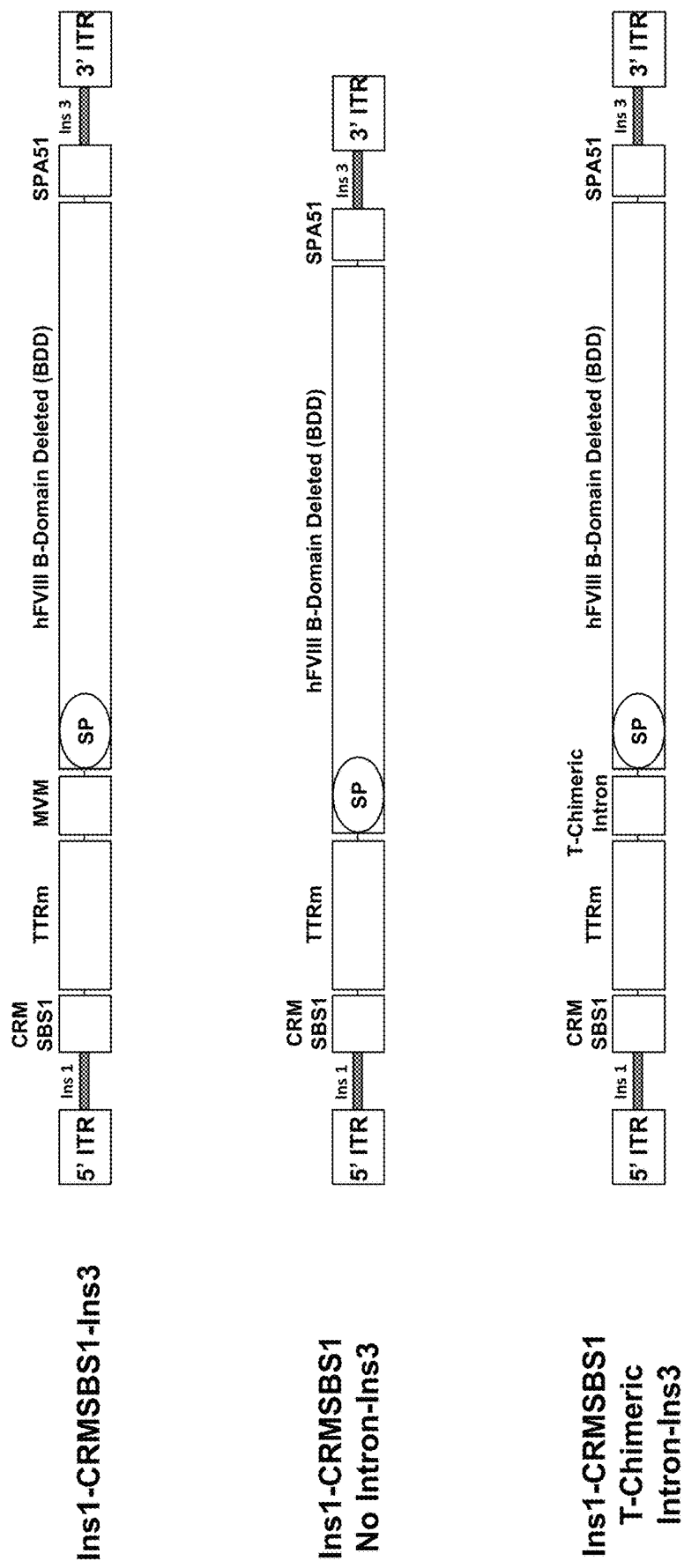
FIG. 19 is a schematic depicting CRMSBS1, and new exemplary constructs with no MVM intron, or a chimeric intron, together with a Factor VIII B-domain deleted transgene and Ins1-Ins3. CRM refers to cis-regulatory element. SBS refers to Sangamo Biosciences. hFVIII refers to human factor VIII. SP refers to signal peptide. ITR refers to inverted terminal repeat. SPA refers to synthetic poly adenylation sequence. "Ins1" and "Ins3" are as described above in FIG. 2.
Figure 20:
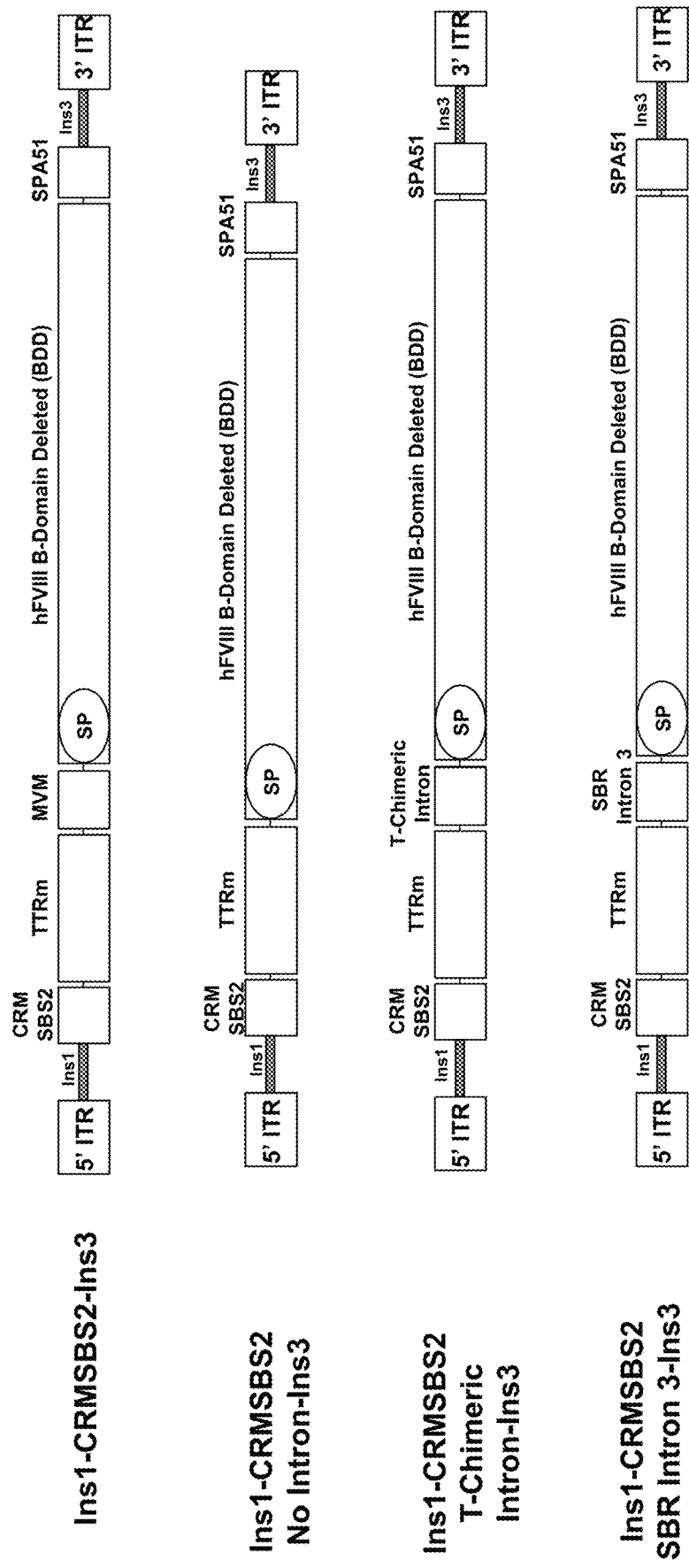
FIG. 20 is a is a schematic depicting CRMSBS2, and new exemplary constructs with no MVM intron, a chimeric intron, or SBR Intron 3 together with a Factor VIII B-domain deleted transgene and Ins1-Ins3. CRM refers to cis-regulatory element. SBS refers to Sangamo Biosciences. hFVIII refers to human factor VIII. SP refers to signal peptide. ITR refers to inverted terminal repeat. SPA refers to synthetic poly adenylation sequence. "Ins1" and "Ins3" are as described above in FIG. 2.

Hemophilia A Mice:

The constructs were also tested in the R593A mouse model of Hemophilia A (Bril et al (2006) *Thromb Haemost* 95(2):341-7; Chavez et al., (2012) *Hum Gen Ther* 23(4): 390). These mice carry a knock out of the endogenous murine F8 gene. In addition, they carry a mutant human FVIII-R593C transgene under the control of a murine albumin promoter such that they express undetectable amounts of the mutant human protein but are thought to be tolerant to human FVIII expression because of the trace amounts of mutant FVIII R593A protein produced. The original strain was FVB but has been back-crossed to C57BL/6 mice for at least 5 generations at Jackson Laboratory. The study complied with the animal welfare act for humane care and use of animals. Test articles were thawed at room temperature prior to dosing, and all animals received a single intravenous (IV) 200 μL injection. Doses were 1.8E+11 vg per mouse which was approximately 7E+12 vg/kg. The study design is shown below in Table 3:

FVIII protein found in normal human plasma at both days 14 (FIG. 17A) and 42 (FIG. 17B).

To test functionality and therapeutic efficacy of the hFVIII in the mouse Hemophilia A model, a tail vein transection (TVT) model was used. In brief, mice were initially anaesthetized with isoflurane, and anesthesia was maintained via an anesthesia mask for the study duration. Immediately following anesthesia induction, the mice were placed on a heating pad (set to 37° C.) with the temperature sensor between the stomach and the heating pad ensuring the head was positioned properly in the anesthesia mask. Using a marker block for measurement, the tail was marked with a marker pen at "12 o'clock" corresponding to exactly 2.5 mm in diameter where after the tail was submerged into a saline collection tube (37° C. saline). The tail was submerged in the temperature saline for a total of 10 minutes before induction of the bleed. The tail was then placed in the cutting block with the mark from "13" pointing at "15 o'clock" approximately ten seconds before the cut was made (to facilitate transection of the left lateral tail vein). At exactly t=0 minutes, the tail was cut with a one mm deep cut placed laterally on the left side of the mouse tail thereby transecting the lateral tail vein. Immediately following the tail was immersed in the pre-warmed saline collection tube. The primary bleeding episode was recorded for three minutes. If the primary bleed was greater than three minutes, the animal was euthanized and replaced. At three minutes post injury, the collection tube was exchanged with a new pre-warmed saline collection tube. All secondary bleeding episodes were recorded for an additional 57 minutes. If the bleeding stopped at 15, 30, or 45 min, the wound was challenged by gently wiping twice with a saline wetted gauze swab. Immediately following the challenge, the tail was re-submerged into the saline. At t=60 minutes the mice were euthanized while still under full anesthesia. Bleeding time was reported as the sum of primary and secondary bleeding times. Primary and secondary bleeds were lysed and stored for later hemoglobin measurements for blood loss. (Johansen et al., *Haemophilia*, (2016) doi: 10.1111/hae.12907).

The results demonstrate a significant reduction in the amount of time to achieve hemostasis (p<0.0001) in the Hemophilia A R593C mice following tail vein transection (FIG. 18), demonstrating therapeutic efficacy in these mice.

Non-Human Primates:

Experiments were carried out in NHP using the hFVIII-BDD cDNA constructs where AAV2/6 and AAV2/8 serotypes were evaluated. Table 4 below and FIG. 26B show the identity of the dosing groups. The difference between the F8

TABLE 3

CRMSBS2 SBR Intron 3 in Hemophilia A mutant mice

| Group | Test Article Description | Serotype | Immune Supp. | Dose | Total Volume/ mouse (μL) | Time point for serial bleed (days) | | | | | | |
|---|---|---|---|---|---|---|---|---|---|---|---|---|
| | | | | | | 8 | 14 | 21 | 28 | 35 | 42 | Sac |
| 1 | Formulation buffer | NA | N/A | N/A | 200 | 6 | 6 | 6 | 6 | 6 | 6 | 6 |
| 2 | CRMSBS2 SBR Intron 3 | AAV2/6 | N/A | 1.80E+11 | 200 | 6 | 6 | 6 | 6 | 6 | 6 | 6 |
| | | | | | | | | | | | | 12 |

The study was carried out for three months, representative results of the three month study are shown, both a day 14 and at day 42 results (FIG. 17) show that the FVIII-BDD transgene was expressed at levels >300% of the levels of transgene expression cassette designed "cDNA 1" (Groups 2-4 of Table 4 below) and "cDNA2" (Group 5 of Table 4 below) is that the "cDNA2" donor had a slightly different promoter module (hybrid liver promoter, see McIntosh et al (2013) Blood 121(17):3335), but the rest of the F8-BDD transgene expression cassette (including the coding region) was the same. For these experiments, the dosing regimen outlined in FIG. 26A was used (where the rituximab was administered pre-test article and the steroid (administered concurrently with the test article and daily thereafter).

TABLE 4

NHP groups with FVIII transgene cassette

| Group No. | No. of Males[a] | Test Article Identification | AAV Transgene Description | Serotype | Component Dose Level (vg/kg) | Total AAV Vector Dose Level (vg/kg) |
|---|---|---|---|---|---|---|
| 1 | 2 | SGMO.01 | Formulation Buffer | NA | NA | NA |
| 2 | 3 | SGMO.02 | hF8-BDD cDNA 1 | AAV2/6 | 2E+12 | 2E+12 |
| 3 | 3 | SGMO.03 | hF8-BDD cDNA 1 | AAV2/6 | 6E+12 | 6E+12 |
| 4 | 3 | SGMO.04 | hF8-BDD cDNA 1 | AAV2/8 | 6E+12 | 6E+12 |
| 5 | 3 | SGMO.05 | hF8-BDD cDNA 2 | AAV2/8 | 6E+12 | 6E+12 |

Figure 27:
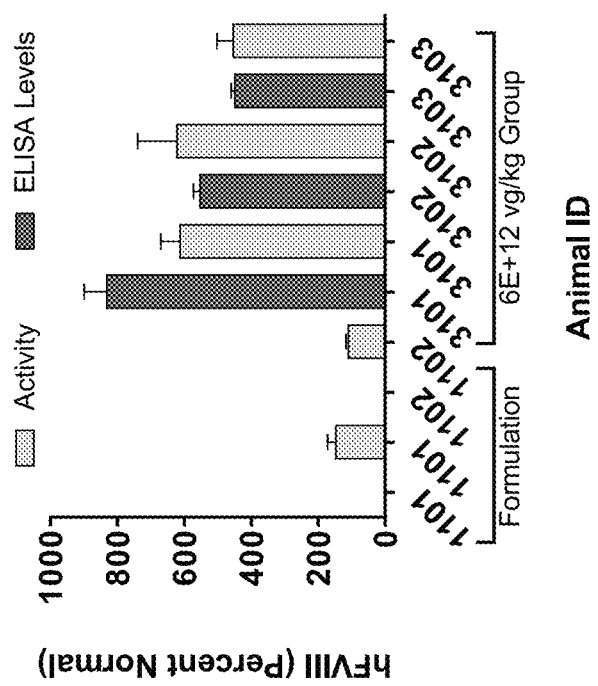
FIG. 27 is a graph showing the correlation between hFVIII activity and levels in NHPs treated with AAV2/6 hF8 cDNA. Cynomolgus monkeys were administered formulation buffer or 6E+12 vg/kg of AAV2/6 hF8 cDNA (parent vector).
Figure 29A:
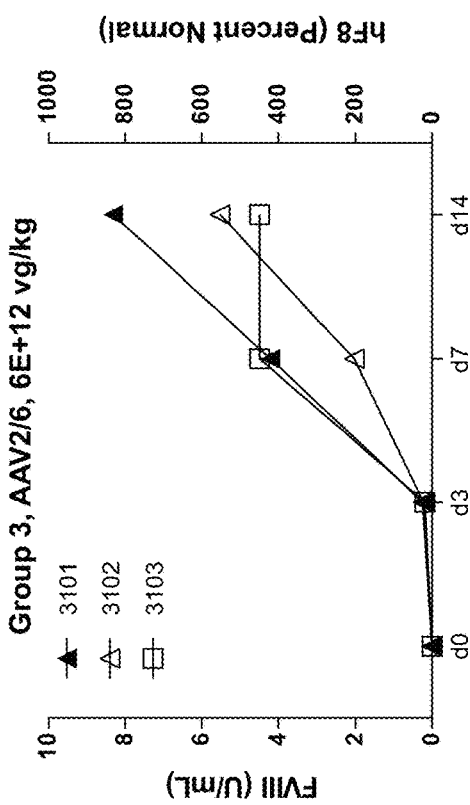
FIGS. 29A through 29D are graphs depicting a summary of human FVIII plasma levels for the NHP study using AAV donors carrying Factor VIII (F8) B-Domain Deleted (FVIII-BDD) proteins.
Figure 29C:
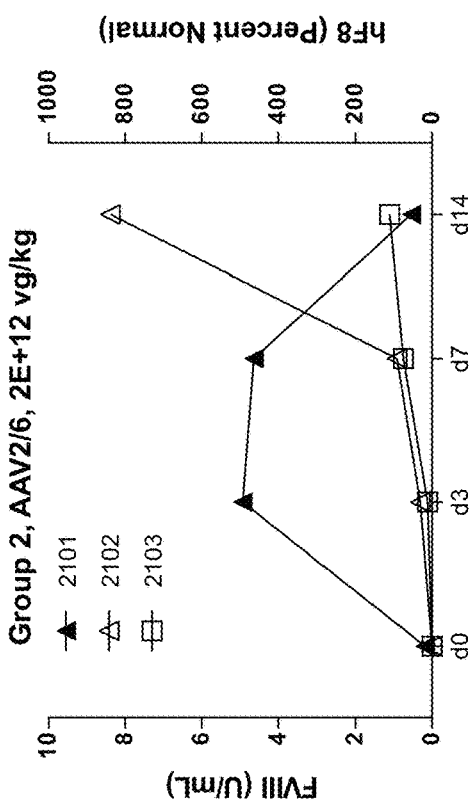
Figure 29B:
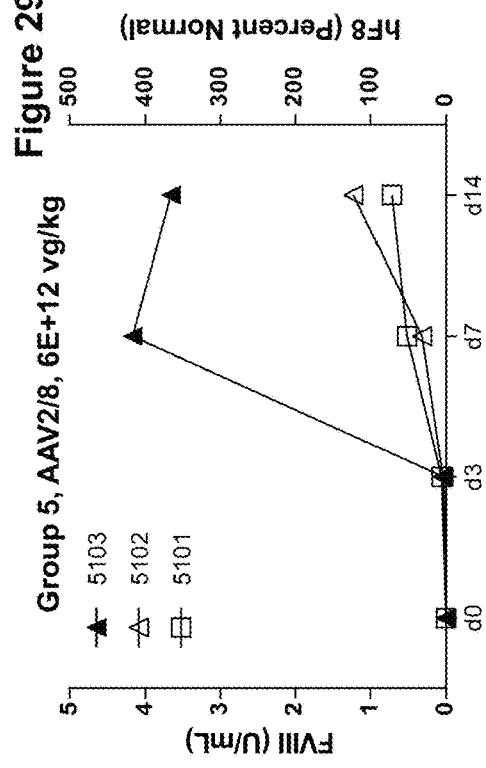
Figure 29D:
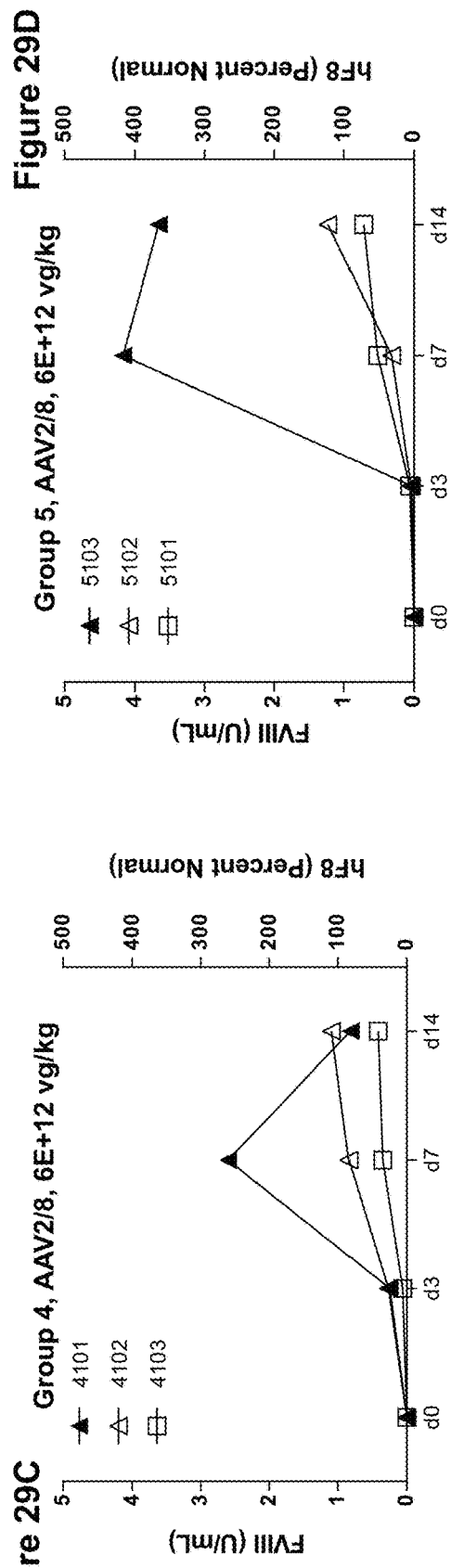

Cynomolgus monkeys were administered formulation buffer or 6E+12 vg/kg of AAV2/6 hF8 cDNA (parent). At day 14 following test article addition, circulating levels and activity of hFVIII were analyzed by ELISA or clotting activity (see FIG. 27). Normal levels of Cynomolgus monkey FVIII are ~1U/mL reflected in the clotting activity data for the formulation control group as the clotting activity assay is not specific for human FVIII. The ELISA is specific for human FVIII over Cynomolgus monkey FVIII thus, as expected there is no hFVIII levels as measured by ELISA in the formulation control group. Shown are individual animals for the formulation control group (Group 1, animal IDs 1101-1102), and the 6E+12 vg/kg dose group (Group 3, animal IDs 3101-3103). In the Group 3 animals there are supraphysiological levels and activity of circulating hFVIII, upwards of 8U/mL.

As an indicator of liver condition following treatment, liver enzymes were measured for the formulation control group (Group 1, animal ID 1101), and the 6E+12 vg/kg dose group (Group 3, animal ID 3102). Alanine aminotransferase (ALT) and aspartate aminotransferase (AST) were measured. The acceptable upper limit reference values for Cynomlogus monkeys for ALT is 126 U/L and 120 U/L for AST. For both the formulation control group and the 6E+12 vg/kg AAV hF8 cDNA (parent) group ALT/AST levels were elevated post-liver biopsy (liver biopsy was on day 41), denoted by an asterisk. Otherwise AAV hF8 cDNA was well-tolerated over the entirety of the study (247 days) (see FIGS. 28A and 28B).

The data is presented in FIG. 29, were the data set for each monkey is depicted on the graphs. The data indicates that the higher doses (compare FIG. 29A with FIG. 29B) of test article in the AAV6 serotype background gave expression of FVIII-BDD at nearly 10× the level found in normal human plasma. The data for test article in the AAV2/8 serotype showed an increase in the FVIII activity, but not to the same extent as was observed for AAV2/6.

Figure 30:
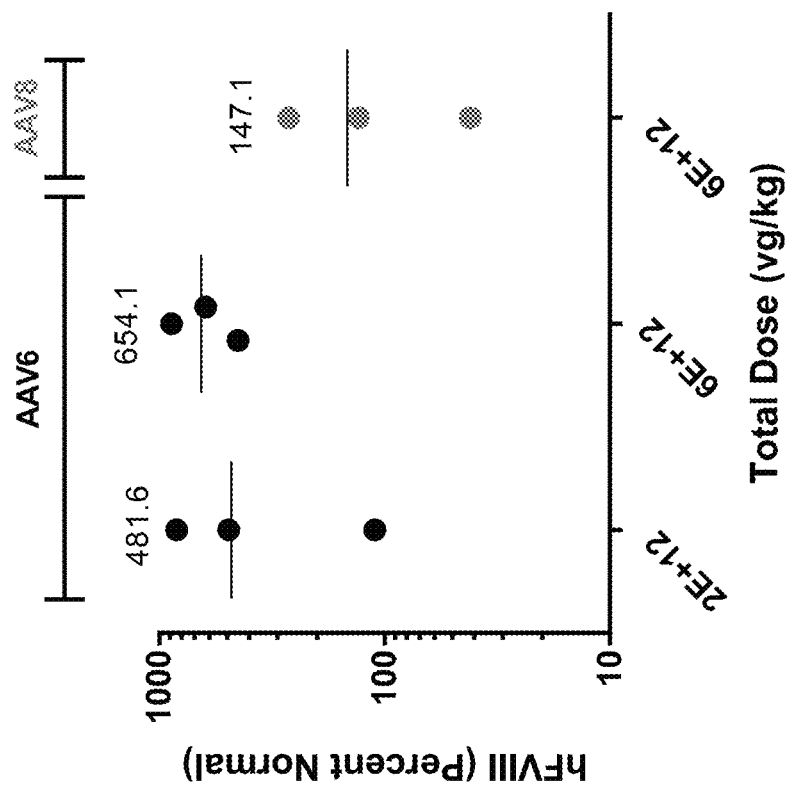
FIG. 30 is a graph depicting the peak human FVIII antigen levels over the study following treatment in non-human primates (NHP) with the indicated constructs (in AAV6 or AAV8 vectors). At dose levels of 2E+12 vg/kg (n=3), peak values of 111.0%, 493.9% and 840.0% (overall mean 481.6% as measured by hFVIII ELISA) of normal hFVIII plasma levels in humans were achieved. At a higher dose representing 6E+12 vg/kg (n=3), peak values of 450.0%, 625.6% and 886.7% [overall mean 654.1%] of hFVIII plasma levels were achieved. Overall mean value for AAV8 was 147.1%.

Subsequent to the initial 14 day period described above, the experiment was continued up to 247 days post the single dose of the AAV-FVIII-BDD. The co-dosing of the steroid was stopped at day 103. Determination of the hFVIII-BDD levels in the plasma of the monkeys was determined using a custom ELISA as follows. 96-well half-area HB (high binding) polystyrene microplates (Corning) were coated overnight at 4° C. with mouse monoclonal anti-hFVIII antibody (Green Mountain, Burlington, Vt.) in 0.2 M carbonate bicarbonate buffer pH 9.4 (Thermo Fisher Scientific, Waltham Mass.). The following day the plates were washed four times using 1×TBST (Thermo Fisher Scientific, Waltham Mass.). 96-well plates were then blocked two hours at room temperature using 3% BSA/TBS blocking buffer, followed by washing four times with 1×TBST. Plasma was added to the plate and incubated with rocking at room temperature for two hours, followed by washing four times with 1×TBST. Detection antibody, biotinylated monoclonal mouse anti-FVIII antibody (Green Mountain, Burlington, Vt.) was added and incubated for one hour at room temperature, followed by washing four times with 1×TBST. Streptavidin HRP (Jackson ImmunoResearch, West Grove Pa.) was added and incubated for one hour at room temperature followed by washing four times with 1×TBST. TMB Ultra (Thermo Fisher Scientific, Waltham Mass.) was added and allowed to develop for ten minutes, reaction was stopped with stop solution and absorbance read at 450 nM using a plate reader. Background absorbance readings were negligible (typically 0). The presence of inhibitory anti-FVIII antibodies were determined using a Bethesda assay (for example, see Kasper et al (1975) *Thromb Diath Haemorrh* 34:869-72). The ELISA assay was used to evaluate peak human FVIII antigen levels over the study. At dose levels of 2E+12 vg/kg (n=3), peak values of 111.0%, 493.9% and 840.0% (overall mean 481.6% as measured by hFVIII ELISA) of normal hFVIII plasma levels in humans were achieved. At a higher dose representing 6E+12 vg/kg (n=3), peak values of 450.0%, 625.6% and 886.7% [overall mean 654.1%] of hFVIII plasma levels were achieved (FIG. 30).

Figure 31C:
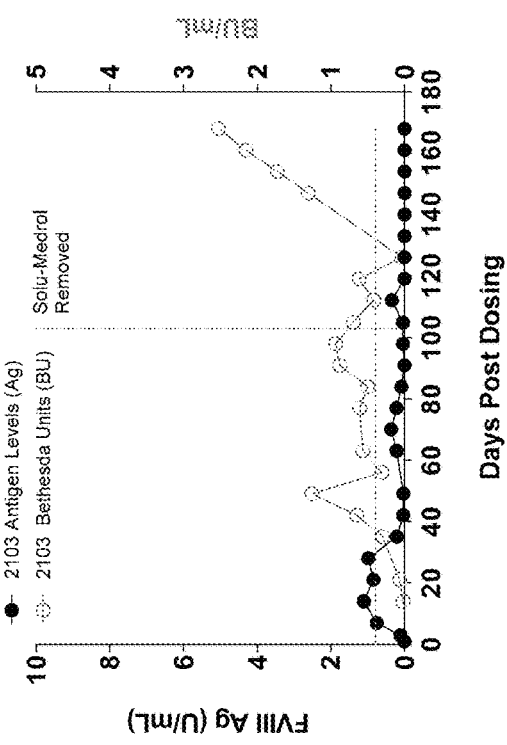
FIGS. 31A through 31C are graphs depicting the results from individual cynomolgus monkeys (n=3; animals 2101, 2102 and 2103) dosed with the low dose (2E+12 vg/kg, Group 2) of AAV2/6-FVIII-BDD cDNA over a time period of 168 days post dosing. In all three graphs, concentrations of FVIII-BDD in the plasma, as measured through ELISA, are shown in black. Additionally, concentrations of neutralizing anti-FVIII antibody (shown as Bethesda Units) in plasma are shown in grey. The dotted horizontal line represents the Bethesda Unit cutoff point, below which values would not be considered positive for anti-FVIII neutralizing antibodies. The Solu-Medrol was stopped at day 103 as indicated by the vertical dashed line. Each graph shows the results for a single monkey.
Figure 31A:
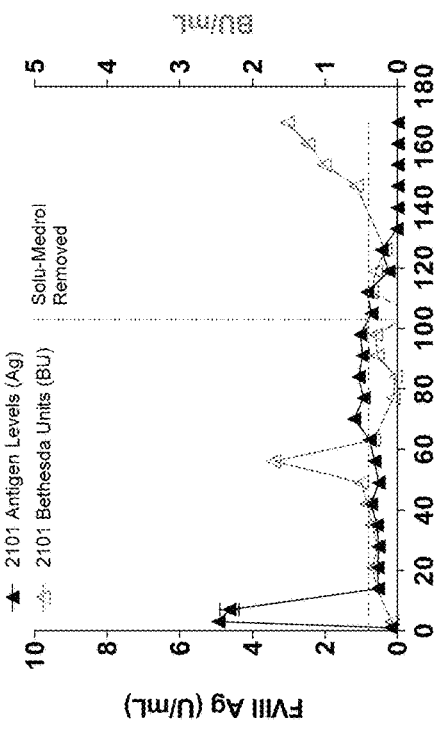
Figure 31B:
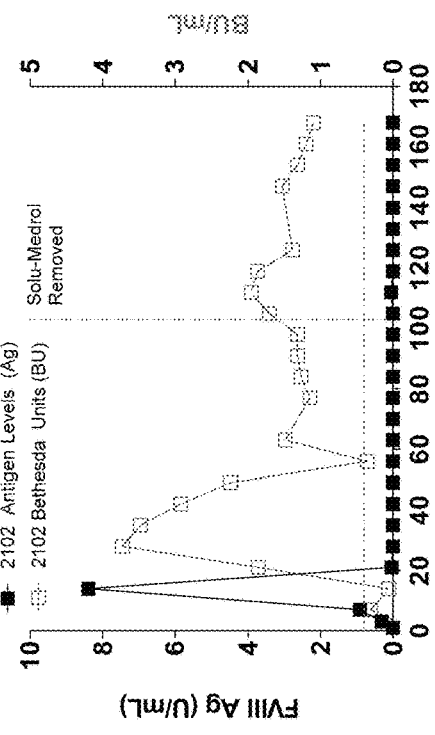

The study outlined in Table 4 was carried out and levels of FVIII-BDD and any inhibitory anti-FVIII antibodies were measured. For the low dose animals (n=3), comprising the FVIII-BDD cDNA in AAV2/6, dosed at 2E+12 vg/kg, following detection of robust hFVIII antigen levels (Ag), hFVIII-BDD levels decreased with a concomitant increase in Bethesda Units (BU). BU decreased over time and the hFVIII Ag increased (FIG. 31). The results demonstrated that following the cessation of the immunosuppressive therapy, the levels (as measured by ELISA) of human FVIII antigen dropped.

Figure 32A:
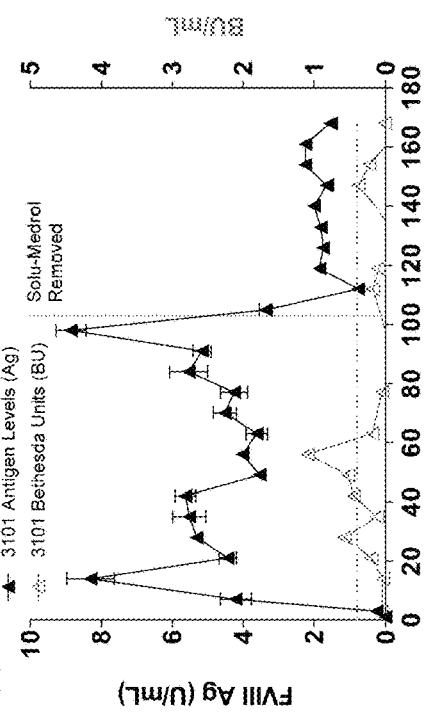
FIGS. 32A through 32C are graphs depicting the results from individual cynomolgus monkeys (n=3, animals 3101, 3102 and 3103) dosed with the high dose (6E+12 vg/kg, Group 3) of AAV2/6-FVIII-BDD cDNA over a time period of 168 days post dosing. In all three graphs, concentrations of FVIII-BDD in the plasma, as measured through ELISA, are shown in black. Additionally, concentrations of neutralizing anti-FVIII antibody (shown as Bethesda Units) in plasma are shown in grey. The dotted horizontal line represents the Bethesda Unit cutoff point, below which values would not be considered positive for anti-FVIII neutralizing antibodies. The Solu-Medrol was stopped at day 103-indicated by the vertical dashed line. Each graph shows the results for a single monkey.
Figure 32B:
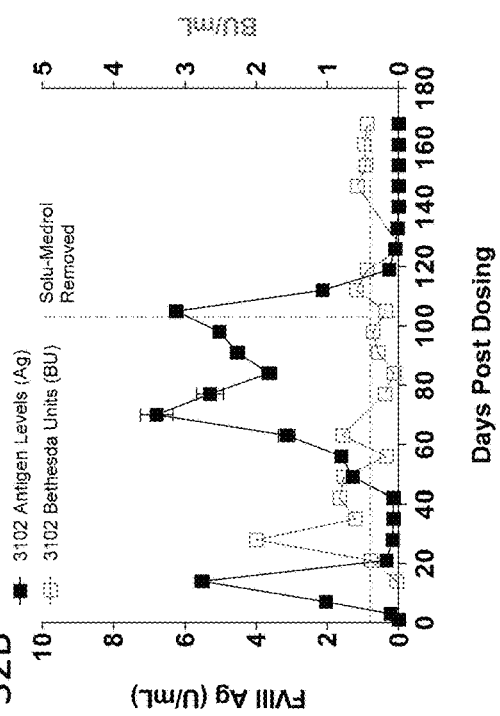
Figure 32C:
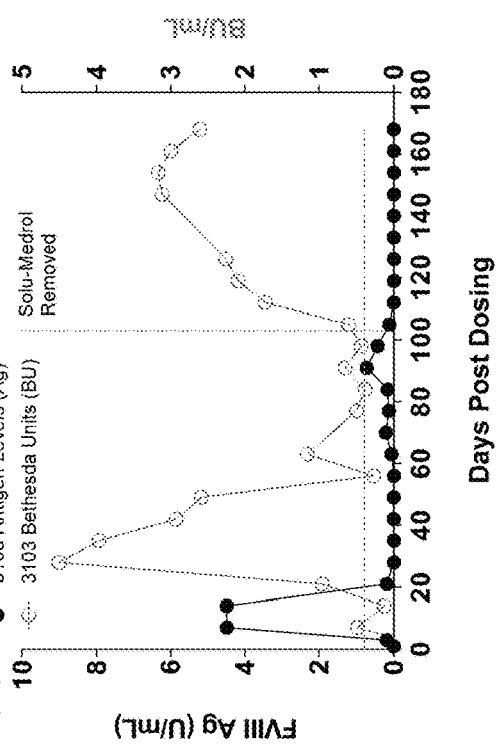
Figure 33A:
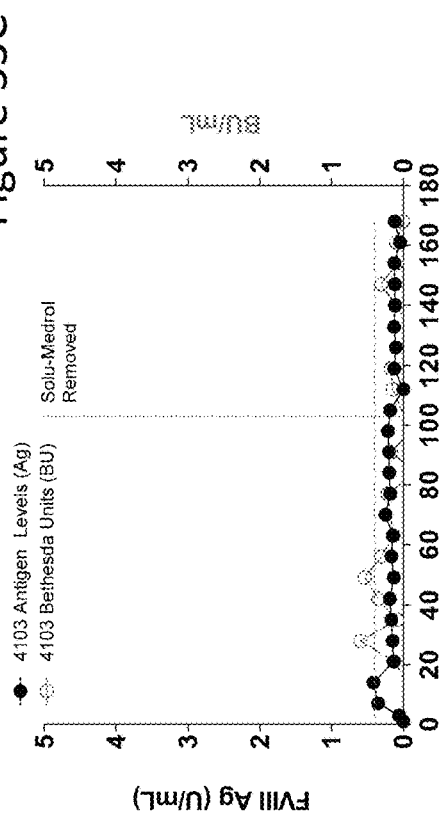
FIGS. 33A through 33D are graphs depicting the results from individual cynomolgus monkeys (n=3, animals 4101, 4102, and 4103) dosed with the high dose (6E+12 vg/kg, Group 4) of AAV2/8-FVIII-BDD cDNA over a time period of 168 days post dosing. In graphs 33A-33C, concentrations of FVIII-BDD in the plasma, as measured through ELISA, are shown in black. Additionally, concentrations of neutralizing anti-FVIII antibody (shown as Bethesda Units) in plasma are shown in grey.
Figure 33C:
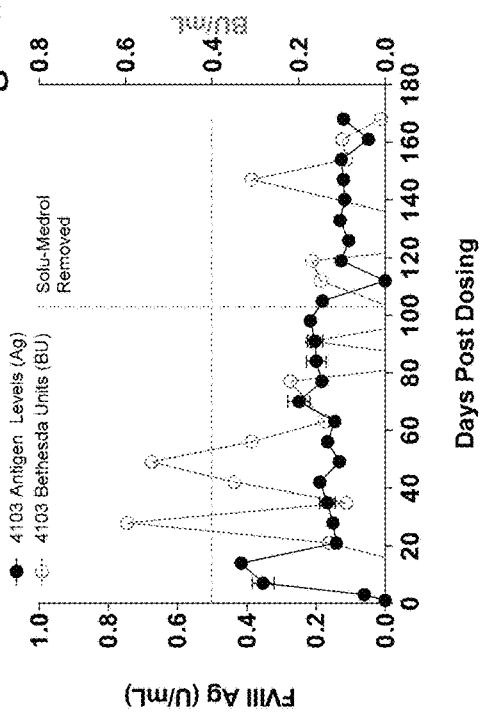
Figure 33B:
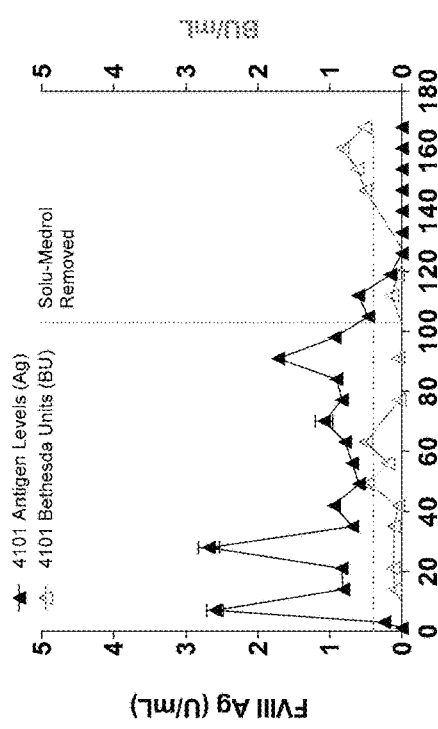
Figure 33D:
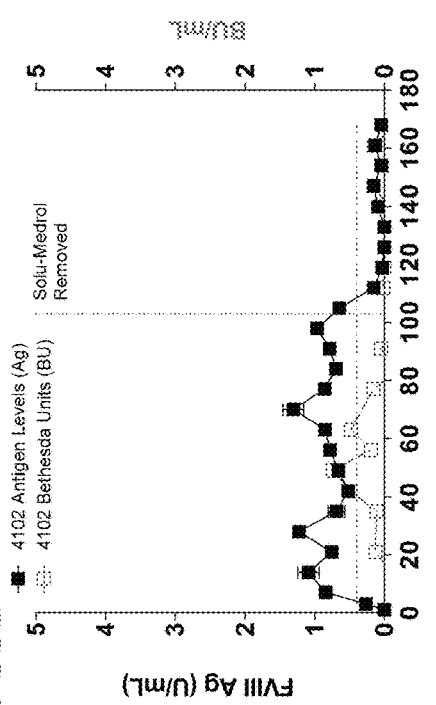

For the high dose animals (n=3), comprising the FVIII-BDD cDNA in AAV2/6, dosed at 6E+12 vg/kg, a similar pattern was observed (see FIG. 32). However in one animal, 3101, following the removal of Solu-medrol, anti-FVIII antibodies were not detected despite a detectable and persistent level of FVIII antigen (representing 200% of normal hFVIII levels), which could be indicative of a tolerance of animal to the human FVIII antigen.

Figure 34C:
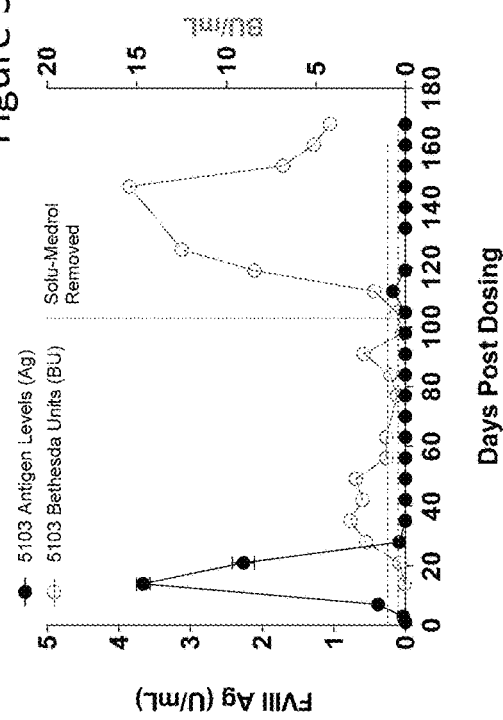
Figure 34A:
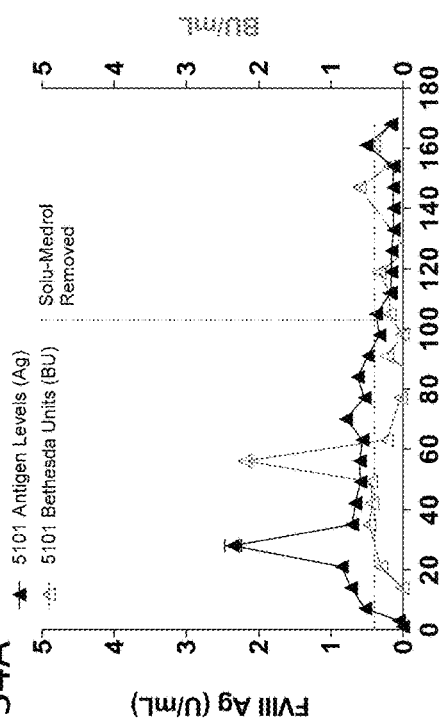
Figure 34B:
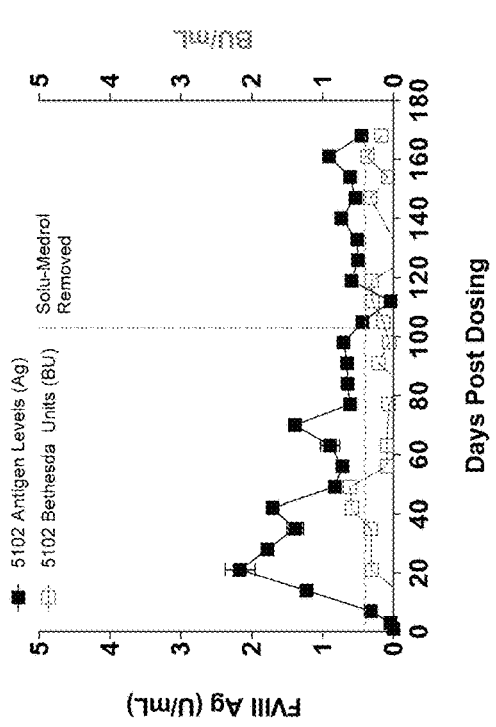
Figure 35B:
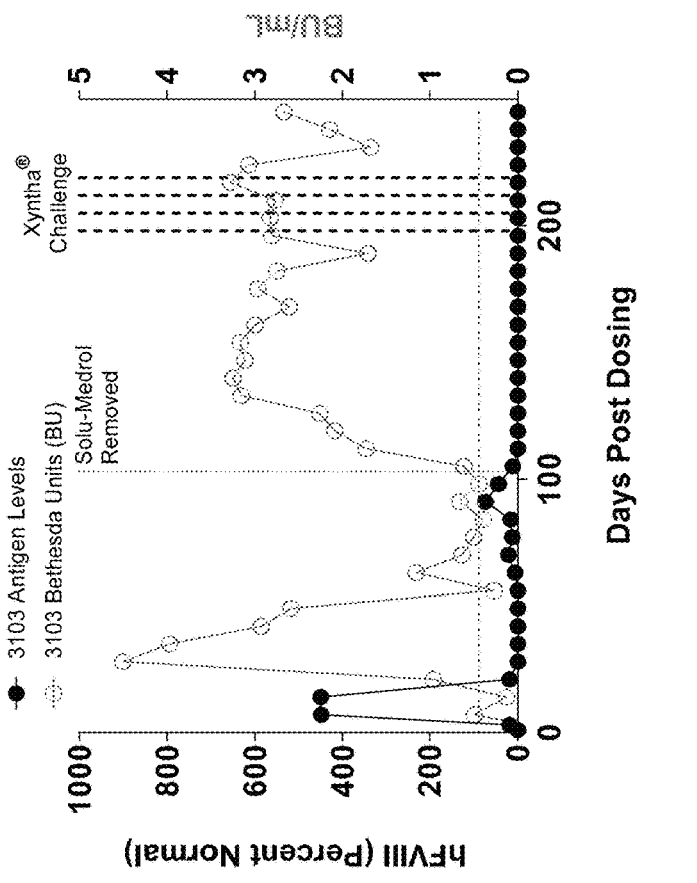
FIGS. 35A through 35F are graphs depicting challenge with therapeutic hFVIII biologic in animals expressing the transgenic hFVIII. Cynomolgus monkeys from Groups 1, 3, 4 and 5 (animals IDs 1101, 3101, 3103, 4103, 5101, 5102) were challenged with hFVIII biologic Xyntha®, consisting of four weekly infusions of 25 U/kg of Xyntha®, indicated in FIGS. 35A through 35F as upside down triangles. The Xyntha® challenges corresponded to days 198, 205, 212, 219 (following AAV hF8 cDNA test article addition at day 0). Due to the short half-life of hFVIII and the weekly plasma collection there was no increase in hFVIII levels from the hFVIII biologic Xyntha®. However there was an increase in inhibitory antibodies following Xyntha® challenge (measure by Bethesda Units, BU) in the control formulation group 1 (see animal ID 1101 which did not received AAV hF8 cDNA, FIG. 35A).
Figure 35A:
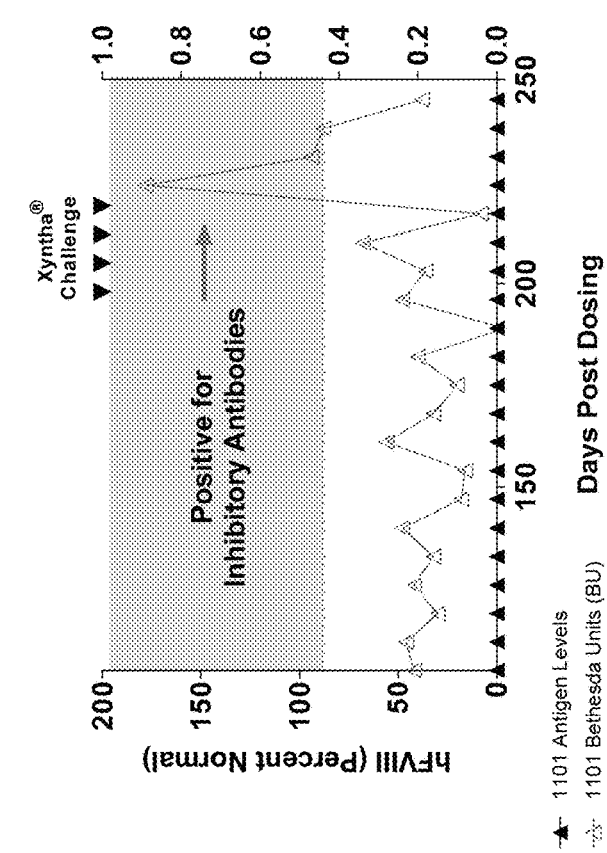
Figures 35C, 35D:
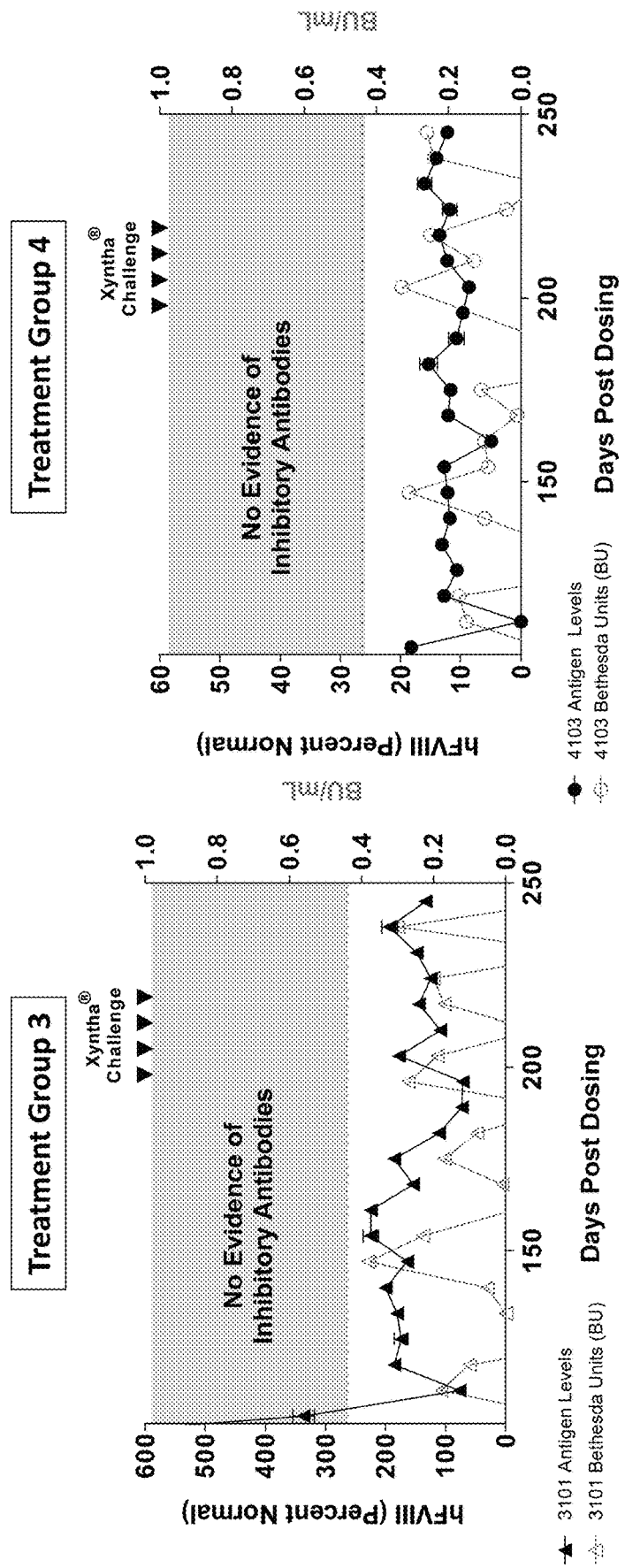
Figure 35F:
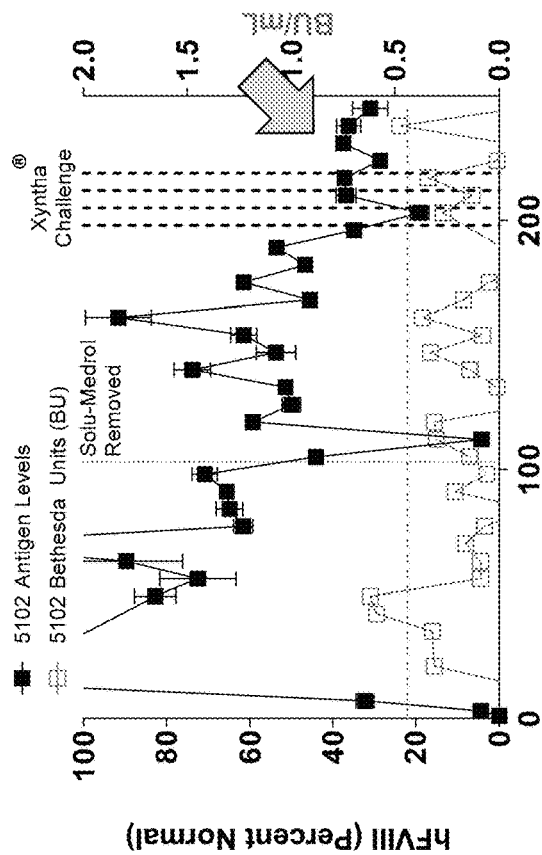
Figure 35E:
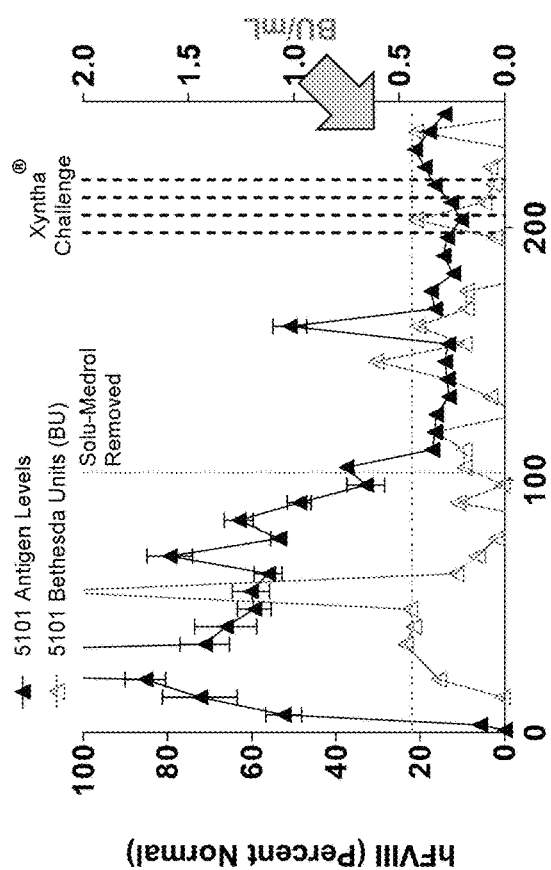

When serotype AAV2/8 was used for the delivery of the high dose, similar results were observed except that the amount of hFVIII antigen detectable in the plasma was less that measured using the AAV2/6 vector (FIG. 33). Similarly, when a different FVIII-BDD cDNA promoter module was tested (Group 5, described above) in the AAV2/8 vector, hFVIII-BDD plasma levels were similar to those seen in Group 4 (FIG. 34). However, as above, there were two individuals that maintained a detectable amount of FVIII-BDD expression (5101 and 5102), and an individual in Group 4 (4103, FIG. 33D) without a marked antibody response following the removal of the Solu-medrol, again suggestive of tolerization to the antigen following the robust response levels seen in the initial days of the experiment.

As shown in FIG. 34D, Animal No. 5101 appeared to be tolerized to hFVIII-BDD as after removal of methylprednisolone, hFVIII-BDD levels remained stable for 8 weeks at approximately 0.1U/mL (representing 10% of normal hFVIII levels). Also, as shown in FIG. 34E, Animal No. 5102 appeared to be tolerized to hFVIII-BDD as after removal of methylprednisolone, hFVIII-BDD levels remained stable for 8 weeks at approximately 0.6U/mL (representing 60% of normal hFVIII levels). It is worth noting that normal levels of hFVIII in human plasma is approximately 1U/mL or 200 ng/mL, and that expression of even 1%-5% of normal (>0.001 U/mL) can have therapeutic efficacy (Llung, RC (1999) *Thromb Haemost* 82(2):525-530).

Experiments in NHP were also conducted as described above except that different immunosuppression regimes were investigated. For these experiments, the dosing regimen shown in FIG. 26B was followed were some groups (1-5) received the immunosuppressive treatment was administered prior to test article dosing, while other groups (6-8) received immunosuppression after test article dosing.

Figure 39:
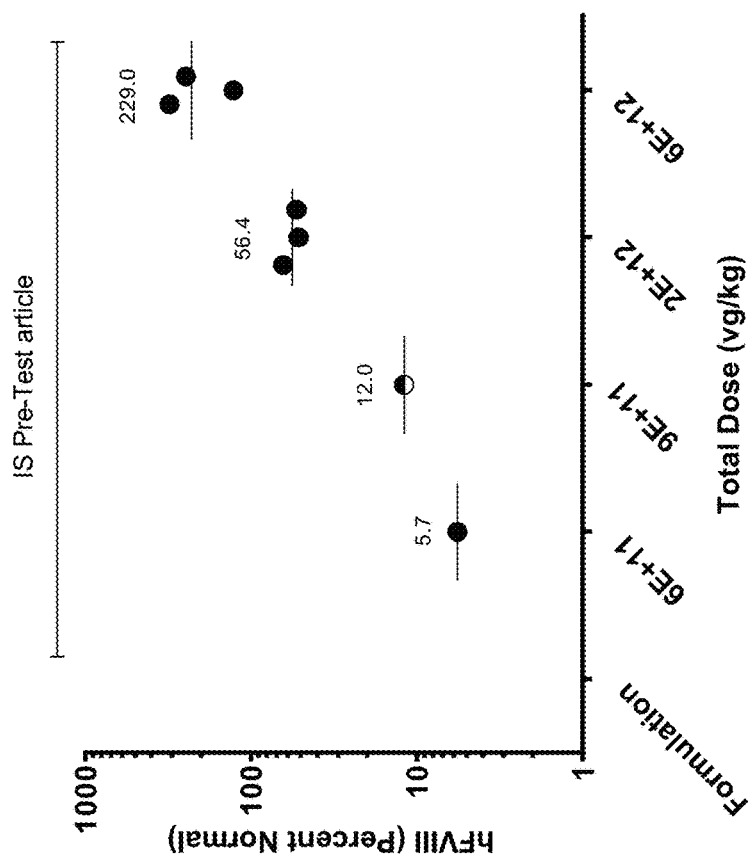
FIG. 39 is a graph showing results after redosing of the subjects in the 2E+11 vg/kg cohort shown in FIG. 38 using the same serotype results in detectable circulating human FVIII antigen levels. Group 2, representing the original 2E+11 vg/kg dosing (n=3), was redosed with 9E+11 vg/kg (n=3) at Day 56 of the study (FIG. 26B). Shown are circulating human FVIII antigen levels seven days post-redosing, denoted with a half-open circle (Day 7 at the new dose of 9E+11 vg/kg). All remaining data are the same as what was presented in FIG. 38 (peak levels as of day 56 of the study).
Figure 38:
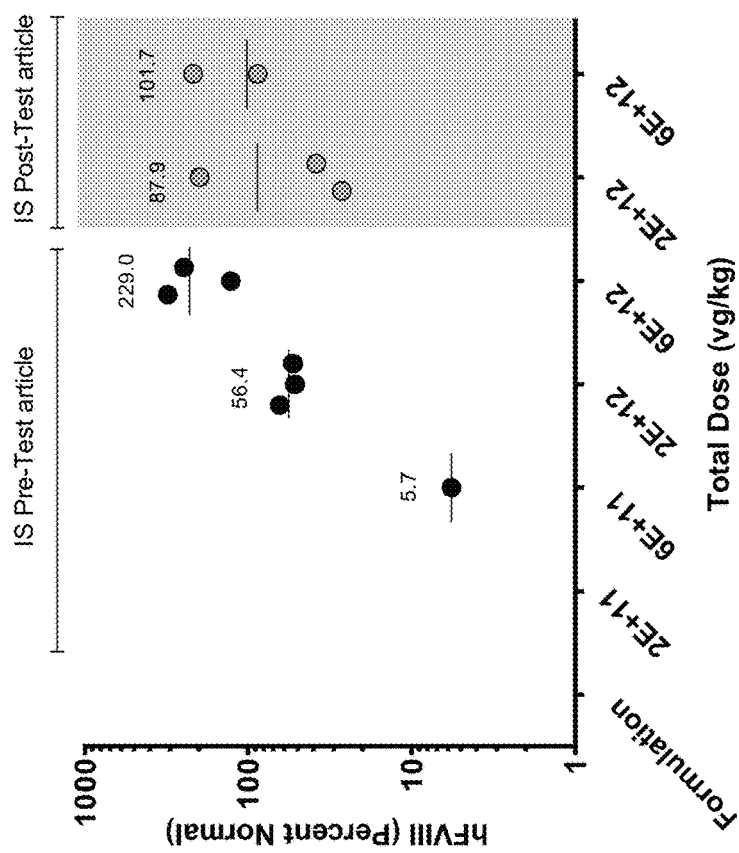
FIG. 38 is a graph showing peak human FVIII antigen levels following treatment in non-human primates (NHP) according to the schedule shown in FIG. 26B. Groups 1-5 followed an immunosuppression (IS) regimen of pre-test article injection. At dose levels of 6E+11 vg/kg (n=3, Group 3), the overall mean of peak values was 5.7% (measured by hFVIII ELISA) of normal hFVIII plasma levels in humans were achieved. At a higher dose representing 2E+12 vg/kg (n=3, Group 4), the overall mean of peak values was 56.4% and at 6E+12 vg/kg (n=3, Group 5) the overall mean of peak values was 229.0% (measured by hFVIII ELISA) of hFVIII plasma levels were achieved. Shaded in gray are Groups 7 and 8 that followed the IS post-test article regimen. At dose level 2E+12 vg/kg (n=3, Group 7) the overall mean of peak values was 87.9%, and for 6E+12 vg/kg (n=3, Group 8), 101.7%. Groups 1 and 6 were the formulation control groups, denoted as Formulation.

As shown in FIG. 38, at dose levels of 6E+11 vg/kg (n=3, Group 3), the overall mean of peak values was 5.7% (measured by hFVIII ELISA) of normal hFVIII plasma levels in humans were achieved. At a higher dose representing 2E+12 vg/kg (n=3, Group 4), the overall mean of peak values was 56.5% and at 6E+12 vg/kg (n=3, Group 5) the overall mean of peak values was 229.0% (measured by hFVIII ELISA) of hFVIII plasma levels were achieved. At dose level 2E+12 vg/kg (n=3, Group 7) the overall mean of peak values was 87.9%, and for 6E+12 vg/kg (n=3, Group 8), 101.7%. Groups 1 and 6 were the formulation control groups, denoted as Formulation. In addition, as shown in FIG. 39, re-dosing using the same serotype resulted in detectable circulating human FVIII antigen levels. These results indicate that pretreatment of the animals with immunosuppression may be helpful for maximal therapeutic protein expression. Additionally, pretreatment allows re-dosing when no neutralizing antibodies were developed during the first dose. FIG. 39 also demonstrates a dose response in the treated animals of hFVIII expression in response to varying ranges of FVIII-BDD cDNA dosed. Since the presence of even 1 to 5% of FVIII protein in the plasma is thought to have significant therapeutic efficacy in humans, clinical doses in the Ell range (resulting in 5.7 to 12.0 percent of normal levels in this experiment) are likely to provide significant therapeutic benefit. Thus, the data demonstrate that the constructs described herein result in therapeutic levels of transgene production in vivo.

Example 3: Nuclease-Mediated Targeted Integration

The constructs described in Examples 1 and 2 were also evaluated for expression when used in combination with albumin-specific nucleases for targeted integration of the expression construct into an albumin locus. In particular, the constructs were administered to HepG2 cells with albumin-specific zinc finger nucleases. See, e.g., U.S. Pat. Nos. 9,150,847; 9,255,250 and U.S. Patent Publication Nos. 20130177983; 20150159172; 20150056705 and 20150166618.

Human HepG2 liver cells were maintained per manufacturer's guidelines (ATCC, Manassas Va.). On the day of the experiment, HepG2 cells were washed, trypsinized and counted. ZFNs used were to the human albumin intron locus, together with the human Factor VIII-BDD (hFVIII) cDNA CRMSBS2 No Intron, were delivered as AAV2/6, denoted as time zero. AAV2/6 ZFNs were delivered at 3.0E+05 and AAV2/6 hFVIII cDNA CRMSBS2 No Intron at 3.0E+04, 6.0E+04 and 1.2E+05 for 1E+05 cells per well of a 24-well dish. Thus the expression constructs were administered at increasing doses from 3.0E+04, 6.0E+04 and 1.2E+05 together with ZFN 3.0E+05. Control samples included administration of the CRMSGS2 SBR Intron 3 transgene alone or with GFP, ZFN alone or GFP alone. The following day media was exchanged. Supernatants were analyzed for secreted hFVIII using the hFVIII ELISAs described below at 19 days post-AAV2/6 virus addition.

Secreted human Factor VIII-BDD levels were determined using Affinity Biologicals (Canada) ELISA kit (FVIII-AG) according to the manufacture's protocol with the exception of the human Factor VIII standard. The human Factor VIII standard used in the ELISA assay is a recombinant purified human Factor VIII (#F0016-06) from US Biologicals (Salem, Mass.). Briefly, HepG2 supernatant was added to the plate, incubated with rocking at room temperature for one and a half hours, followed by washing three times with wash buffer provided in the kit. Detecting antibody, provided with the kit, was added and incubated for forty five minutes at room temperature, followed by washing three times with wash buffer provided in the kit. TMB substrate provided with kit was added and allowed to develop for ten minutes. The reaction was stopped with stop solution and absorbance read at 450 nM using a plate reader.

Figure 36B:
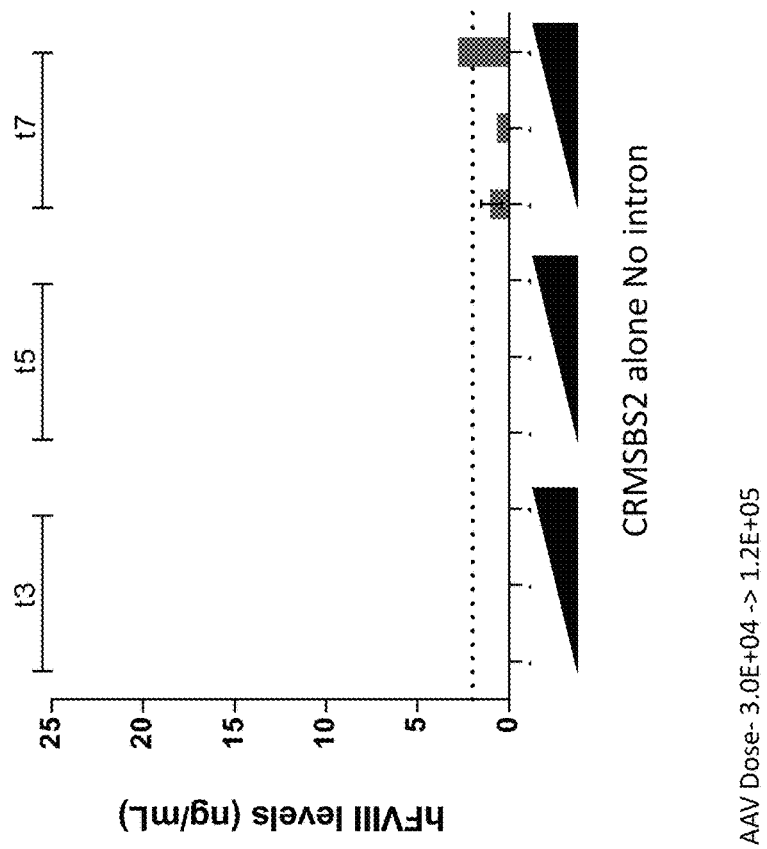
FIGS. 36A and 36B depict in vitro expression of hVIII-BDD from the endogenous albumin locus in HepG2 cells.
Figure 36A:
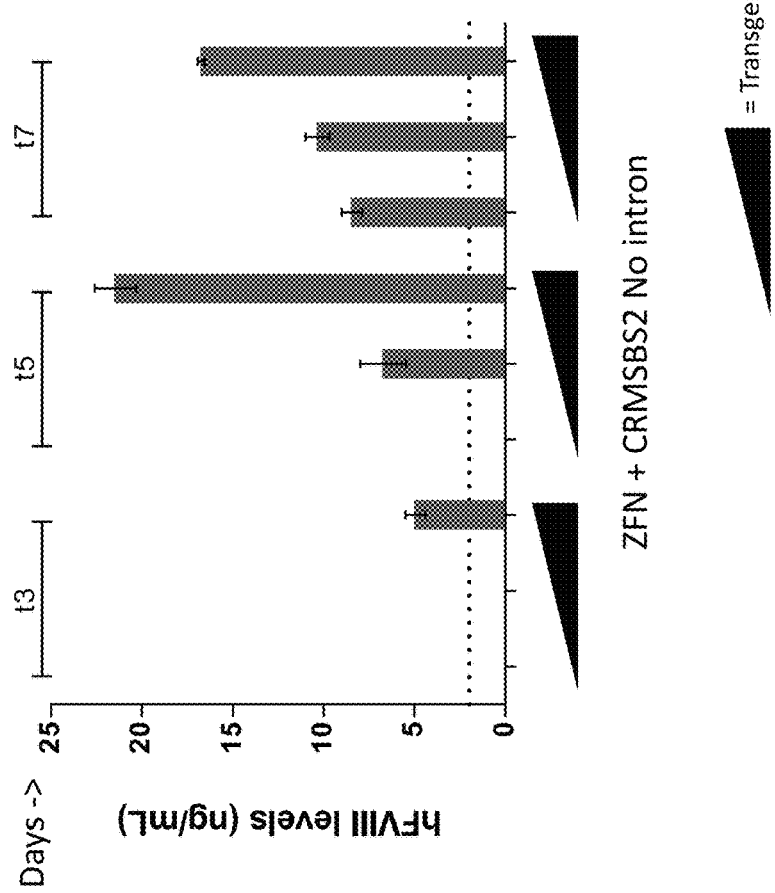

The total level of hFVIII-BDD protein detected in HepG2 cellular supernatant over time (t=days) following administration of albumin-targeted ZFNs (SBS #47171/47898, see PCT Patent Publication WO 2015/089077) and the indicated construct was analyzed (FIG. 36). In the presence of both the FVIII BDD expression construct and the ZFN, secreted FVIII BDD was detected in the supernatant three days after treatment at the highest dose of FVIII BDD transgene, and then detectable at a lower dose on day five, and detectable at all levels on day seven. In the absence of ZFN, FVIII BDD in the supernatant was barely detectable above the background of the assay at day seven. Data shown are of n=3 biological replicates. Error bars represent the standard error of the mean of technical replicates. Dotted line represents the limit of detection of the hFVIII ELISA. Secreted hFVIII-BDD was only weakly detected in the absence of the ZFNs, as the episomal hFVIII-BDD is likely diluted or degraded prior to build up of sufficient amounts of detectable secreted hFVIII-BDD from that episome.

Figure 37:
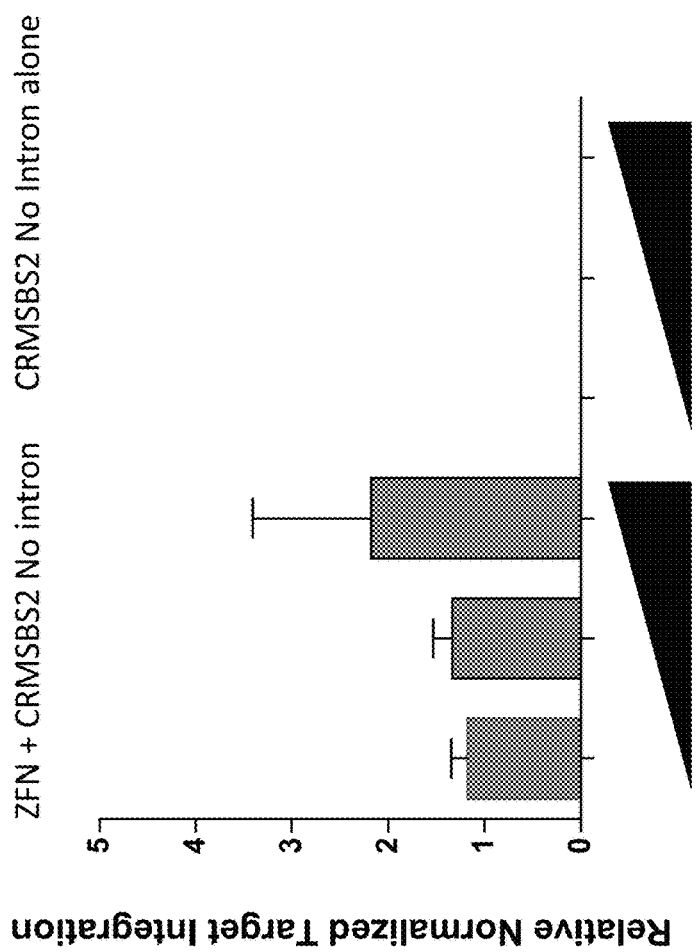
FIG. 37 is a graph showing in vitro detection of hFVIII-BDD transgene targeted integration at the endogenous albumin locus. Targeted integration was detected by quantitative PCR comprising the albumin insertion site. The 5' PCR primer was located within the endogenous human albumin locus, the PCR probe is located within the ITR of the hFVIII-BDD cassette and the 3' primer within the hFVIII-BDD transgene. The numbers displayed are normalized to the house-keeping gene GAPDH.

Furthermore, as determined by quantitative PCR (using a 5' primer is located within the endogenous human albumin locus and a probe is located within the ITR of the hFVIII-BDD cassette and the 3' primer within the hFVIII-BDD), targeted integration (by NHEJ) of the indicated constructs was achieved only in the presence of the albumin-specific ZFNs (FIG. 37). Thus these data demonstrate successful integration of the hFVIII-BDD cassette and expression of the encoded F8 protein.

Figure 40A:
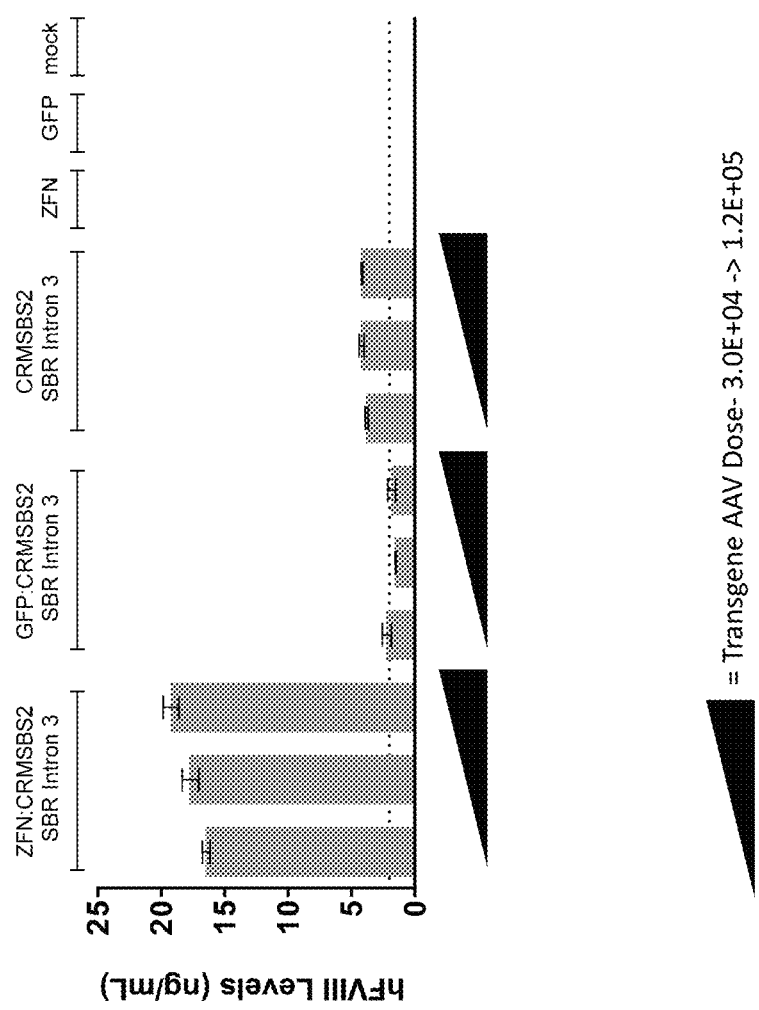

These experiments were repeated testing another set of albumin-specific ZFNs (SBS #42906/43043, see PCT Patent Publication WO 2015/089046). The results (FIGS. 40A and 40B) show expression of FVIII protein in the supernatant of these cells and targeted integration of the transgene.

Albumin-specific ZFNs and constructs are subsequently delivered in vivo to animals essentially as described in Examples 1 and 2. The constructs are integrated into the endogenous albumin locus and express the transgene.

The experimental design for the in vivo studies are shown below in Table 5. In brief, F1 generation male C57BL/6 pups mice were used for the in vivo study (test article denoted in Table 5). The ZFNs used in the study were SBS #48641 and SBS #31523 (See U.S. Patent Publication 2014-0017212). The study complied with the animal welfare act for humane care and use of animals. Test articles were thawed at room temperature prior to dosing, and all animals received a single subcutaneous 1004, injection as outlined below. The ZFN dose was 1.5E+11 vg per mouse and the F8 cDNA dose was 1.5E+11 vg per mouse. Blood was collected following euthanasia from two or three pups per group on each of Days 7, 14, 21, and 28 and processed to plasma for analysis of circulating levels of hFVIII in plasma using the In house hFVIII ELISA for mouse. Tissues were collected from all mice for analysis of levels of gene modification by deep sequencing (indels, insertions and deletions), mRNA analysis by RT-PCR, vector genome analysis using qPCR and target integration analysis using qPCR.

TABLE 5

Experimental Design

| Group No. | Test Article Description | Test Material | ZFN Dose (vg/mouse) | F8 cDNA Dose (vg/mouse) | Total AAV Dose (vg/mouse) | Total AAV Dose$^a$ (vg/kg) | Number of Male Pups | Dose Volume (μL)$^b$ |
|---|---|---|---|---|---|---|---|---|
| 1 | Formulation Buffer | SGMO.01 | 0 | 0 | 0 | 0 | 9 | 100 |
| 2 | ZFNs + F8 cDNA | SGMO.02 | $1.5 \times 10^{11}$ per ZFN | $1.5 \times 10^{11}$ | $4.5 \times 10^{11}$ | $3.75 \times 10^{14}$ | 12 | 100 |
| 3 | F8 cDNA | SGMO.03 | 0 | $1.5 \times 10^{11}$ | $1.5 \times 10^{11}$ | $1.25 \times 10^{14}$ | 12 | 100 |

$^a$Total AAV dose calculated using a 1.2 g body weight
$^b$Administered once in one volume of 100 μL.

Levels of F8 detected in the plasma are presented below in Table 6, as well as the amount of targeted integration of the FVIII-BDD transgene.

TABLE 6

F8 expression and transgene integration

| Day | Sample # | Group # | Description | Animal # | F8 Levels (ELISA) U/mL | ng/mL | Indels % | Target Integration Mean | SEM |
|---|---|---|---|---|---|---|---|---|---|
| 7 | 1 | 1 | Formulation | 101 | 0.002 | 0.4 | N.S. | 0 | |
| 7 | 2 | 1 | Formulation | 201 | 0.006 | 1.2 | N.S. | 0 | |
| 7 | 3 | 2 | ZFN/F8 cDNA | 401 | 0 | 0 | 7.8 | 1.48 | 0.00 |
| 7 | 4 | 2 | ZFN/F8 cDNA | 501 | 0.006 | 1.2 | 8.4 | 4.15 | 1.13 |
| 7 | 5 | 2 | ZFN/F8 cDNA | 601 | 0.082 | 16.4 | 12.5 | 11.38 | 3.82 |
| 7 | 6 | 3 | F8 cDNA | 901 | 0.022 | 4.4 | N.S. | 0 | |
| 7 | 7 | 3 | F8 cDNA | 1001 | 0.012 | 2.4 | N.S. | 0 | |
| 7 | 8 | 3 | F8 cDNA | 1101 | 0.006 | 1.2 | N.S. | 0 | |
| 14 | 1 | 1 | Formulation | 301 | 0.006 | 1.2 | N.S. | 0 | |
| 14 | 2 | 1 | Formulation | 102 | 0.006 | 1.2 | N.S. | 0 | |
| 14 | 3 | 2 | ZFN/F8 cDNA | 701 | 0.124 | 24.8 | 14.4 | 4.45 | 1.76 |
| 14 | 4 | 2 | ZFN/F8 cDNA | 402 | 0.037 | 7.4 | 16.1 | 3.02 | 0.09 |
| 14 | 5 | 2 | ZFN/F8 cDNA | 502 | 0.169 | 33.8 | 11.7 | 2.93 | 0.71 |
| 14 | 6 | 3 | F8 cDNA | 1201 | 0.002 | 0.4 | N.S. | 0 | |
| 14 | 7 | 3 | F8 cDNA | 902 | 0.001 | 0.2 | N.S. | 0 | |
| 14 | 8 | 3 | F8 cDNA | 1002 | 0.015 | 3 | N.S. | 0 | |
| 21 | 1 | 1 | Formulation | 202 | 0 | 0 | N.S. | 0 | |
| 21 | 2 | 1 | Formulation | 302 | 0.006 | 1.2 | N.S. | 0 | |
| 21 | 3 | 2 | ZFN/F8 cDNA | 602 | 0.082 | 16.4 | 15.7 | 21.11 | 1.11 |
| 21 | 4 | 2 | ZFN/F8 cDNA | 702 | * | * | 18.6 | 4.76 | 1.36 |
| 21 | 5 | 2 | ZFN/F8 cDNA | 403 | * | * | 16.7 | 5.72 | 2.36 |
| 21 | 6 | 3 | F8 cDNA | 1102 | 0.012 | 4.4 | N.S. | 0 | |
| 21 | 7 | 3 | F8 cDNA | 903 | 0.022 | 2.4 | N.S. | 0 | |
| 28 | 1 | 1 | Formulation | 103 | 0.006 | 1.2 | N.S. | 0 | |
| 28 | 4 | 1 | Formulation | 603 | 0 | 0 | N.S. | 0 | |
| 28 | 2 | 2 | ZFN/F8 cDNA | 303 | 0.004 | 0.8 | 9.4 | 1.00 | 0.68 |
| 28 | 3 | 2 | ZFN/F8 cDNA | 503 | 0.128 | 25.6 | 17.3 | 5.96 | 1.26 |
| 28 | 5 | 2 | ZFN/F8 cDNA | 703 | 0.001 | 0.2 | 15.0 | 1.93 | 0.49 |
| 28 | 6 | 3 | F8 cDNA | 1003 | 0.004 | 0.8 | N.S. | 0 | |
| 28 | 7 | 3 | F8 cDNA | 1103 | 0.002 | 0.4 | N.S. | 0 | |

* data not available
NS: not significantly above background

Thus, FVIII was detectable in the mouse pups following administration of the albumin-specific nucleases and the FVIII-BDD transgene. Insertion of the transgene was also detectable at a higher amount in those mice treated with both the ZFNs and the transgene.

Thus, nuclease-mediated targeted integration of the constructs described herein provides for transgene expression in hepatic cells.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of providing a protein to a subject in need thereof, the method comprising administering to the liver of the subject an AAV vector, wherein the AAV vector comprises a polynucleotide expression construct between a 5' inverted terminal repeat (ITR) and a 3' ITR, the polynucleotide expression construct comprising at least one insulator sequence selected from SEQ ID NOs: 28, 29, 30, and 38, a liver-specific enhancer sequence, a promoter sequence and a transgene, wherein the transgene encodes the protein and the protein is produced in the subject.

2. The method of claim 1, wherein the transgene is integrated into the genome of a liver cell.

3. The method of claim 2, further comprising administering one or more nucleases to the subject, wherein the nuclease cleaves an endogenous albumin gene and the transgene is integrated into the endogenous albumin gene, wherein the nuclease is a Zinc finger nuclease (ZFN), a TAL-effector nuclease (TALEN), or a CRISPR/Cas nuclease system, that is provided in an expression vector, a liposome, or a nanoparticle.

4. A method of providing a protein to a subject in need thereof, the method comprising administering to the liver of the subject an AAV vector, wherein the AAV vector comprises a polynucleotide expression construct between a 5' inverted terminal repeat (ITR) and a 3' ITR, the polynucleotide expression construct comprising a liver-specific enhancer sequence, a promoter sequence, an intron sequence as shown in any one of SEQ ID NO:15, 16, 17, or nucleotides 340-432 of SEQ ID NO:37 and a transgene, wherein the transgene encodes the protein and the protein is produced in the subject.

5. The method of claim 4, wherein the transgene is integrated into the genome of a liver cell.

6. The method of claim 5, further comprising administering one or more nucleases to the subject, wherein the nuclease cleaves an endogenous albumin gene and the transgene is integrated into the endogenous albumin gene, wherein the nuclease is a ZFN a TALEN, or a CRISPR/Cas nuclease system, that is provided in an expression vector, a liposome, or a nanoparticle.

7. The method of claim 1, wherein the enhancer sequence has mutations at positions 1, 5, 14, 32 and/or 39 of any of SEQ ID NOs:1 13.

8. The method of claim 7, wherein the transgene is integrated into the genome of a liver cell.

9. The method of claim 8, further comprising administering one or more nucleases to the subject, wherein the nuclease cleaves an endogenous albumin gene and the transgene is integrated into the endogenous albumin gene, wherein the nuclease is a ZFN, a TALEN, or a CRISPR/Cas nuclease system, that is provided in an expression vector, a liposome, or a nanoparticle.

10. The method of claim 1, wherein the AAV vector further comprises an intron sequence, wherein the enhancer sequence comprises a wild-type or mutated Serpin 1 enhancer sequence; and/or the promoter sequence comprises a wild-type or mutated transthyretin (TTR) promoter sequence; and/or the intron sequence comprises a wild-type or mutated minute virus of mice (MVM) intron sequence.

11. The method of claim 10, wherein the AAV vector comprises two insulator sequences flanking the enhancer sequence, the promoter sequence, the intron sequence, and the transgene.

12. The method of claim 11, wherein the first insulator sequence comprises SEQ ID NO: 28 and the second insulator sequence comprises SEQ ID NO: 30.

13. The method of claim 1, wherein the transgene encodes a protein lacking or deficient in a hemophilia or a lysosomal storage disease.

14. The method of claim 13, wherein the transgene further encodes a nuclease, wherein the nuclease is a ZFN, a TALEN, or a CRISPR/Cas nuclease system.

15. The method of claim 1, wherein the polynucleotide expression construct comprises the sequence of SEQ ID NO: 34.

16. The method of claim 1, wherein the polynucleotide expression construct comprises the sequence of SEQ ID NO: 37.

17. The method of claim 16, wherein the ITRs are AAV2 ITRs.

18. The method of claim 17, wherein the vector further comprises an AAV serotype 6 (AAV6) capsid.

19. A method of providing replacement Factor VIII to a subject with hemophilia A in need thereof, the method comprising administering to the liver of the subject an AAV vector, wherein the AAV vector comprises a polynucleotide expression construct between a 5' inverted terminal repeat (ITR) and a 3' ITR from AAV2, wherein the polynucleotide expression construct comprises the sequence of SEQ ID NO: 37, and wherein the AAV vector further comprises an AAV6 capsid.

20. The method of claim 4, wherein the enhancer sequence comprises a wild-type or mutated Serpin 1 enhancer sequence; and/or the promoter sequence comprises a wild-type or mutated the transthyretin (TTR) promoter sequence.

21. The method of claim 4, wherein the polynucleotide expression construct further comprises at least one insulator sequence and the polynucleotide expression construct optionally comprises a polyadenylation signal.

22. The method of claim 4, wherein the transgene encodes a protein lacking or deficient in a hemophilia or a lysosomal storage disease.

23. The method of claim 22, wherein the transgene further encodes a nuclease, wherein the nuclease is a ZFN, a TALEN, or a CRISPR/Cas nuclease system.

24. The method of claim 1, wherein the transgene encodes replacement Factor VIII.

25. The method of claim 4, wherein the transgene encodes replacement Factor VIII.

26. The method of claim 19, wherein the AAV vector is administered intravenously into a peripheral vein of the subject.

* * * * *

UNITED STATES PATENT AND TRADEMARK OFFICE
CERTIFICATE OF CORRECTION

PATENT NO. : 11,452,782 B2
APPLICATION NO. : 16/172461
DATED : September 27, 2022
INVENTOR(S) : Kretschmann et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 825 days.

Signed and Sealed this
Twenty-eighth Day of January, 2025

Coke Morgan Stewart
*Acting Director of the United States Patent and Trademark Office*